(12) United States Patent
Perez Fernandez et al.

(10) Patent No.: US 9,663,429 B2
(45) Date of Patent: May 30, 2017

(54) VITAMIN D ANALOGUES OF PHARMACEUTICAL INTEREST

(71) Applicants: UNIVERSIDADE DE SANTIAGO DE COMPOSTELA, Santiago de Compostela (ES); UNIVERSIDADE DA CORUÑA, A Coruña (ES); SERVIZO GALEGO DE SAUDE (SERGAS), Santiago de Compostela (ES)

(72) Inventors: Roman Perez Fernandez, Santiago de Compostela (ES); Samuel Seoane Ruzo, Santiago de Compostela (ES); Antonio Mouriño Mosquera, Santiago de Compostela (ES); Miguel Maestro Saavedra, Santiago de Compostela (ES); Jose Esteban Castelao Fernandez, Santiago de Compostela (ES); Pranjal Gogoi, Santiago de Compostela (ES)

(73) Assignees: UNIVERSIDADE DE SANTIAGO DE COMPOSTELA, Santiago de Compostela (ES); UNIVERSIDADE DA CORUNA, A Coruna (ES); SERVIZO GALEGO DE SAUDE (SERGAS), Santiago de Compostela (ES)

( * ) Notice: Subject to any disclaimer, the term of this patent is extended or adjusted under 35 U.S.C. 154(b) by 0 days.

(21) Appl. No.: 15/038,303

(22) PCT Filed: Nov. 19, 2014

(86) PCT No.: PCT/ES2014/070855
§ 371 (c)(1),
(2) Date: May 20, 2016

(87) PCT Pub. No.: WO2015/075291
PCT Pub. Date: May 28, 2015

(65) Prior Publication Data
US 2016/0297731 A1  Oct. 13, 2016

(30) Foreign Application Priority Data

Nov. 20, 2013  (ES) .................................. 201331689

(51) Int. Cl.
| | | |
|---|---|---|
| A61K 31/59 | (2006.01) |
| C07C 35/21 | (2006.01) |
| A61K 45/06 | (2006.01) |
| A61K 31/593 | (2006.01) |

(52) U.S. Cl.
CPC .............. *C07C 35/21* (2013.01); *A61K 31/59* (2013.01); *A61K 31/593* (2013.01); *A61K 45/06* (2013.01); *C07C 2101/14* (2013.01)

(58) Field of Classification Search
USPC ........................................ 514/19.2, 167, 168
See application file for complete search history.

(56) References Cited

U.S. PATENT DOCUMENTS 4,358,406 A  11/1982 Deluca et al.
2009/0131378 A1* 5/2009 Moras ................. C07D 307/12
514/167

FOREIGN PATENT DOCUMENTS

ES  2166377  4/2002
ES  2368824  11/2011

OTHER PUBLICATIONS

Spain Patent Office, International Search Report, PCT/ES2014/070855, Jan. 20, 2015, 3 pages.

* cited by examiner

*Primary Examiner* — Pancham Bakshi

(57) ABSTRACT

The present invention relates to compounds of pharmaceutical interest. More particularly, it relates to compounds of formula (I), to processes for obtaining thereof, to the intermediates of their synthesis and processes for obtaining the latter. The compounds of formula (I) have a certain affinity with the vitamin D receptor, they are active in a similar order to 1,25α-dihydroxyvitamin $D_3$ (1,25D), with the advantage of producing less or no hypercalcemia.

20 Claims, 8 Drawing Sheets

VITAMIN D ANALOGUES OF PHARMACEUTICAL INTEREST

TECHNICAL FIELD

The present invention relates to compounds of pharmaceutical interest. More particularly, it relates to compounds of formula (I), to processes for obtaining thereof, to the intermediates of their synthesis and processes for obtaining the latter.

BACKGROUND OF THE INVENTION

The 1,25α-dihydroxyvitamin $D_3$ (1,25D) is the most active metabolite of vitamin D. It performs its biological actions by binding specifically to its nuclear receptor, the vitamin D receptor (VDR). The endocrine system of vitamin D plays a critical role in regulating the phosphorus and calcium metabolism, by stimulating intestinal absorption of these essential minerals and their mobilisation in bone tissue. Thus, vitamin D deficiency or resistance to its actions produces clinical signs at bone level, such as rickets in children or osteomalacia in adults.

Although the actions on the phosphorous and calcium metabolism are the best known, epidemiological, biochemical, cellular, or molecular genetic studies have shown their involvement in other physiological processes, since they inhibit the proliferation and induce the cell differentiation, and pathologic processes, such as psoriasis, diabetes, osteoporosis, and autoimmune, degenerative, endocrine, cardiovascular, infectious, or neoplastic diseases (De Luca H. Historical overview of vitamin D. In Vitamin D, 3rd Ed, Feldman D, Pike J W, Adams J S (Eds). Academic Press, London, U K, 2011, Volume 1, pp 3-12).

In cancer, treatment with vitamin D blocks the cell cycle and induces apoptosis, thus inhibiting tumour growth and contributing to tumour suppression. Numerous studies have evaluated the use of vitamin D as an anti-neoplastic agent, alone or in combination with other drugs for treating cancer. Vitamin D has been combined with agents that cause DNA damage (such as cisplatin or doxorubicin), with microtubule assembly blocking agents (such as taxanes), with topoisomerase inhibitors (such as etoposide), or with anti-metabolic agents (such as 5-fluororacil) (Rosen C J, Adams J S, Bikle D D, Black D M, Demay M B, Manson J E, Murad M H, Kovacs C S. The non-skeletal effects of vitamin D: an endocrine society scientific statement. Endocr Rev. 2012, 33(3):456-92; Deeb K, Trump D L, Johnson C S. Vitamin D signaling pathways in cancer: potential for anticancer therapeutics. Nature Rev Cancer 2007; 7:684-700; Ma Y, Trump D L, Johnson C S. Vitamin D in combination cancer treatment. J Cancer 2010; 1:101-7). However, the main limitation of vitamin D for clinical use is that its administration in pharmaceutical doses induces hypercalcemia (K Deeb, Trump D L, Johnson C S. Vitamin D signaling pathways in cancer: potential for anticancer therapeutics. Nature Rev Cancer 2007; 7:684-700). Therefore, the development of non hypercalcemic vitamin D analogues is particularly important for use in the treatment of diseases in which vitamin D has been shown to be useful in pre-clinical studies. For example, a vitamin D analogue, calcipotriol, is being marketed for the treatment of psoriasis, its administration being topical because of the potential risk of inducing hypercalcemia (Menter A, Korman N J, Elmets C A, Feldman S R, Gelfand J M Gordon K B, Gottlieb A, Koo J Y M, Lebwohl M, Lim H W, Van Voorhees A S, Beutner K R, Bhushan R. Guidelines of care for the management of psoriasis and psoriatic arthritis. J Am Acad Dermatol 2009; 60:643-59).

Thus, the development of new vitamin D analogues with the same properties as the natural hormone, but with little or no ability to induce hypercalcemia, is a goal to be achieved for its use in clinical practice.

SUMMARY OF THE INVENTION

The authors of the present invention have obtained compounds of formula (I) that have a certain affinity towards the vitamin D receptor, they are active in a similar order to 1,25α-dihydroxyvitamin $D_3$ (1,25D), with the advantage of producing less or no hypercalcemia. This advantage allows the therapeutic use in doses in which vitamin D is toxic.

Although these compounds of formula (I) are highly functionalised, the process for their preparation consists in few synthesis stages. An additional advantage is that the intermediates obtained in this synthetic route have high versatility in terms of the nature of the substituents, including the isotopic labelling thereof.

Thus, in one aspect, the invention relates to a compound of formula (I), or stereoisomers or pharmaceutically acceptable salts thereof,

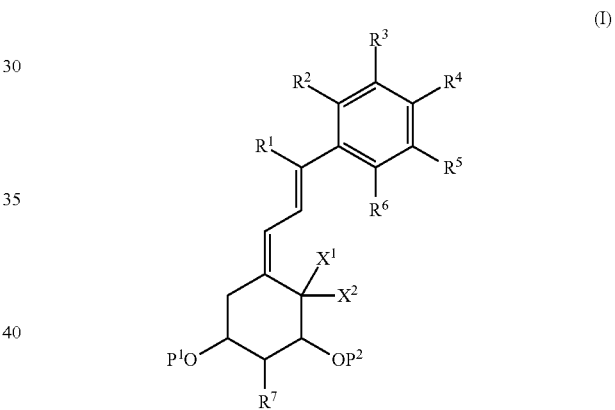

wherein each of $R^1$, $R^2$, $R^3$, $R^4$, $R^5$, $R^6$ and $R^7$ is independently selected from hydrogen, $(C_1-C_{12})$alkyl, $(C_1-C_{12})$hydroxyalkyl, $(C_2-C_{12})$alkenyl, $(C_2-C_{12})$hydroxyalkenyl, $(C_2-C_{12})$alkynyl, $(C_2-C_{12})$hydroxyalkynyl, $(C_1-C_{12})$heteroalkyl, $(C_2-C_{12})$heteroalkenyl, $(C_1-C_{12})$heteroalkynyl, $(C_6-C_{10})$aryl, $(C_3-C_{12})$heteroaryl, $(C_6-C_{10})$aryl$(C_1-C_{12})$alkyl, $(C_1-C_{12})$alkylacyl, $(C_6-C_{10})$arylacyl, $(C_1-C_{12})$alkoxyl, $(C_6-C_0)$aryloxyl, $(C_1-C_{12})$alkylcarboxy, $(C_6-C_{10})$arylcarboxy, $(C_1-C_{12})$carbocycle and $(C_3-C_{15})$heterocycle, wherein $R^1$, $R^2$, $R^3$, $R^4$, $R^5$, $R^6$ and $R^7$ are optionally substituted by $(C_1-C_{12})$alkyl or $(C_1-C_{12})$hydroxyalkyl, $X^1$ and $X^2$ are hydrogen or, together with the carbon atom to which they are bonded, form a (=$CH_2$)methylene group, and each of $P^1$ and $P^2$ is independently selected from hydrogen, $(C_1-C_{12})$alkyl, $(C_6-C_{10})$aryl, $(C_1-C_{12})$alkoxyl, $(C_6-C_{10})$aryloxyl, $(C_1-C_{12})$alkylcarboxy, $(C_6-C_{10})$arylcarboxy and —$OSiR^aR^bR^c$, wherein each of $R^a$, $R^b$ and $R^c$ are selected from $(C_1-C_{12})$alkyl, $(C_6-C_{10})$aryl, $(C_6-C_{10})$aryl, $(C_1-C_{12})$alkyl, $(C_1-C_{12})$alkoxyl, $(C_6-C_{10})$aryloxyl and $(C_3-C_{15})$heterocycle. As non-limiting examples of the $P^1$ and $P^2$ groups, mention may be made of metoxy methyl ether, metoxy methyl ether, benzyloxy methyl ether, methylthio methyl ether, trimethylsilyl ethoxymethyl ether, acetate, pivalate, benzoate and p-nitrobenzoate, wherein between 1 and 9 hydrogen atoms in the compound of formula (I) are optionally substituted with hydrogen, deuterium ($^2$H) or tritium ($^3$H) isotopes, and/or between 1 and 9 carbon atoms in the compound of formula (I) are optionally substituted with $^{11}$C, $^{13}$C, $^{14}$C isotopes.

Another aspect of the invention relates to a pharmaceutical composition comprising a therapeutically effective amount of a compound of formula (I) together with one or more pharmaceutically acceptable excipients or carriers.

Another aspect of the invention relates to the use of a compound of formula (I) for the preparation of a drug.

DETAILED DESCRIPTION OF THE INVENTION

Definitions

Figure 1:
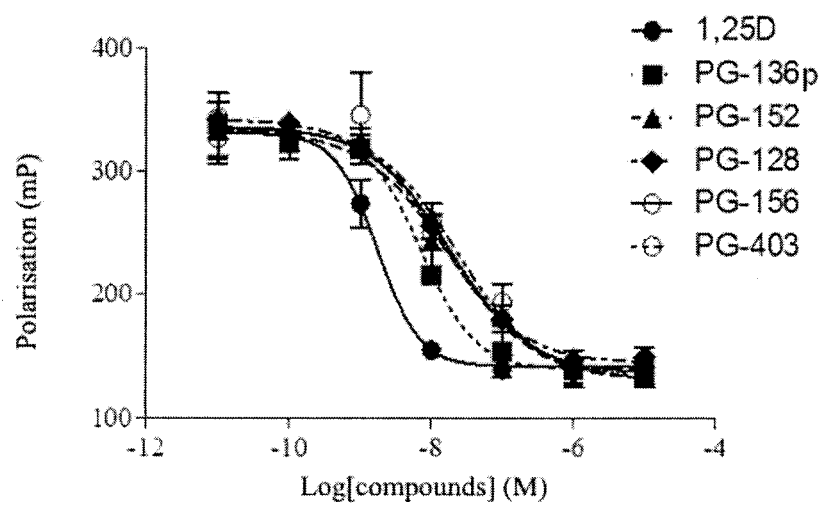
FIG. 1. Competitive binding experiment of 1,25D and various analogues according to the present invention to the vitamin D receptor. Increasing concentrations of 1,25D and analogues (from $10^{-11}$ up to $10^{-5}$ [M]) were incubated with the vitamin D receptor in a competitive binding assay for the receptor. The IC$_{50}$ value, which corresponds to 50% of the inhibition of each compound's polarisation and is derived from values of the dose-response curves is indicated in the description (Table 1). The values represent the mean of at least two experiments. The error bars represent the standard deviation (SD).

"$(C_1-C_{12})$Alkyl" means a straight or branched hydrocarbon chain, consisting of carbon and hydrogen atoms, without unsaturations, of 1 to 12, preferably eight, more preferably one to four carbon atoms, which binds to the rest of the molecule by a single bond, which may be optionally isotopically labelled so that one or more hydrogens are substituted by deuterium ($^2$H) or tritium ($^3$H) and/or one or more carbons are substituted by 11-carbon ($^{11}$C), 13-carbon ($^{13}$C) or 14-carbon ($^{14}$C) optionally substituted by one or more substituents selected from the group consisting of a halogen atom, a $(C_1-C_{12})$alkylcarboxy group, a $(C_6-C_{10})$arylcarboxy group, a $(C_1-C_{12})$alkoxyl group, a cyano group, a nitro group, a $(C_1-C_{12})$thioalkoxyl group, a $(C_1-C_{12})$heteroalkyl group, a $(C_3-C_{15})$heterocyclic group or $CF_3$. Examples of alkyl groups include, without limitation, methyl, ethyl, n-propyl, i-propyl, n-butyl, t-butyl, n-pentyl, cyclopropyl, etc.

"$(C_1-C_{12})$carbocycle" means a closed hydrocarbon chain consisting of carbon and hydrogen atoms, without unsaturation, of 1 to 12, preferably eight, more preferably five to eight carbon atoms, which binds to the rest of the molecule by a single bond, which may optionally be isotopically labelled so that one or more hydrogens are substituted by deuterium ($^2$H) or tritium ($^3$H) and/or one or more carbons are substituted by 11-carbon ($^{11}$C), 13-carbon ($^{13}$C) or 14-carbon ($^{14}$C).

"$(C_2-C_{12})$Alkenyl" means a straight or branched hydrocarbon chain, consisting of carbon and hydrogen atoms, containing at least one unsaturation, conjugated or not, of 2 to 12, preferably of two to eight, more preferably of two to four carbon atoms, which binds to the rest of the molecule by a single bond, which may optionally be isotopically labelled so that one or more hydrogens are substituted by $^2$H or $^3$H and/or one or more carbons are substituted by $^{11}$C, $^{13}$C, or $^{14}$C. Alkenyl radicals may be optionally substituted by one or more substituents such as a halogen atom, a carboxy group, a $(C_1-C_{12})$alkoxyl group, a cyano group, a nitro group, a $(C_1-C_{12})$thioalkoxyl group, a $(C_1-C_{12})$heteroalkyl group, a $(C_3-C_{15})$heterocyclic group or $CF_3$. Examples of alkenyl groups include, without limitation, vinyl, allyl, butenyl (e.g. 1-butenyl, 2-butenyl, 3-butenyl), or pentenyl (e.g. 1-pentenyl, 2-pentenyl, 3-pentenyl, 4-pentenyl).

"$(C_2-C_{12})$Alkynyl" means a straight or branched hydrocarbon chain, consisting of carbon and hydrogen atoms, that contains at least one triple carbon-carbon bond, conjugated or not, of two to twelve, preferably of two to eight, more preferably of two to four carbon atoms, which binds to the rest of the molecule by a single bond, such as —CCH, —CH$_2$CCH, —CCCH$_3$, —CH$_2$CCCH$_3$, and which may optionally be isotopically labelled so that one or more hydrogens are substituted by $^2$H or $^3$H and/or one or more carbons are substituted by $^{11}$C, $^{13}$C or $^{14}$C. Alkynyl radicals may be optionally substituted by one or more substituents such as a halogen atom, a carboxy group, a $(C_1-C_{12})$alkoxyl group, a cyano group, a nitro group, a $(C_1-C_{12})$thioalkoxyl group, a $(C_3-C_{15})$heterocyclic group or $CF_3$.

"$(C_1-C_{12})$Hydroxyalkyl" means a straight, branched, cyclic or acyclic hydrocarbon chain formed by carbon and hydrogen atoms, without unsaturations, of 1 to 12, preferably from one to eight carbon atoms, which binds to the rest of the molecule by a single bond, which is substituted by a hydroxyl group, optionally protected by a protecting group as described in Wuts, P. G. M., Greene, T. W.; "Protective Groups in Organic Synthesis", 4rd Ed., John Wiley & Sons, Inc. 2007, New Jersey, pages 24-222. Preferably, the chain is branched and the hydroxyl group is protected with alkyl ethers and esters such as metoxy methyl ether, metoxy methyl ether, benzyloxy methyl ether, methylthio methyl ether, trimethylsilyloxy methyl ether, acetate, pivalate, benzoate and p-nitrobenzoate. Examples of substituted hydroxyalkyl include, without limitation, 5-methyl-5-hydroxyhexyl and 6-methyl-6-hydroxyheptyl, 5-ethyl-5-hydroxyheptyl and 6-ethyl-6-hydroxyoctyl. Examples of non substituted hydroxyalkyl include, without limitation, 5-hydroxyhexyl and 6-hydroxyheptyl, 5-hydroxyheptyl and 6-hydroxyoctyl.

"$(C_1-C_{12})$Hydroxyalkenyl" means a straight or branched hydrocarbon chain, consisting of carbon and hydrogen atoms, that contains at least one unsaturation, conjugated or not, of 2 to 12, preferably of two to eight, more preferably of two to four carbon atoms, which binds to the rest of the molecule by a single bond, which may optionally be isotopically labelled so that one or more hydrogens are substituted by $^2$H or $^3$H and/or one or more carbons are substituted by $^{11}$C, $^{13}$C, or $^{14}$C. Alkenyl radicals may be optionally substituted by one or more substituents such as a halogen atom, a carboxy group, a $(C_1-C_{12})$alkoxyl group, a cyano group, a nitro group, a $(C_1-C_{12})$thioalkoxyl group, a $(C_1-C_{12})$heteroalkyl group, a $(C_3-C_{15})$heterocyclic group.

"$(C_1-C_{12})$Hydroxyalkynyl" means a straight or branched hydrocarbon chain, consisting of carbon and hydrogen atoms, that contains at least one triple carbon-carbon bond, conjugated or not, of two to twelve, preferably of two to eight, more preferably of two to four carbon atoms, which binds to the rest of the molecule by a single bond, such as —CCH, —CH$_2$CCH, —CCCH$_3$, —CH$_2$CCCH$_3$, and which may optionally be isotopically labelled so that one or more hydrogens are substituted by $^2$H or $^3$H and/or one or more carbons are substituted by $^{11}$C, $^{13}$C or $^{14}$C. Alkynyl radicals may be optionally substituted by one or more substituents such as a halogen atom, a carboxy group, a $(C_1-C_{12})$alkoxyl group, a cyano group, a nitro group, a $(C_1-C_{12})$thioalkoxyl group, a $(C_3-C_{15})$heterocyclic group or $CF_3$.

"$(C_6-C_{10})$Aryl" means an aromatic hydrocarbon of 6 to 10 carbon atoms, such as phenyl or naphthyl, and optionally may be isotopically labelled so that one or more hydrogens are substituted by $^2$H or $^3$H and/or one or more carbons are substituted by $^{11}$C, $^{13}$C, or $^{14}$C. Aryl radicals may be optionally substituted by one or more substituents selected from the group consisting of a halogen atom, a hydroxyl group, a carboxy group, a $(C_1-C_{12})$alkoxyl group, a cyano group, a nitro group, a $(C_1-C_{12})$thioalkoxyl group, a $(C_1-C_{12})$alkyl group or $CF_3$.

"$(C_6-C_{10})$Aryl $(C_1-C_{12})$Alkyl" means one or more aryl groups bonded to the rest of the molecule via an alkyl radical, for example, benzyl, 3-(phenyl) propyl, etc.

"$(C_3-C_{15})$Heterocycle" means a stable ring of 3 to 15 members formed by carbon atoms and from 1 to 5 heteroatoms selected from nitrogen, oxygen and sulfide, preferably a ring of 4 to 8 members formed by one or more heteroatoms, and more preferably a ring of 5 to 6 members with one or more heteroatoms. For purposes of this invention, the heterocyclic groups may be monocyclic, bicyclic or tricyclic systems, which may include fused rings; and the atom of nitrogen or sulfide in the heterocyclic ring may be optionally oxidised; the nitrogen atom may be optionally quarternarised; and the heterocyclic radical may be partially or fully saturated. $C_3-C_{15}$)Heterocyclic radicals may be aromatic (e.g. may have one or more aromatic rings), in which case they are considered as "$(C_3-C_{15})$heteroaryls" for the purposes of the present invention. The heterocyclic ring may be optionally substituted by one or more substituents selected from the group consisting of a halogen atom, a hydroxy group, a carboxy group, a $(C_1-C_{12})$alkoxyl group, a $(C_1-C_{12})$alkyl group, a $(C_1-C_{12})$thioalkoxyl group, a cyano group, a nitro group or $CF_3$. Examples of such heterocycles include, without limitation, furan, thiophene, pyrrole, imidazole, triazole, isothiazole, benzothiophene, benzofuran, indole, benzoimidazole, tetrahydrofuran.

"$(C_1-C_{12})$Alkoxyl" means a radical of formula —O—$(C_1-C_{12})$alkyl, for example, methoxy, ethoxy, propoxy, etc.

"$(C_1-C_{12})$Thioalkoxyl" means a radical of formula —S—$(C_1-C_{12})$alkyl, for example, thiomethoxy, thioethoxy, thiopropoxy, etc.

"$(C_6-C_{10})$Aryloxyl" means a radical of formula —O—$(C_6-C_{10})$aryl, for example, phenoxy, benziloxy, etc.

"$(C_1-C_{12})$Alkylcarboxy" means an alkyl group which binds to the rest of the molecule through the oxygen of a (—$CO_2$—)carboxy group.

"$(C_6-C_{10})$Arylcarboxy" means an aryl group which binds to the rest of the molecule through the oxygen of a (—$CO_2$—)carboxy group.

"$(C_1-C_{12})$Alkylacyl" means an alkyl group which binds to the rest of the molecule through a (—CO—)carbonyl group.

"$(C_6-C_{10})$Aryacyl" means an aryl group which binds to the rest of the molecule through a (—CO—)carbonyl group.

"$(C_1-C_{12})$Heteroalkyl" means an alkyl group in which one or more carbons are substituted by heteroatoms, preferably 1 to 5, wherein the heteroatom can be selected from oxygen, sulphur, selenium, tellurium, nitrogen, phosphorus, arsenic.

"$(C_1-C_{12})$Heteroalkenyl" means an alkenyl group in which one or more carbons are substituted by heteroatoms, preferably 1 to 5, wherein the heteroatom can be selected from oxygen, sulphur, selenium, tellurium, nitrogen, phosphorus, arsenic.

"$(C_1-C_{12})$Heteroalkynyl" means an alkynyl group in which one or more carbons are substituted by heteroatoms, preferably 1 to 5, wherein the heteroatom can be selected from oxygen, sulphur, selenium, tellurium, nitrogen, phosphorus, arsenic.

The compounds of the present invention may include diastereomers and/or enantiomers, depending on the presence of chiral centres or isomers depending on the presence of multiple bonds (e.g. Z, E). Such isomers, diastereomers, enantiomers and mixtures thereof are within the scope of the present invention.

The phrase "pharmaceutically acceptable salt" as used herein, means pharmaceutically acceptable organic or inorganic salts of a compound of the invention. Examples of pharmaceutically acceptable salts include salts with inorganic acids such as hydrochloric acid, hydrobromic acid, hydroiodic acid, sulfuric acid, nitric acid and phosphoric acid; and organic acids such as methanesulfonic acid, benzenesulfonic acid, formic acid, acetic acid, trifluoroacetic acid, propionic acid, oxalic acid, malonic acid, succinic acid, fumaric acid, maleic acid, lactic acid, malic acid, tartaric acid, citric acid, ethanesulfonic acid, aspartic acid and glutamic acid.

Exemplary salts include, but are not limited to salts of sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, pamoate and p-toluenesulfonate (i.e., 1,1'-methylene-bis-(2-hydroxy-3-naphthoate)). A pharmaceutically acceptable salt may comprise the inclusion of another molecule such as an acetate ion, succinate ion or other counterion. The counterion may be an organic or inorganic part that stabilizes the parent compound charge. Furthermore, a pharmaceutically acceptable salt may have more than one charged atom in its structure. In cases where the multiple charged atoms are part of the pharmaceutically acceptable salt, they may have multiple counterions. Therefore, a pharmaceutically acceptable salt may have one or more charged atoms and/or one or more counterions.

If the inventive compound is a base, it is possible to prepare the desired pharmaceutically acceptable salt by any method available in the state of the art, for example, by treating the free base with an inorganic acid such as hydrochloric acid, hydrobromic acid, sulfuric acid, nitric acid, methanesulfonic acid, phosphoric acid, and the like, or with an organic acid such as acetic acid, maleic acid, succinic acid, fumaric acid, malonic acid, pyruvic acid, oxalic acid, glycolic acid, salicylic acid, a pyranosidyl acid such as glucuronic acid or galacturonic acid, an α-hydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

If the compound of the invention is an acid, it is possible to prepare the desired pharmaceutically acceptable salt by any suitable method, for example, by treatment of the free acid with an inorganic or organic base such as a (primary, secondary or tertiary) amine, an alkali metal dioxide or an alkaline earth metal hydroxide, or the like. Illustrative examples of suitable salts include, but are not limited to, organic salts derived from amino acids such as glycine and arginine, ammonia, primary, secondary and tertiary amines, and cyclic amines, such as piperidine, morpholine and piperazine, and inorganic salts derived from sodium, calcium, potassium, magnesium, iron, copper, zinc, aluminium and lithium.

Typically the salt is a mesylate, a hydrochloride, a phosphate, a benzenesulfonate or a sulfate. More typically, the salt is a mesylate or a hydrochloride.

The salts, for instance salts with any of the inorganic or organic acids mentioned above, may be mono-salts or bis-salts. Therefore, for example, the mesylate salt may be the mono-mesylate or the bis-mesylate.

Compounds of Formula (I)

The compounds of formula (I) of the present invention have affinity for the vitamin D receptor, and bind specifically to the vitamin D receptor (VDR); they also inhibit cell proliferation in the same manner as 1,25D does in cell lines of keratinocytes, breast, ovarian and prostate cancer, they induce transactivation of vitamin D target genes such as 24-hydroxylase, and regulate the expression of vitamin D target genes such as p21, p27, p53 and E-cadherin. The compounds of formula (I) do not induce hypercalcemia after administration in vivo, which makes them of particular interest for the treatment of diseases related to vitamin D deficiency such as rickets, osteomalacia or fractures, or pathologies in which vitamin D may have a special indication such as, without ruling out others, psoriasis, diabetes, osteoporosis and autoimmune, degenerative, endocrinological, cardiovascular, infectious or tumour diseases.

The compounds of formula (I) are highly functionalised and they may have different substituents in the different positions of the aromatic ring and in other carbons of the system.

In a particular embodiment, in a compound of formula (I), each of $R^1$ and $R^5$ is selected independently from hydrogen, $(C_1$-$C_{12})$alkyl and $(C_1$-$C_{12})$hydroxyalkyl and $R^3$ is selected from $(C_1$-$C_{12})$alkyl and $(C_1$-$C_{12})$hydroxyalkyl. More preferably, $R^1$ is $(C_1$-$C_{12})$alkyl and $R^3$ is $(C_1$-$C_{12})$hydroxyalkyl.

In another particular embodiment, $R^7$ is hydrogen in a compound of formula (I). In another particular embodiment, $R^2$, $R^4$, and $R^6$ are hydrogen in a compound of formula (I).

In a particular embodiment, the compound of formula (I) is a compound of formula (Ia),

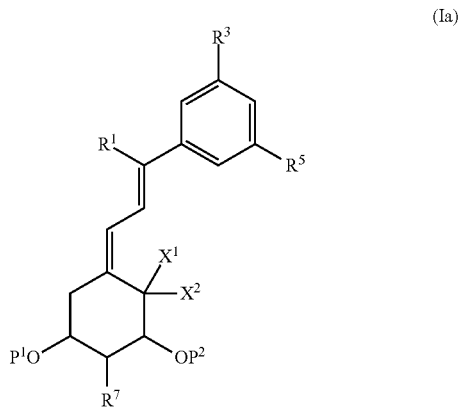

(Ia)

wherein $R^1$ is hydrogen, $(C_1$-$C_{12})$alkyl or $(C_1$-$C_{12})$hydroxyalkyl,
$R^3$ is hydrogen or $(C_1$-$C_{12})$hydroxyalkyl, $R^5$ is hydrogen or $(C_1$-$C_{12})$hydroxyalkyl,
$R^7$ is hydrogen, $(C_1$-$C_{12})$alkyl or $(C_1$-$C_{12})$hydroxyalkyl, and $X^1$, $X^2$, $P^1$ and $P^2$ have the same values as defined above.

In a particular embodiment, in a compound of formula (Ia), $R^1$ is $(C_1$-$C_{12})$alkyl, $R^3$ is $(C_1$-$C_{12})$hydroxyalkyl and $R^5$ is hydrogen. In another particular embodiment, in a compound of formula (Ia), $R^1$ is $(C_1$-$C_{12})$alkyl, $R^3$ is $(C_1$-$C_{12})$hydroxyalkyl and $R^5$ is hydroxyalkyl.

In a more particular embodiment, $R^1$ is selected from the group consisting of ethyl, propyl, butyl, hexyl and heptyl.

In a particular embodiment, in a compound of formula (Ia), $R^1$ is hydrogen, $R^3$ is $(C_1$-$C_{12})$hydroxyalkyl and $R^5$ is $(C_1$-$C_{12})$hydroxyalkyl.

In another particular embodiment, at least one of $R^1$, $R^3$ and $R^5$ in a compound of formula (I) or (Ia) is a branched $(C_1$-$C_{12})$hydroxyalkyl.

In another particular embodiment, $X^1$ and $X^2$ in a compound of formula (I) or (Ia) are methylene.

Isotopic Derivatives

Isotopic derivatives of the compounds of the invention are useful for use as internal standards in different mass spectrometry techniques or high-performance liquid chromatography coupled to nuclear magnetic resonance. The compounds of the invention incorporating $^{11}C$, $^{13}C$, $^{14}C$, $^2H$ or $^3H$ are also useful as radiopharmaceuticals, for example, but without limitation, for carrying out imaging technical research techniques "in vivo", allowing external detection of the biodistribution of the radiopharmaceutical within the body. In particular, labelling with $^{11}C$ is useful in the techniques of positron emission tomography (PET).

In the present invention, a compound "incorporating isotopic labelling" means a compound of the invention wherein from 1 to 9 hydrogen atoms are substituted by hydrogen, deuterium or tritium isotopes, and/or between 1 and 9 carbon atoms are substituted by $^{11}C$, $^{13}C$, $^{14}C$ isotopes. Preferably between 3 and 9 hydrogen atoms and 1 to 3 carbon atoms are substituted by isotopes. Preferably 1, 3, 4, 5, 6, 7, 8 or 9 hydrogen atoms are substituted by deuterium or tritium.

Thus, in a particular embodiment, the compounds of formula (I), as defined above, have incorporated isotopic labelling. In a more preferred embodiment, the isotopic labelling is selected from $^{11}C$, $^{13}C$, $^{14}C$, $^2H$ and $^3H$. In a still more preferred embodiment, the isotopic labelling is $^{11}C$.

In a particular embodiment, a compound of formula (I) incorporates isotopic labelling in $R^1$, $R^3$ and/or $R^5$. In a particular embodiment, the isotopic labelling in $R^1$, $R^3$ and/or $R^5$ is selected from the group consisting of $^2H_n$-alkyl, $^2H_n$-hydroxyalkyl, $^3H_n$-hydroxyalkyl and $^2H_n$-phenyl, where n has a value between 1 and 6. In a particular embodiment, the isotopic labelling in $R^1$, $R^3$ and/or $R^5$ is selected from the group consisting of $(C_1$-$C_4)$alkyl and phenyl, wherein one or more carbons are $^{11}C$, $^{13}C$, or $^{14}C$.

In another aspect, the invention relates to the use of compounds of formula (I) as defined above, characterised in that they incorporate isotopic labelling, as internal standards in spectroscopic and spectrometric techniques. Additionally, the invention relates to the use of compounds of formula (I) as defined above, characterised in that they incorporate isotopic labelling, as internal standards in spectroscopic and spectrometric techniques.

In another aspect, the invention relates to compounds of formula (I), as defined above, characterised in that they incorporate isotopic labelling selected from $^{11}C$, $^{13}C$, $^{14}C$, $^2H$ or $^3H$ for use as radiopharmaceuticals. A radiopharmaceutical may be useful, for example, but without limitation, for carrying out imaging technical research techniques "in vivo", allowing external detection of the biodistribution of the radiopharmaceutical within the body. Alternatively, the invention relates to the use of the compounds of formula (I), as defined above, characterised in that they incorporate isotopic labelling selected from $^{11}C$, $^{13}C$, $^{14}C$, $^2H$ or $^3H$ as radiopharmaceuticals. Preferably, the compounds of formula (I), as defined above, characterised in that they incorporate $^{11}C$, are useful as radiopharmaceuticals in positron emission tomography (PET) techniques.

In a particular embodiment, the compound of formula (I) is selected from the group consisting of:
(1R,3S,Z)-5-((E)-3-(3-(6-hydroxy-6-methylheptyl)phenyl) pent-2-enyliden)-4-methylenecyclohexane-1,3-diol,
(1R,3S,Z)-5-((E)-3-(3-(7,7,7-trideutero-6-hydroxy-6-trideuteromethyl heptyl) phenyl)pent-2-enyliden)-4-methylenecyclohexane-1,3-diol,
(1R,3S,Z)-5-((E)-3-(3-(6-hydroxy-6-methylheptyl)phenyl) hex-2-enyliden)-4-methylenecyclohexane-1,3-diol,
(1R,3S,Z)-5-((E)-3-(3-(7,7,7-trideutero-6-hydroxy-6-trideuteromethylheptyl)phenyl) hex-2-enyliden)-4-methylenecyclohexane-1,3-diol,
(1R,3S,Z)-5-((E)-3-(3-(6-hydroxy-6-methylheptyl)phenyl) hept-2-enyliden)-4-methylenecyclohexane-1,3-diol,
(1R,3S,Z)-5-((E)-3-(3-(7,7,7-trideutero-6-hydroxy-6-trideuteroheptyl) phenyl)hept-2-enyliden)-4-methylenecyclohexane-1,3-diol,
(1R,3S,Z)-5-((E)-3-(3-(6-hydroxy-6-methylheptyl)phenyl) non-2-enyliden)-4-methylenecyclohexane-1,3-diol,
(1R,3S,Z)-5-((E)-3-(3-(7, 7,7-trideutero-6-hydroxy-6-trideuteroheptyl)phenyl)non-2-enyliden)-4-methylenecyclohexane-1, 3-diol,
(1R,3S,Z)-5-((E)-3-(3-(6-hydroxy-6-methylheptyl)phenyl) dec-2-enyliden)-4-methylenecyclohexane-1,3-diol, (1R,3S,Z)-5-((E)-3-(3-(7,7,7-trideutero-6-hydroxy-6-trideuteroheptyl)phenyl)dec-2-enyliden)-4-methylenecyclohexane-1, 3-diol, (1R,3S,Z)-5-((E)-9-hydroxy-3-(3-(6-hydroxy-6-methylheptyl)phenyl)-9-methyldec-2-enyliden)-4-methylenecyclohexane-1, 3-diol, (1R,3S,Z)-5-((E)-9-hydroxy-3-(3-(7,7,7-trideutero-6-hydroxy-6-trideuteroheptyl)phenyl)-9-methyldec-2-enyliden)-4-methylenecyclohexane-1, 3-diol, (1R,3S,Z)-5-((E)-9-hydroxy-3-(3-(6-hydroxy-6-methylheptyl)phenyl)-9-methyldec-2-enyliden)-4-methylenecyclohexane-1,3-diol, (1R,3S,Z)-5-((E)-9-hydroxy-3-(3-(7,7,7-trideutero-6-hydroxy-6-trideuteroheptyl)phenyl)-9-methyldec-2-enyliden)-4-methylenecyclohexane-1,3-diol, (1R,3S,Z)-5-((E)-3-(3.5-(6-hydroxy-6-methylheptyl)phenyl)allyliden)-4-methylenecyclohexane-1,3-diol, (1R,3S,Z)-5-((E)-3-(3.5-bis(7,7,7-trideutero-6-hydroxy-6-trideuteroheptyl)phenyl)allyliden)-4-methylenecyclohexane-1,3-diol, (1R,3S,Z)-5-((E)-3-(3-(5-hydroxy-5-methylhexyl)phenyl)pent-2-enyliden)-4-methylenecyclohexane-1,3-diol, (1R,3S,Z)-5-((E)-3-(3-(6,6,6-trideutero-5-hydroxy-5-trideuterohexyl) phenyl)pent-2-enyliden)-4-methylenecyclohexane-1,3-diol, (1R,3S,Z)-5-((E)-3-(3-(5-hydroxy-5-methylhexyl)phenyl) hept-2-enyliden)4-methylenecyclohexane-1,3-diol, (1R,3S,Z)-5-((E)-3-(3-(6,6,6-trideutero-5-hydroxy-5-trideuterohexyl) phenyl)hept-2-enyliden)-4-methylenecyclohexane-1,3-diol, Synthesis of Compounds of Formula (I)

In another aspect, the invention relates to a process for the preparation of compounds of formula (I) wherein $X^1$ and $X^2$ are methylene, comprising a coupling of the compounds (II) and (III) in the presence of a metal catalyst, which is selected from the group of typical catalysts for a coupling reaction, for example and not limited to, Pd (OAc)$_2$, PdCl$_2$, Pd (PPh$_3$)$_4$, Pd (dba)$_2$, Ni(PPh$_3$)$_4$, Pd$_2$(dba)$_3$, (Ph$_3$P)$_2$PdCl$_2$. Cu compounds and Hf compounds.

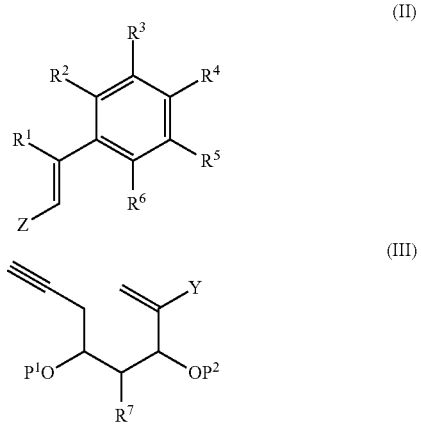

wherein $R^1$, $R^2$, $R^3$, $R^4$, $R^5$, $R^6$, $R^7$, $P^1$ and $P^2$ have the same values as defined above, Y is a halogen or a charge attracting group selected from the group comprising alkylsulfonate, arylsulfonate, triflate and phosphate, and Z is selected from indium halide, di(C$_1$-C$_{12}$)alkylindium, di(C$_6$-C$_1$)aryllithium, (C$_1$-C$_{12}$)alkyl(C$_6$-C$_{10}$)arylindium, zinc halide, di(C$_1$-C$_{12}$)alkylboron and di(C$_1$-C$_{12}$)alkoxyboron.

The invention is also related to a process for the preparation of compounds of formula (I) comprising a coupling of compounds (II) and (IV) in the presence of a metal catalyst, which is selected from the group of typical catalysts for a coupling reaction, for example and not limited to, Pd(OAc)$_2$, PdCl$_2$, Pd(PPh$_3$)$_4$, Pd(dba)$_2$, Ni(PPh$_3$)$_4$, Pd$_2$(dba)$_3$, (Ph$_3$P)$_2$PdCl$_2$, Cu compounds and Hf compounds.

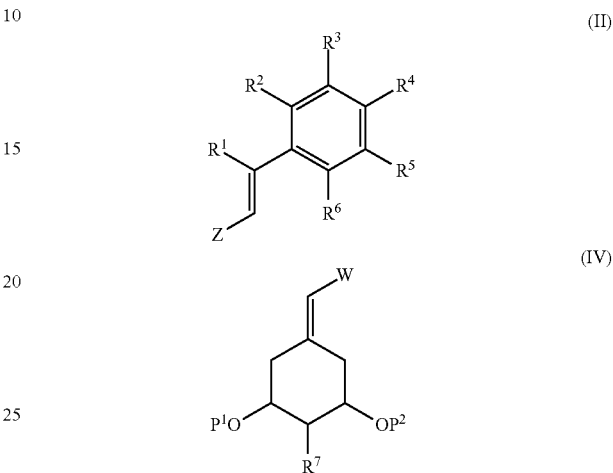

wherein Z is selected from chlorine, bromine and iodine, W is selected from (C$_1$-C$_{12}$)akylsulphonate, (C$_6$-C$_{10}$)arylsulphonate, halogen, phosphate and SiR$^a$R$^b$R$^c$ and where R$^1$, R$^2$, R$^3$, R$^4$, R$^5$, R$^6$, R$^7$, P$^1$, P$^2$, R$^a$, R$^b$ and R$^c$ have the same values as defined above.

The high functionalisation of the compounds of formula (I) that provide it with a high versatility, can only be obtained from compounds of formula (II) and (III), or alternatively (II) and (IV), with the same high functionality.

The functionally modified compounds of formula (II) can be prepared from the compound (II) through the transformation of the functional group Z. Thus, in a particular embodiment, the invention relates to a process for obtaining a functionally modified compound of formula (II) from a compound of formula (II) through a) a metalation reaction, and b) metal exchange by a group selected from indium halide, diarylindium, alkylarylindium, zinc halide, dialkylboron and dialkoxyboron.

A person skilled in the art knows the conditions to perform such a transformation, such as for example, the substitution of iodide can be carried out by metalation with an organolithium, later trapping with boron isopropoxide and exchange of the substituents of the boron (Org. Lett. 2003 (5) 523-525), it can also be carried out by a Suzuki coupling reaction, for example with bis(pinacol)diborane in the presence of a palladium catalyst, such as for example, Pd(OAc)$_2$, Pd(PPh$_3$)$_4$, Pd (dppf)Cl$_2$, in the presence of a base such as, e.g., sodium carbonate, barium hydroxide, potassium phosphate, cesium carbonate, potassium carbonate, thallium hydroxide, cesium fluoride, potassium fluoride, sodium hydroxide. (J. Am. Chem. Soc. 2002 (27) 8001-8006). A person skilled in the art also knows other possibilities, such as for example, the substitution of the bromide can be carried out by metalation with an organolitic, and subsequent reaction with indium trichloride (Org. Lett. 2004 (6) 4555-4558). In another example, the substitution of bromide can be carried out by metalation with an organolithium, and subsequent reaction with zinc dichloride (Syn-

*lett* 2003 861-863). In another example, the substitution of iodide can be carried out by direct metalation with zinc, and subsequent reaction with the copper(I) cyanide-lithium chloride complex (*Angew. Chem. Int. Ed.* 2006 (45) 6040-6044).

In the metal exchange reaction, indium trihalide, dialkylindium halide, diarylindium halide, alkylarylindium halide, zinc dihalide, dialklyboro or trialkoxyboro halide can be used.

In a particular embodiment, the invention relates to a process for the preparation of a compound of formula (II) as described above, comprising the reaction of a compound of formula (VI) with a halogenating agent,

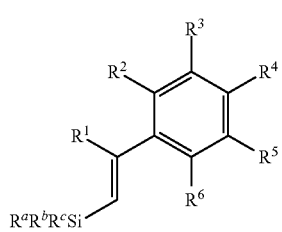

(VI)

wherein $R^1$, $R^2$, $R^3$, $R^4$, $R^5$, $R^6$, $R^a$, $R^b$ and $R^c$ have the same values as defined above.

In a particular embodiment, the halogenating agent is an iodination, chlorination, or bromidation agent. In a particular embodiment, the halogenating agent is selected from iodine, N-iodoyodosuccinimide, N-iodosaccharin, 1,3-diiodo-5,5,-dimethylhydantoin, bis(pyridine)iodonium tetrafluoroborate, bromine, N-bromosuccinimide, chlorine, N-chlorosuccinimide.

In a particular embodiment, the invention relates to a process for the preparation of a compound of formula (VII) as described above, comprising: a) the reaction of a compound of formula (VIII) with a compound of formula (V) in the presence of a catalyst

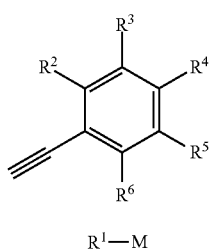

(VIII)

$R^1$—M (V)

wherein $R^1$ is selected from ($C_1$-$C_{12}$)alkyl or ($C_1$-$C_{12}$)hydroxyalkyl,
M is selected from Li, Mg-Hal, Zn-Hal, Sn($R^aR^bR^c$) and Si($R^aR^bR^c$),
Hal is chlorine, bromine or iodine and
$R^2$, $R^3$, $R^4$, $R^5$, $R^6$, $R^a$, $R^b$ and $R^c$ have the same values as those defined above, and
b) reaction of the intermediate obtained in stage a) with a silylation agent.

The catalyst used, according to a preferred embodiment, is selected from the typical group of catalysts for a coupling reaction, for example and not in a limiting manner, Pd(OAc)$_2$, PdCl$_2$, Pd(PPh$_3$)$_4$, Pd(dba)$_2$, Ni(PPh$_3$)$_4$, Pd$_2$(dba)$_3$, (Ph$_3$P)$_2$PdCl$_2$, Cu, Hf, Al. The selection of this catalyst will depend on the rest of the reaction conditions as described below. Preferably, when M is Li, Zn-Hal or Sn($R^aR^bR^c$) the reaction is catalysed by Pd catalysts; when M is Mg-Hal the reaction is catalysed by Cu catalysts; when M is Si($R^aR^bR^c$) the reaction is catalysed by Hf or Al catalysts.

Alternatively, in a particular embodiment, the invention relates to a process for the preparation of the compounds of formula (VI), as described above, comprising the reaction of a compound of formula (VIII) with trimethylsilyl cyanide catalysed by Pd or trialkylsilane hydrides, and subsequent trapping of the resulting organometallic through treatment with a silylation agent.

In a particular embodiment, the silylation agent is selected from trimethylsilyl chloride, triethylsilyl chloride and tri-iso-propilsyilyl chloride.

When, in a compound of formula (I), $R^1$ is hydrogen, necessarily $R^1$ in a compound of formula (II) is hydrogen.

Thus, in a particular embodiment, the invention relates to a process for the preparation of a compound of formula (II) where $R^1$ is hydrogen, comprising the homologation of an aldehyde group of a compound of formula (VII) by iodine

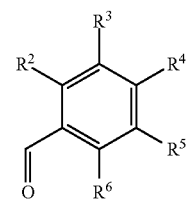

(VII)

wherein $R^2$, $R^3$, $R^4$, $R^5$ and $R^6$ have the same values as those defined above.

The conditions for carrying out such homologation of aldehyde by iodine are known to the person skilled in the art, and, therefore, can be carried out, for example, by treatment of (VII) with iodoform in the presence of chromium chloride (II) with triphenylphosphine in the presence of tetraiodomethane with iodomethylenetriphenylphosphomium in the presence of a base such as n-butyl lithium, t-butyl lithium, n-hexyl lithium, lithium hexamethyldisilazanide, sodium hexamethyldisilazanide, sodium t-butoxide or potassium t-butoxide (*Chem. Rev.* 1999 (99) 991-1045).

Compounds of formula (VIII) are known to a person skilled in the art since a large number are commercially available. In any case, the processes for the preparation of compounds of formula (VIII) are known to the person skilled in the art as they have been described in literature, such as the procedure carried out from compounds of formula (VII) by Corey-Fuchs reaction (Synthesis 2013, 45, 1513-1518), the Bestmann-Ohira reaction (*Synlett* 1996, 521-522), or from aromatic compounds of structure (IX) by a Pd catalysed Sonogashira coupling reaction with an alkyne (*J. Org. Chem.* 1997, 62, 7471-7474),

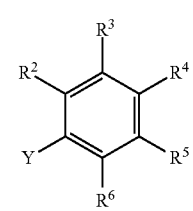

(IX)

wherein Y is a halogen (F, Cl, Br, I) or a good leaving group (triflate, mesylate, tosylate, phosphate). Thus the person skilled in the art has tools to prepare the compound of formula (VIII) of interest or to acquire it from the usual suppliers.

Biological Activity

The administration of the compounds of formula (I) of the present invention induces significant inhibition of proliferation in non-tumour keratinocyte cell lines and in breast, ovarian and prostate tumour cell lines. The inhibition of cell proliferation is similar to that obtained by 1,25D at equivalent doses. Through binding assays (binding to vitamin D receptor) it is demonstrated that the compounds of formula (I) of the present invention exhibit a specific binding to VDR and, through transactivation assays, that they induce the expression of 1,25D target genes such as the 24-hydroxylase gene. The compounds of formula (I) of the present invention, at concentrations similar to 1,25D, regulate the expression of 1,25D target genes such as p21, p27, p53 or E-cadherin. The data show that, in vivo, intraperitoneal administration of the compounds of formula (I) of the present invention does not induce hypercalcemia at doses of 0.3 μg/kg weight, contrary to that which occurs with the administration of 1,25D at the same doses. In particular, the PG-136 and PG-403 analogues injected intraperitoneally in mice every two days for 21 days at doses of 5 μg/kg weight, did not significantly raise serum calcium, compared to control animals (treated with placebo).

Thus, an aspect of the invention relates to the use of a compound of formula (I) for the preparation of a drug. In another aspect the invention retales to a compound of formula (I) as defined above for use as a drug.

Said drug may be indicated for the treatment of diseases or conditions related to vitamin D deficiency such as rickets, osteoporosis, osteodystrophy, osteomalacia, or fractures. Thus, another aspect of the present invention relates to the use of a compound of formula (I) for the preparation of a drug for the treatment of diseases or conditions related to vitamin D deficiency. This aspect can also be formulated as compound of formula (I) for use in the treatment of diseases or conditions related to vitamin D deficiency. The present invention also relates to a method for treating diseases or conditions associated with vitamin D deficiency comprising administering a therapeutically effective amount of a compound of formula (I) together with one or more pharmaceutically acceptable carriers or excipients in a subject in need thereof, particularly a human.

In a particular embodiment, the diseases and conditions associated with vitamin D deficiency are selected from the group consisting of rickets, osteoporosis, osteodystrophy, osteomalacia, and fractures.

Said drug may also be indicated for the treatment of pathologies in which vitamin D may have a special indication, such as, for example, psoriasis, diabetes, osteoporosis, autoimmune, degenerative, endocrinological, cardiovascular, infectious or tumour diseases. Thus, another aspect of the invention relates to the use of a compound of formula (I) for the preparation of a drug for the treatment of psoriasis, diabetes, autoimmune, degenerative, endocrine, cardiovascular, metabolic, infectious, or tumour diseases. This aspect can also be formulated as compound of formula (I) for use in the treatment of psoriasis, diabetes, autoimmune, degenerative, endocrine, cardiovascular, metabolic, infectious, or tumour diseases. The present invention also relates to a method for treating psoriasis, diabetes, autoimmune, degenerative, endocrine, cardiovascular, metabolic, infectious, or tumour diseases, comprising administering a therapeutically effective amount of a compound of formula (I) together with one or more pharmaceutically acceptable carriers or excipients in a subject in need thereof, particularly a human.

Another aspect of the invention relates to the use of a compound of formula (I) for the preparation of a drug for the treatment of a neoplastic disease. This aspect can also be formulated as compound of formula (I) for use in the treatment of a neoplastic disease. The present invention also relates to a method for treating a neoplastic disease comprising administering a therapeutically effective amount of a compound of formula (I) together with one or more pharmaceutically acceptable carriers or excipients in a subject in need thereof, particularly a human.

In a particular embodiment, the neoplastic diseases are selected from the group of breast, ovaric, prostate and lung cancer, leukemia, solid tumours and haematological tumours.

In another aspect, the invention relates to a combination of at least one compound of formula (I) and at least one anti-neoplastic compound. In a particular embodiment, the anti-neoplastic compound is selected from the group consisting of alkylating agents, anti-metabolites, anti-neoplastic antibiotics, topoisomerase inhibitors, mitotic inhibitors, hormonal agents, regulators of the immune system and targeted therapies.

In a particular embodiment, the alkylating agent is selected from nitrogen mustards, nitrosoureas, alkylsulfonatetriazines, ethylenimines and drugs with platinum; the anti-metabolite is selected from 5-fluorouracil, 6-mercaptopurine, capecitabine, cladribine, clofarabine, cytarabine, floxuridine, fludarabine, gemcitabine, hydroxyurea, methotrexate, pemetrexed, pentostatin and thioguanine; the anti-neoplastic antibiotic is selected from anthracyclines and non-anthracins; the topoisomerase inhibitor is selected from inhibitors of topoisomerase I and inhibitors of topoisomerase II; the mitotic inhibitor is selected from taxanes, epothilones, vinca alkaloids and estramustine; the hormonal agent is selected from anti-estrogens, aromatase inhibitors, progestins, anti-androgens, gonadotropin-releasing hormone agonists (GnRH) and analogues of the luteinizing hormone releasing hormone (LHRH); the regulator of the immune system is selected from monoclonal antibody therapy (passive immunotherapies) non-specific immunotherapies and adjuvants, immunomodulatory drugs and anticancer vaccines; and targeted therapy is selected from imatinib (Gleevec®), gefitinib (Iressa®), sunitinib (Sutent®), bortezomib (Velcade®) and trastuzumab (Herceptin®).

In a more particular embodiment, nitrogen mustards are selected from mechlorethamine, chlorambucil, cyclophosphamide, iphosphamide and melphalan; nitrosoureas are selected from streptozocin, carmustine and lomustine; alkylsulfonates consist of busulfan; triazines are selected from dacarbazine and temozolomide; ethylenimines are selected from thiotepa and altretamine; platinum drugs are selected from cisplatin, carboplatin and oxaliplatin; anthracyclines are selected from daunorubicin, doxorubicin, epirubicin and idarubicin; non anthracins are selected from actinomycin D, bleomycin and mitomycin-C; inhibitors of topoisomerase I are selected from topotecan and irinotecan; inhibitors of topoisomerase II are selected from etoposide, teniposide and/or mitoxantrone; the taxanes are selected from paclitaxel and docetaxel; epothilones consist of ixabepilone; vinca alkaloids are selected from vinblastine, vincristine and vinorelbine; anti-estrogenics are selected from fulvestrant, tamoxifen and toremifene; aromatase inhibitors are selected from anastrozole, exemestane and letrozole; progestins consist of megestrol acetate; anti-androgens are selected from bicalutamide, flutamide and nilutamide; analogues of the luteinizing hormone releasing hormone (LHRH) are selected from leuprolide and goserelin; monoclonal antibody therapy (passive immunotherapies) is selected from rituximab, and alemtuzumab; non-specific immunotherapies and adjuvants are selected from BCG, interleukin-2 and interferon-alpha; the immunomodulating drugs are selected from thalidomide and lenalidomide; and anticancer vaccines consist of sipuleucel-T (Provenge®).

Another aspect of the invention relates to the use of a combination of at least one compound of formula (I) and at least one anti-neoplastic compound, according to the above described, for the preparation of a drug for the treatment of a neoplastic disease. Another aspect of the invention relates to the use of a combination of at least one compound of formula (I) and at least one anti-neoplastic compound, as defined above, for the preparation of a drug for the treatment of a neoplastic disease. The present invention also relates to a method for treating a neoplastic disease comprising administering to a patient in need of such treatment, particularly a human, a therapeutically effective amount of the combination of at least one compound of formula (I) and at least one anti-neoplastic compound as described above, together with one or more pharmaceutically acceptable excipients or carriers.

Combination therapy can be carried out by simultaneous, separate or sequential administration of at least a therapeutically effective amount of a compound of formula (I) and at least one anti-neoplastic compound. Simultaneous administration means that at least one compound of formula (I) and at least one anti-neoplastic compound are administered by the same route and at the same time or substantially the same time. Separate administration means that at least one compound of formula (I) and at least one anti-neoplastic compound are administered by different routes. Sequential administration means that at least one compound of formula (I) and at least one anti-neoplastic compound are administered at different times by the same or different route.

Another aspect of the invention relates to a pharmaceutical composition comprising a therapeutically effective amount of a compound of formula (I), as described above, together with one or more pharmaceutically acceptable excipients or carriers.

The pharmaceutical composition of the invention can be obtained by mixing a compound of formula (I) with a pharmaceutically acceptable carrier, and thus can be administered in a plurality of dosage forms for administration, such as in solid or liquid form.

Since the compounds of formula (I) do not cause hypercalcemia, it is possible to administer the pharmaceutical composition by different administration routes, such as oral, buccal, sublingual, topical, ocular, nasal, pulmonary, aural or vaginal, intrauterine, rectal, enteric or parenteral route or any composition in the form of gel, ointment, cream or balm for its topical, ocular, nasal, vaginal or rectal administration. Preferably, the invention relates to oral administration. The pharmaceutical composition may be administered in a single administration, in multiple applications or by controlled release.

As used herein, the expression "therapeutically effective amount" means the amount of a compound that, when administered, is sufficient to prevent development of, or alleviate to some extent one or more symptoms of the disease or condition contemplated. The particular dose of compound administered, according to this invention, obviously, will be determined by the particular surrounding circumstances, including the compound administered the route of administration, the particular condition being treated, and similar considerations.

In a particular embodiment, the compound of formula (I) in the pharmaceutical composition is comprised in amounts between 0.0001 and 10 mg/kg per day, preferably between 0.001 and 1 mg/kg per day, more preferably between 0.005 and 0.1 mg/kg per day.

The term "pharmaceutically acceptable excipients or carriers" means that each component must be compatible with the other components of the pharmaceutical composition and should also be suitable for use in contact with the tissue or organs of humans and animals without excessive toxicity, irritation, allergic response, immunogenicity, or other problems or complications commensurate with a reasonable benefit/risk relationship.

The following examples illustrate the invention and should not be construed as limiting thereof.

Throughout the description and claims the word "comprise" and its variations are not intended to exclude other technical characteristics, additives, components or steps. Furthermore, the word "comprise" includes the case "consists of". For those skilled in the art, other objects, advantages and features of the invention will be apparent in part from the description and in part from the practice of the invention. The following examples and drawings are provided as an illustration, and are not intended to be limiting of the present invention. Moreover, the present invention covers all possible combinations of particular and preferred embodiments specified herein.

Preparation of the Organozinc Compound (1)

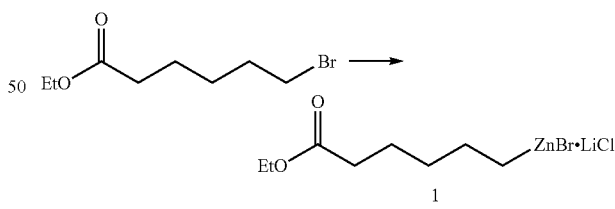

Anhydrous LiCl (1.14 g, 26.89 mmol) was dried in a reaction tube at 160° C. for 20 min under high vacuum. Zn powder (1.75 g, 26.89 mmol) was added under argon and the mixture was dried again at 160° C. under high vacuum. The reaction tube was evacuated and filled with argon three times. THF (15 mL) was added and the Zn was activated with 1,2-dibromoethane (0.06 mL, 0.67 mmol) and TMSCl (0.017 mL, 0.13 mmol). Ethyl 6-bromohexanoate (3 g, 13.45 mmol) was added and the reaction mixture was stirred at 55° C. overnight. The solution 1 was carefully separated from excess zinc using a dry syringe.

Preparation of the Ester (2)

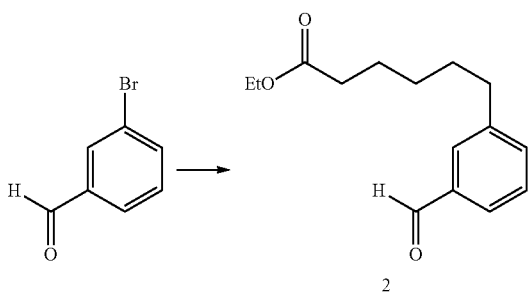 [SMILES: O=Cc1cccc(Br)c1 ; CCOC(=O)CCCCCc1cccc(C=O)c1]

3-bromobenzaldehyde (1.5 g, 8.1 mmol) was dissolved in THF (5 mL). $Pd_2(dba)_3$ (0.074 g, 0.08 mmol) and $t-Bu_3P$ (0.162 mL, 0.162 mmol, 1M) was added. The solution of the organozincate compound 1 in THF (~1.5 equivalent) was added to the reaction. The mixture was stirred for 30 min at it (room temperature) and then quenched with $NH_4Cl$ (aq. sat.: aqueous saturated solution). The mixture was extracted with $Et_2O$. The combined organic phase was dried, concentrated and purified by flash chromatography to give the ester 2 (1.95 g, 7.858 mmol, 97%). $^1H$ NMR (250 MHz, $CDCl_3$): δ=9.96 (s, 1H), 7.60-7.72 (m, 2H), 7.37-7.46 (m, 2H), 4.08 (q, J=7.1 Hz, 2H), 2.66 (t, J=7.5 Hz, 2H), 2.26 (t, J=7.4 Hz, 2H), 1.56-1.71 (m, 4H), 1.26-1.42 (m, 2H), 1.21 (t, J=7.1 Hz, 3H); HRMS (EI+): [M]+ calculated for $C_{15}H_{20}O_3$ 248.1412. found 248.1413.

Preparation of the Vicinal Dibromide (3)

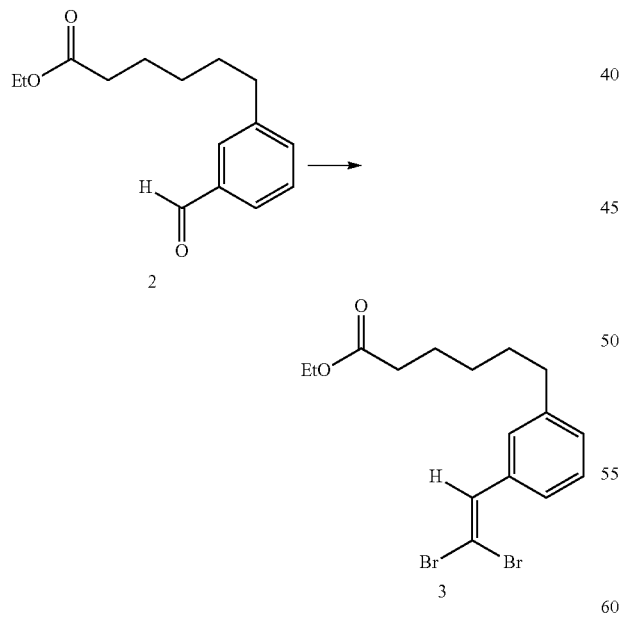

$Ph_3P$ (3.96 g, 15.1 mmol) and Zn (0.987 g, 15.1 mmol) were stirred in $CH_2Cl_2$ (40 mL) at rt. After stirring for 15 min, the mixture was cooled at 0° C. $CBr_4$ (5 g, 15.1 mmol) was added. The mixture was stirred at 0° C. for 1 h and at rt for 1.5 h. The solution of the ester 2 (1.5 g, 6.04 mmol) in $CH_2Cl_2$ (10 mL) was added to the reaction via cannula. After stirring for 1 h at rt, the reaction was filtered through celite and solids were washed with $Et_2O$. The organic phase was dried, concentrated and the residue purified by flash chromatography to give the dibromide 3 (2.24 g, 5.54 mmol, 92%). $^1H$ NMR (250 MHz, $CDCl_3$): δ=7.3 (s, 1H), 7.2-6.9 (m, 4H), 3.97 (q, J=7.1 Hz, 2H), 2.47 (t, J=7.6 Hz, 2H), 2.14 (t, J=7.5 Hz, 2H), 1.4-1.58 (m, 4H), 1.16-1.28 (m, 2H), 1.09 (t, J=7.1 Hz, 3H); HRMS (EI+): [M]+ calculated for $C_{16}H_{20}Br_2O_2$ 401.9830. found 401.9841.

Preparation of the Alkyne (4)

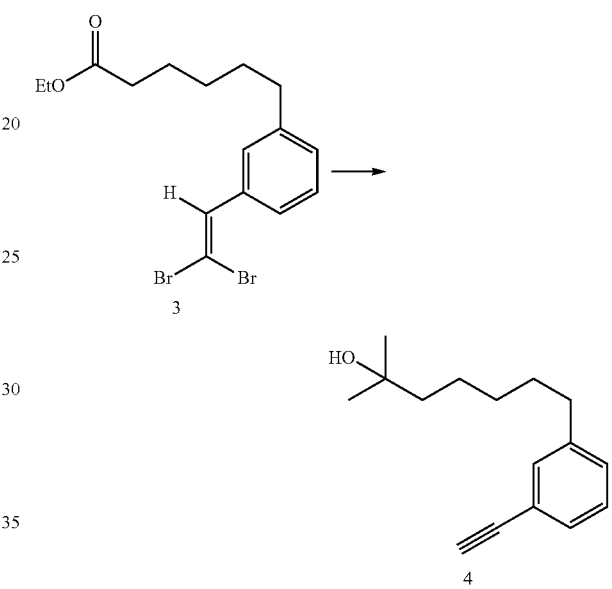

A solution of MeLi in $Et_2$ or (19.8 mL, 29.7 mmol, 1.5 M) was added to a solution of the dibromide 3 (2 g, 4.95 mmol) in THF (30 mL) at −78° C. The reaction mixture was left to reach rt and quenched with $NH_4Cl$ (aq. sat.). The mixture was extracted with $Et_2O$. The combined organic phase was dried, concentrated and purified by flash chromatography to provide the alkyne 4 (0.89 g, 3.86 mmol, 78%). $^1H$ NMR (250 MHz, $CDCl_3$): δ=6.91-7.16 (m, 4H), 2.85 (s, 1H), 2.38 (t, J=7.5 Hz, 2H), 1.35-1.49 (m, 2H), 1.07-1.29 (m, 6H), 0.99 (s, 6H); HRMS (EI+): [M+H]+ calculated for $C_{16}H_{23}O$ 231.1749. found 231.1754.

Preparation of the Silylether (5)

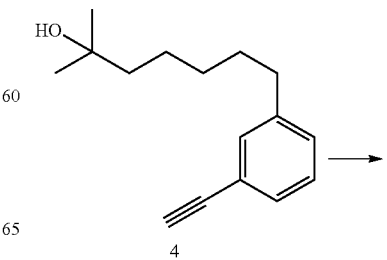

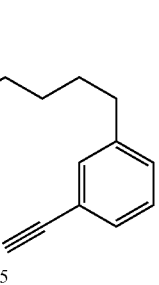

5

TESOTf (2.34 mL, 10.33 mmol) and Et₃N (2.86 mL, 20.66 mmol) were added to a solution of the alkyne 4 (1.58 g, 6.89 mmol) in CH$_2$Cl$_2$ (30 mL) at −78° C. After stirring for 3 h at −78° C., the reaction was quenched with NH$_4$Cl (aq. sat.). The mixture was extracted with Et$_2$O. The combined organic phase was dried, concentrated and purified by flash chromatography to provide the silylether 5 (2.25 g, 6.53 mmol, 95%). $^1$H NMR (250 MHz, CDCl$_3$): δ=6.98-7.2 (m, 4H), 2.9 (s, 1H), 2.44 (t, J=7.5 Hz, 2H), 1.39-1.55 (m, 2H), 0.99-1.08 (m, 6H), 1.04 (s, 6H), 0.81 (t, J=7.9 Hz, 9H), 0.42 (q, J=7.5 Hz, 6H); HRMS (CI+): [M+H]$^+$ calculated for C$_{22}$H$_{37}$OSi 345.2614. found 345.2618.

Preparation of the (E)-vinylsilane (6)

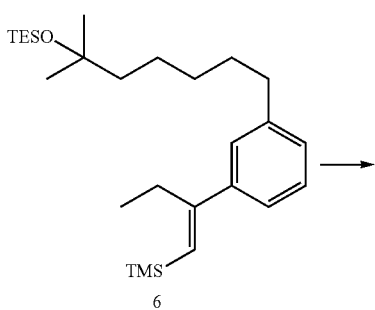

Anhydrous LiCl (0.177 g, 4.18 mmol) and CuI (0.206 g, 2.081 mmol) were dried in a reaction tube at 120° C. for 3 h under vacuum. THF (3 mL) was added and stirred for 30 min at rt. The mixture was cooled at −60° C. After 5 min, a solution of EtMgBr in THF (1.4 mL, 4.18 mmol, 3M) was added dropwise. The mixture was stirred at −60° C. for 1 hr. A solution of the alkyne 5 (0.3 g, 0.87 mmol) and HMPA (0.7 mL) in THF (5 mL) was added via cannula to the reaction mixture at −60° C. After 15 min, a mixture of HMPA (0.3 mL) and TMSCl (0.53 mL, 4.18 mmol, freshly distilled) was added. The mixture was left to reach it for 7 h and then was poured on NH$_4$Cl (aq. sat.). The mixture was extracted with Et$_2$O. The organic phase was dried, concentrated and purified by flash chromatography to give the vinylsilane 6 (0.309 g, 0.691 mmol, 79%). $^1$H NMR (250 MHz, CDCl$_3$): δ=6.9-7.2 (m, 4H), 5.66 (s, 1H), 2.44-2.67 (m, 4H), 1.16-1.69 (m, 8H), 1.12 (s, 6H), 0.79-0.98 (m, 12H), 0.5 (q, J=7.8 Hz, 6H), 0.13 (bs, 9H); HRMS (EI+): [M]$^+$ calculated for C$_{27}$H$_{50}$OSi$_2$ 446.3400. found 446.3405.

Preparation of the (E)-vinyl iodide (7)

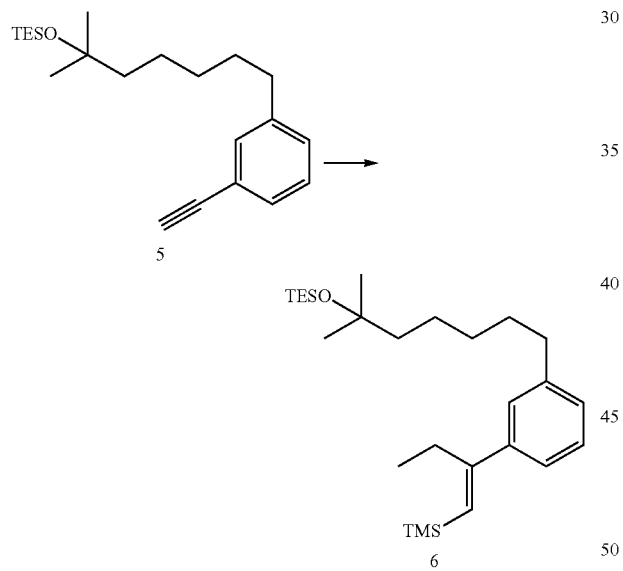

A solution of vinylsilane 6 (0.3 g, 0.671 mmol) in CH$_2$Cl$_2$ (20 mL) was cooled at −45° C. N-iodosuccinimide (0.151 g, 0.671 mmol) was added and the reaction mixture was stirred for 3 h at −45° C. The reaction was quenched with Na$_2$S$_2$O$_3$ (aq. sat.) at −45° C. and then left to reach rt. The mixture was extracted with CH$_2$Cl$_2$. The combined organic phase was dried, concentrated and purified by flash chromatography to give the vinyl iodide 7 (0.331 g, 0.661 mmol, 99%). $^1$H NMR (250 MHz, CDCl$_3$): δ=6.91-7.13 (m, 4H), 6.19 (s, 1H), 2.38-2.61 (m, 4H), 1.09-1.56 (m, 8H), 1.02 (bs, 6H), 0.73-0.89 (m, 12H), 0.41 (q, J=7.8 Hz, 6H); HRMS (EI+): [M]$^+$ calculated for C$_{24}$H$_{41}$OSiI 500.1971. found 500.1974.

Preparation of the (E)-1-alkenylboronate (8)

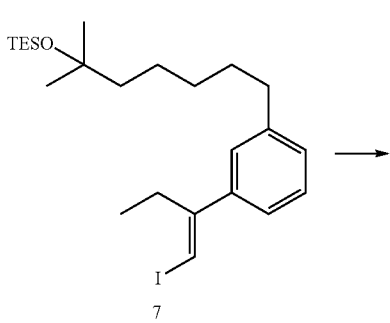

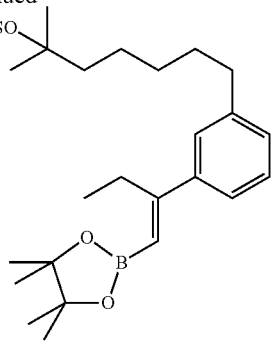

8

Pd(dppf)Cl$_2$·CH$_2$Cl$_2$ (0.0155 g, 0.019 mmol), KOAc (0.188 g, 1.92 mmol, vacuum dried at 120° C. for 2 h) and bis(pinacolato)diboran (0.195 g, 0.77 mmol) were added successively to a solution of the vinyl iodide 7 (0.32 g, 0.64 mmol) in DMSO (3 mL). After stirring 1 h at 80° C., the reaction mixture was cooled at rt and water was added. The mixture was extracted with Et$_2$O. The combined organic phase was dried, concentrated and purified by flash chromatography to give the vinyl boronic ester 8 (0.227 g, 0.453 mmol, 71%). $^1$H NMR (250 MHz, CDCl$_3$): δ=6.97-7.25 (m, 4H), 5.54 (s, 1H), 2.82 (t, J=7.5 Hz, 2H), 2.52 (t, J=7.5 Hz, 2H), 1.23 (bs, 12H), 1.1 (bs, 6H), 0.79-1 (m, 12H), 0.48 (q, J=7.6 Hz, 6H); HRMS (EI+): [M]$^+$ calculated for C$_{30}$H$_{53}$BO$_3$Si 500.3857. found 500.3853.

Preparation of the (E)-vinylsilane (9)

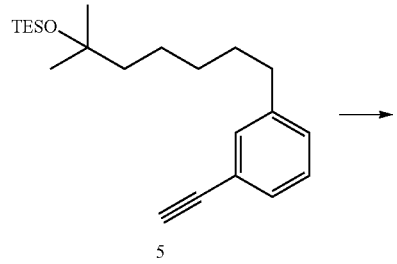

5

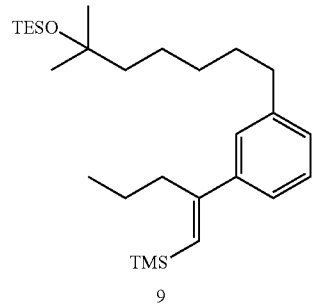

9

Following the process for preparation of (E)-vinylsilane (6), using anhydrous LiCl (0.177 g, 4.18 mmol), CuI (0.207 g, 2.09 mmol), THF (5 mL), propylmagnesium chloride in THF (2.09 mL, 4.18 mmol, 2 M), alkyne 5 (0.3 g, 0.87 mmol), HMPA (0.7 mL), THF (5 mL), HMPA (0.3 mL) and TMSCl (0.53 mL, 4.18 mmol) provided the vinylsilane 9 (0.280 g, 0.607 mmol, 70%). $^1$H NMR (250 MHz, CDCl$_3$): δ=7.05-7.31 (m, 4H), 5.78 (s, 1H), 2.57-2.72 (m, 4H), 1.6-1.77 (m, 2H), 1.29-1.53 (m, 8H), 1.23 (bs, 6H), 0.88-1.06 (m, 12H), 0.61 (q, J$_1$=7.9 Hz, J$_2$=8 Hz, 6H), 0.24 (s, 3H); HRMS (EI+): [M]$^+$ calculated for C$_{28}$H$_{52}$OSi$_2$ 460.3556. found 460.3552.

Preparation of the (E)-vinyl iodide (10)

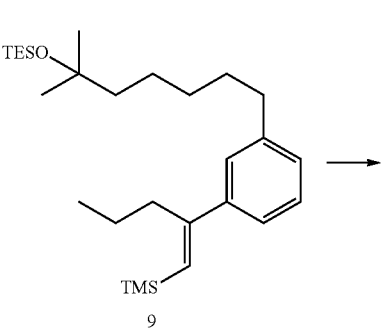

9

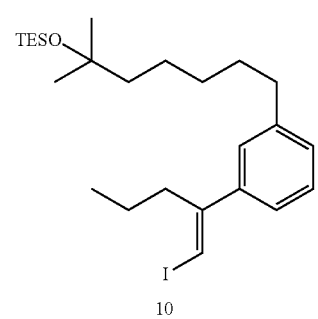

10

Following the process for preparation of (E)-vinyl iodide (7), using vinylsilane 9 (0.28 g, 0.61 mmol), CH$_2$Cl$_2$ (15 mL), N-iodosuccinimide (0.137 g, 0.61 mmol) provided the vinyl iodide 10 (0.3 g, 0.583 mmol, 96%). $^1$H NMR (250 MHz, CDCl$_3$): δ=7.07-7.25 (m, 4H), 6.38 (s, 1H), 2.56-2.73 (m, 4H), 1.56-1.71 (m, 2H), 1.19 (bs, 6H), 0.89-1.01 (m, 12H), 0.57 (q, J=7.5 Hz, 6H); HRMS (EI+): [M]$^+$ calculated for C$_{25}$H$_{43}$OSiI 514.2127. found 514.2125.

Preparation of the (E)-1-alkenylboronate (11)

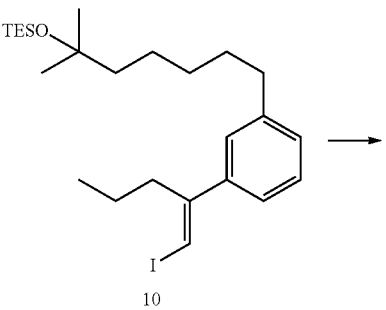

10

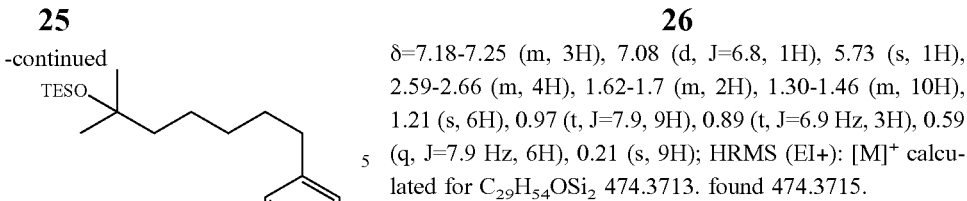

Following the process for preparation of (E)-1-alkenyl-boronate (8), using Pd (dppf)Cl$_2$·CH$_2$Cl$_2$ (0.0095 g, 0.0116 mmol), KOAc (0.115 g, 1.17 mmol), bis(pinacolato)diborane (0.119 g, 0.47 mmol) vinyl iodide 10 (0.2 g, 0.39 mmol), DMSO (3 mL) provided the vinyl boronic ester 11 (0.172 g, 0.334 mmol, 86%). $^1$H NMR (250 MHz, CDCl$_3$): δ=6.96-7.23 (m, 4H), 5.57 (s, 1H), 2.8 (t, J=7.4 Hz, 2H), 2.51 (t, J=7.4 Hz, 2H), 1.45-1.6 (m, 2H), 1.22 (bs, 12H), 1.1 (bs, 6H), 0.79-0.92 (m, 12H), 0.48 (q, J=7.6 Hz, 6H); HRMS (EI+): [M]$^+$ calculated for C$_{31}$H$_{55}$BO$_3$Si 514.4013. found 514.4014.

Preparation of the (E)-vinylsilane (12)

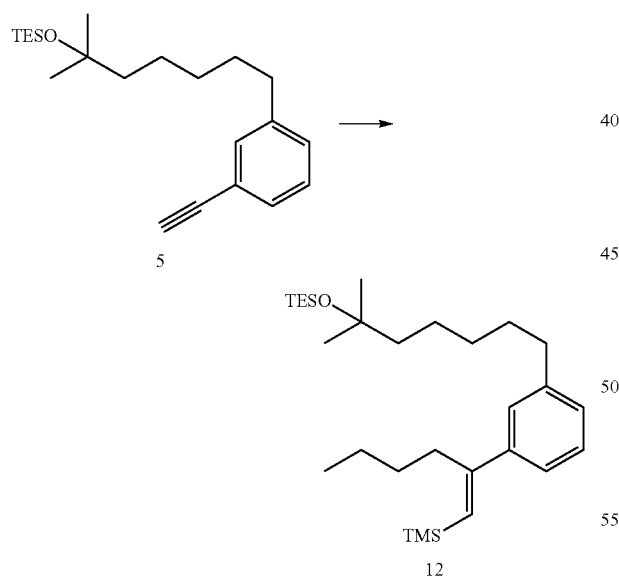

Following the process for preparation of (E)-vinylsilane (6), using anhydrous LiCl (0.177 g, 4.18 mmol), CuI (0.207 g, 2.09 mmol), THF (3 mL), butylmagnesium chloride in THF (2.09 mL, 4.18 mmol, 2 M), alkyne 5 (0.3 g, 0.87 mmol), HMPA (0.6 mL), THF (5 mL), HMPA (0.3 mL) and TMSCl (0.53 mL, 4.18 mmol) provided the vinylsilane 12 (0.273 g, 0.575 mmol, 66%). $^1$H NMR (500 MHz, CDCl$_3$): δ=7.18-7.25 (m, 3H), 7.08 (d, J=6.8, 1H), 5.73 (s, 1H), 2.59-2.66 (m, 4H), 1.62-1.7 (m, 2H), 1.30-1.46 (m, 10H), 1.21 (s, 6H), 0.97 (t, J=7.9, 9H), 0.89 (t, J=6.9 Hz, 3H), 0.59 (q, J=7.9 Hz, 6H), 0.21 (s, 9H); HRMS (EI+): [M]$^+$ calculated for C$_{29}$H$_{54}$OSi$_2$ 474.3713. found 474.3715.

Preparation of the (E)-vinyl iodide (13)

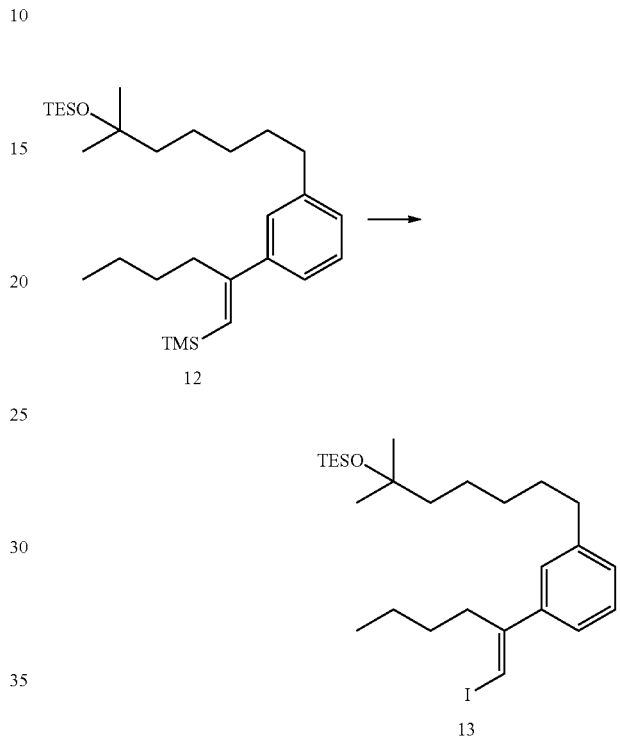

Following the process for preparation of (E)-vinyl iodide (7), using vinylsilane 12 (0.176 g, 0.37 mmol), CH$_2$Cl$_2$ (10 mL), N-iodosuccinimide (0.084 g, 0.37 mmol) provided the vinyl iodide 13 (0.195 g, 0.37 mmol, >99%). $^1$H NMR (250 MHz, CDCl$_3$): δ=6.9-7.1 (m, 4H), 6.2 (s, 1H), 2.4-2.58 (m, 4H), 1.38-1.4 (m, 2H), 1.13-1.3 (m, 10H), 1.02 (s, 6H), 0.79 (m, 12H), 0.41 (q, J=7.6 Hz, 6H); HRMS (EI+): [M]$^+$ calculated for C$_{26}$H$_{45}$OSiI 528.2284. found 528.2293.

Preparation of the (E)-1-alkenylboronate (14)

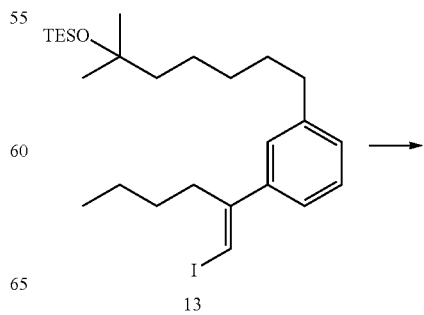

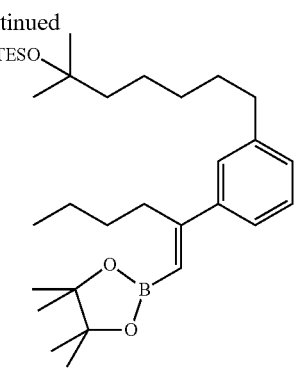

14

Following the process for preparation of (E)-1-alkenyl-boronate (8), using Pd (dppf)Cl$_2$.CH$_2$Cl$_2$ (0.005 g, 0.0061 mmol), KOAc (0.057 g, 0.58 mmol), bis(pinacolato)diborane (0.053 g, 0.21 mmol) vinyl iodide 13 (0.1 g, 0.19 mmol), DMSO (3 mL) provided the vinyl boronic ester 14 (0.086 g, 0.163 mmol, 86%). $^1$H NMR (250 MHz, CDCl$_3$): δ=7.03-7.14 (m, 3H), 6.93 (t, J=6.4 Hz, 1H), 5.47 (s, 1H), 2.73 (t, J=7.2 Hz, 2H), 2.43 (t, J=7.5 Hz, 2H), 1.35-1.57 (m, 3H), 1.14 (s, 12H), 1.02 (s, 6H), 0.67-0.84 (m, 12H), 0.40 (q, J=7.3 Hz, 6H HRMS (EI+): [M]$^+$ calculated for C$_{32}$H$_{57}$BO$_3$Si 528.4170. found 528.4169.

Preparation of the (E)-vinylsilane (15)

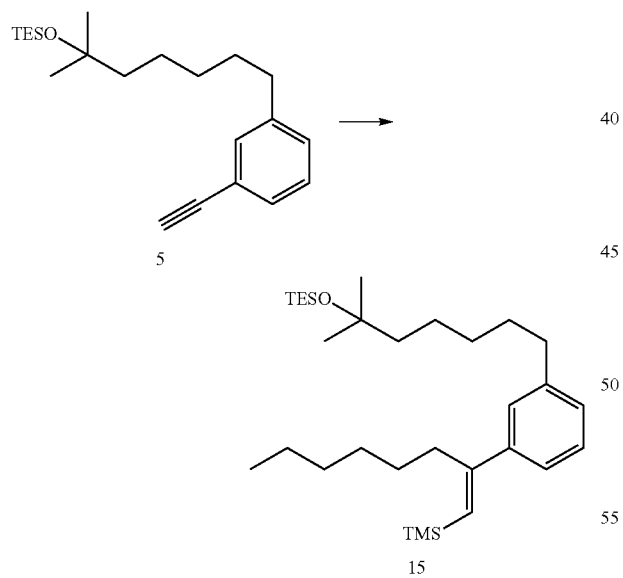

Following the process for preparation of (E)-vinylsilane (6), using anhydrous LiCl (0.236 g, 5.57 mmol), CuI (0.276 g, 2,786 mmol), THF (3 mL), hexylmagnesium bromide in THF (2.8 mL, 5,572 mmol, 2 M), alkyne 5 (0.4 g, 1.16 mmol), HMPA (0.9 mL), THF (5 mL), HMPA (0.3 mL) and TMSCl (0.7 mL, 5.57 mmol) provided the vinylsilane 15 (0.375 g, 0.746 mmol, 64%). $^1$H NMR (250 MHz, CDCl$_3$):

δ=6.8-7.13 (m, 4H), 5.57 (s, 1H), 2.38-2.54 (m, 4H), 1.04 (s, 6H), 0.66-0.87 (m, 12H), 0.42 (q, J=7.5 Hz, 6H), 0.04 (s, 9H); HRMS (CI+): [M+H]$^+$ calculated for C$_{31}$H$_{59}$OSi$_2$ 503.4104. found 503.4107.

Preparation of the (E)-vinyl iodide (16)

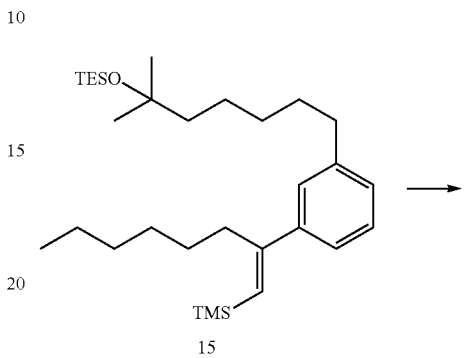

16

Following the process for preparation of (E)-vinyl iodide (7), using vinylsilane 15 (0.28 g, 0.557 mmol), CH$_2$Cl$_2$ (15 mL), N-iodosuccinimide (0.125 g, 0.557 mmol) provided the vinyl iodide 16 (0.26 g, 0.467 mmol, 84%). $^1$H NMR (250 MHz, CDCl$_3$): δ=6.9-7.12 (m, 4H), 6.2 (s, 1H), 2.36-2.58 (m, 4H), 1.35-1.58 (m, 2H), 1.02 (s, 6H), 0.66-0.84 (m, 12H), 0.4 (q, J=7.5 Hz, 6H); HRMS (EI+): [M]$^+$ calculated for C$_{28}$H$_{49}$OSiI 556.2597. found 556.2608.

Preparation of the (E)-1-alkenylboronate (17)

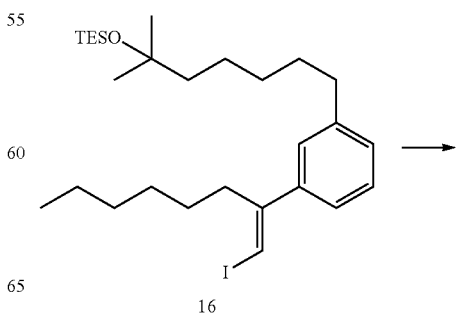

16

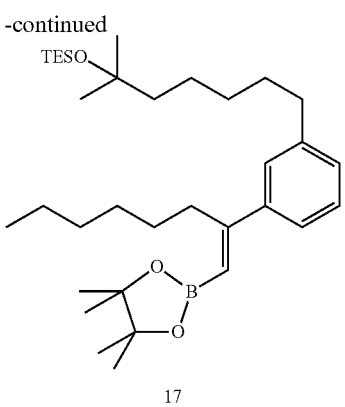

17

Following the process for preparation of (E)-1-alkenyl-boronate (8), using Pd (dppf)Cl$_2$.CH$_2$Cl$_2$ (0.0114 g, 0.014 mmol), KOAc (0.138 g, 1.4 mmol), bis(pinacolato)diborane (0.142 g, 0.56 mmol) vinyl iodide 16 (0.26 g, 0.467 mmol), DMSO (3 mL) provided the vinyl boronic ester 17 (0.156 g, 0.28 mmol, 60%). $^1$H NMR (250 MHz, CDCl$_3$): δ=6.92-7.27 (m, 4H), 5.55 (s, 1H), 2.81 (t, J=7.2 Hz, 2H), 2.5 (t, J=7.5 Hz, 2H), 1.45-1.64 (m, 2H), 1.22 (s, 12H), 1.01 (s, 6H), 0.72-0.92 (m, 12H), 0.48 (q, J=7.5 Hz, 6H); HRMS (EI+): [M]$^+$ calculated for C$_{34}$H$_{61}$BO$_3$Si 556.4483. found 556.4461.

Preparation of the (E)-vinylsilane (18)

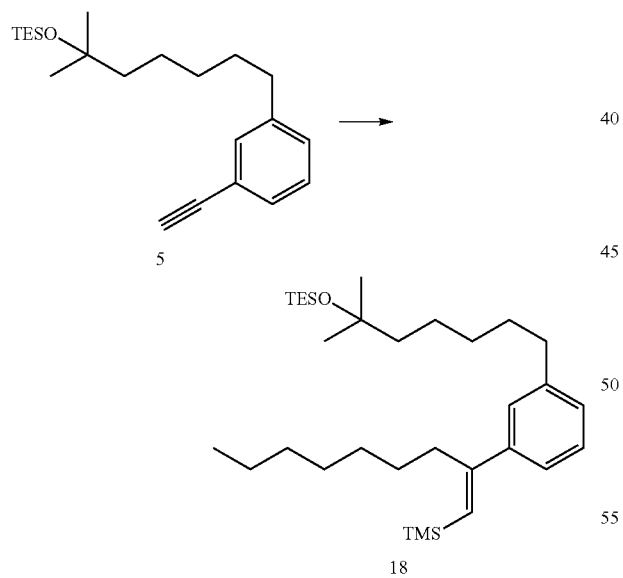

Following the process for preparation of (E)-vinylsilane (6), using anhydrous LiCl (0.233 g, 5.5 mmol), CuI (0.276 g, 2.786 mmol), THF (3 mL), heptylmagnesium bromide in Et$_2$O (5.5 mL, 5.5 mmol, 1M), alkyne 5 (0.4 g, 1.16 mmol), HMPA (1 mL), THF (5 mL), HMPA (0.5 mL) and TMSCl (0.7 mL, 5.57 mmol) provided the vinylsilane 18 (0.506 g, 0.979 mmol, 84%). $^1$H NMR (250 MHz, CDCl$_3$): δ=7.01-7.13 (m, 3H), 6.88-6.98 (m, 1H), 5.58 (s, 1H), 2.38-2.53 (m, 4H), 1.42-1.58 (m, 2H), 1.05 (bs, 6H), 0.67-0.87 (m, 12H), 0.43 (q, J=7.5 Hz, 6H), 0.04 (bs, 9H); HRMS (EI+): [M]$^+$ calculated for C$_{32}$H$_{60}$OSi$_2$ 516.4183. found 516.4180.

Preparation of the (E)-vinyl iodide (19)

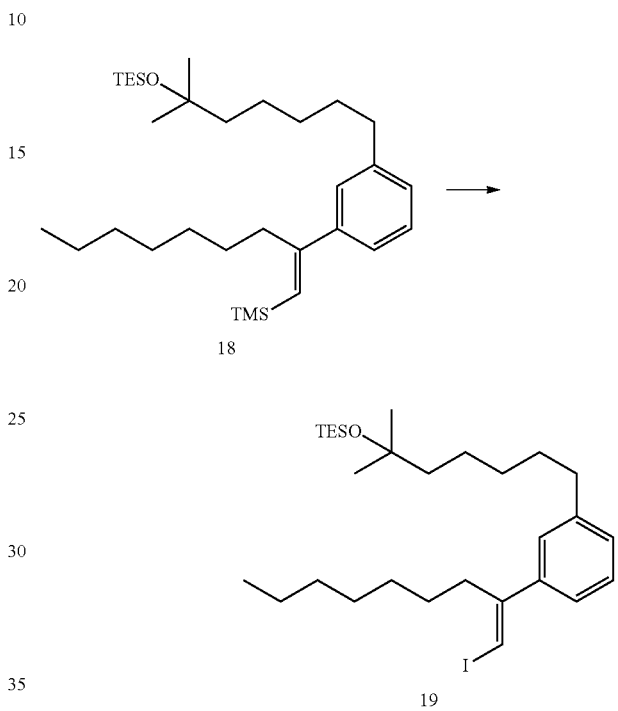

Following the process for preparation of (E)-vinyl iodide (7), using vinylsilane 18 (0.4 g, 0.774 mmol), CH$_2$Cl$_2$ (15 mL), N-iodosuccinimide (0.174 g, 0.774 mmol) provided the vinyl iodide 19 (0.44 g, 0.771 mmol, >99%). $^1$H NMR (250 MHz, CDCl$_3$): δ=7.02-7.13 (m, 1H), 6.89-7.01 (m, 3H), 6.21 (bs, 1H), 2.39-2.59 (m, 4H), 1.40-1.58 (m, 2H), 1.04 (bs, 6H), 0.66-0.86 (m, 12H), 0.41 (q, J=7.5 Hz, 6H); HRMS (EI+): [M]$^+$ calculated for C$_{29}$H$_{51}$IOSi 570.2754. found 570.2755.

Preparation of the (E)-1-alkenylboronate (20)

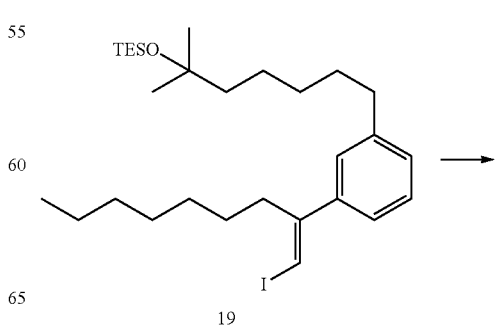

19

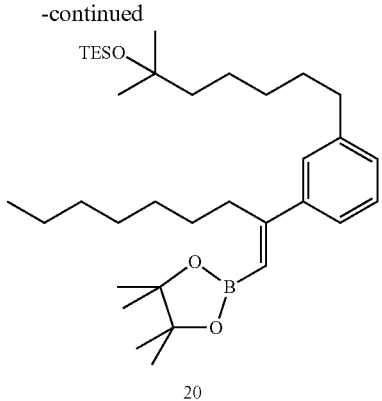

Following the process for preparation of (E)-1-alkenyl-boronate (8), using Pd (dppf)Cl$_2$·CH$_2$Cl$_2$ (0.017 g, 0.021 mmol), KOAc (0.206 g, 2.1 mmol), bis(pinacolato)diborane (0.213 g, 0.84 mmol) vinyl iodide 19 (0.4 g, 0.7 mmol), DMSO (3 mL) provided the vinyl boronic ester 20 (0.343 g, 0.6 mmol, 86%). $^1$H NMR (250 MHz, CDCl$_3$): δ=6.91-7.23 (m, 4H), 5.54 (s, 1H), 2.79 (t, J=7.0 Hz, 2H), 2.49 (t, J=7.3 Hz, 2H), 1.44-1.63 (m, 2H), 1.19 (bs, 12H), 1.08 (bs, 6H), 0.71-0.91 (m, 12H), 0.46 (q, J=7.8 Hz, 6H); HRMS (EI+): [M]$^+$ calculated for C$_{35}$H$_{63}$BO$_3$Si 570.4640. found 570.4641.

Preparation of Vicinal Dibromide (21)

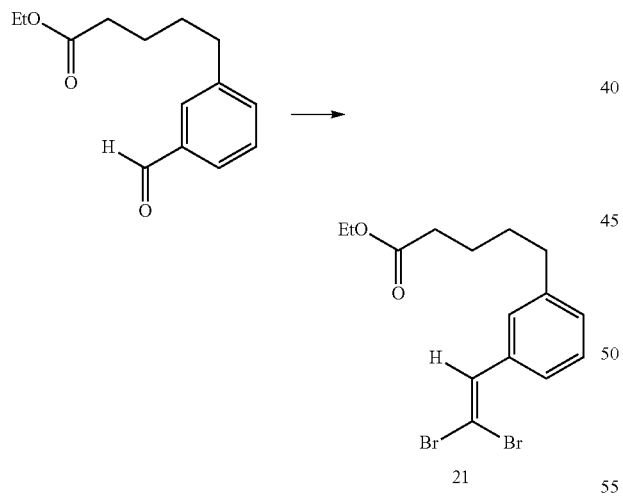

Following the process for preparation of the vicinal dibromide (3), using Ph$_3$P (3.162 g, 12.056 mmol), Zn (0.788 g, 12.056 mmol), CH$_2$Cl$_2$ (40 mL), CBr$_4$ (3.998 g, 12.056 mmol), ethyl 3-formyl-benzenepentanoate (1.13 g, 4,822 mmol), CH$_2$Cl$_2$ (10 mL) provided vicinal dibromide 21 (1,571 g, 4,027 mmol, 84%). $^1$H NMR (250 MHz, CDCl$_3$): δ=7.36 (s, 1H), 7.00-7.32 (m, 4H), 4.02 (q, J=7.1 Hz, 2H), 2.44-2.67 (m, 2H), 2.13-2.33 (m, 2H), 1.48-1.67 (m, 4H), 1.15 (t, J=7.1 Hz, 3H); HRMS (EI+): [M]$^+$ calculated for C$_{15}$H$_{18}$Br$_2$O$_2$ 387.9673. found 387.9673.

Preparation of the Alkyne (22)

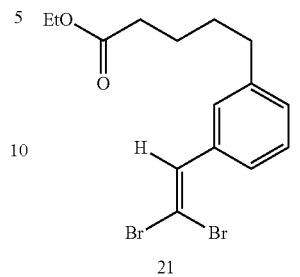

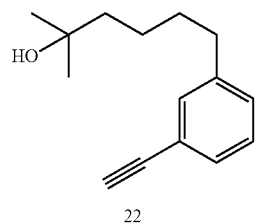

Following the process for preparation of alkyne (4), using MeLi Et$_2$ or (16.1 mL, 24.15 mmol, 1.5 M), germinal dibromide 21 (1.57 g, 4.02 mmol), THF (20 mL); 22 was obtained (0.765 g, 3,536 mmol, 88%). $^1$H NMR (250 MHz, CDCl$_3$): δ=7.03-7.29 (m, 4H), 2.98 (s, 1H), 2.53 (t, J=7.7 Hz, 2H), 1.47-1.61 (m, 2H), 1.22-1.47 (m, 4H), 1.12 (bs, 6H); HRMS (EI+): [M+H]$^+$ calculated for C$_{15}$H$_{20}$O 216.1514. found 216.1517.

Preparation of the Silylether (23)

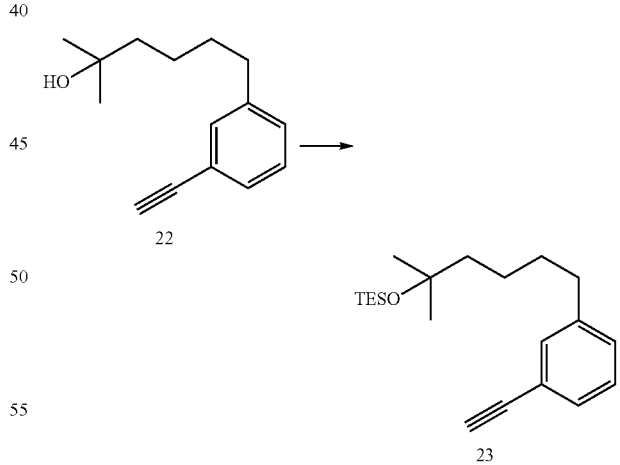

Following the procedure for preparation of silylether (5), using TESOTf (1.1 mL, 4.86 mmol), Et$_3$N (1,345 mL, 9.71 mmol), alkyne 22 (0.7 g, 3.24 mmol), CH$_2$Cl$_2$ (25 mL) provided the silylether 23 (1.023 g, 3,098 mmol, 96%). $^1$H NMR (250 MHz, CDCl$_3$): δ=7.07-7.3 (m, 4H), 2.99 (s, 1H), 2.54 (t, J=7.6 Hz, 2H), 1.46 (m, 2H), 1.13 (s, 6H), 0.88 (t, J=7.8 Hz, 9H), 0.5 (q, J=7.5 Hz, 6H); HRMS (CI+): [M+H]$^+$ calculated for C$_{21}$H$_{35}$OSi 331.2457. found 331.2461.

Preparation of the (E)-vinylsilane (24)

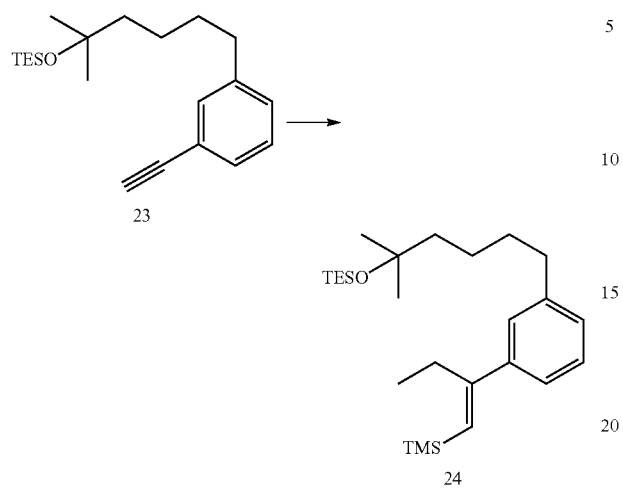

Following the process for preparation of (E)-vinylsilane (6), using LiCl (0.154 g, 3.63 mmol), CuI (0.179 g, 1.82 mmol), THF (3 mL), solution of EtMgBr in THF (1.21 mL, 3.63 mmol, 3M), alkyne 23 (0.25 g, 0.757 mmol), HMPA (0.7 mL), THF (5 mL), HMPA (0.3 mL) and TMSCl (0.46 mL, 3.63 mmol); the vinylsilane 24 was obtained (0.246 g, 0.568 mmol, 75%). $^1$H NMR (250 MHz, CDCl$_3$): δ=7.05-7.17 (m, 3H), 6.19-7.01 (m, 1H), 5.62 (s, 1H), 2.53 (q, J=7.6 Hz, 4H), 1.44-1.59 (m, 2H), 1.06 (s, 6H), 0.78-0.94 (m, 12H), 0.46 (q, J=7.8 Hz, 6H), 0.09 (bs, 6H); HRMS (EI+): [M]$^+$ calculated for C$_{26}$H$_{48}$OSi$_2$ 432.3243. found 432.3247.

Preparation of the (E)-vinyl iodide (25)

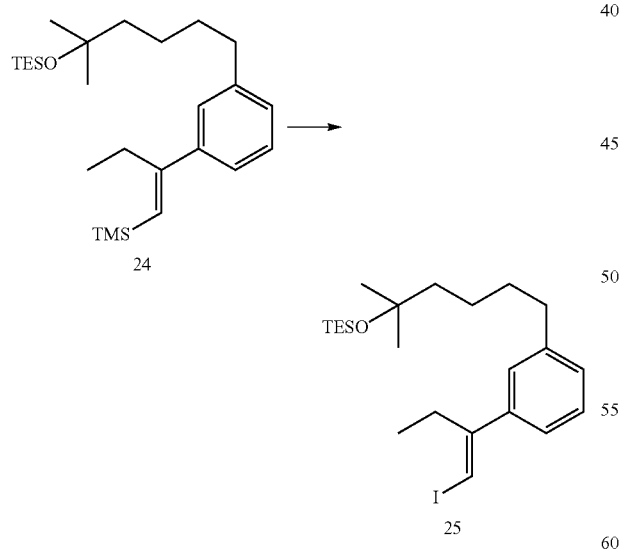

Following the process for preparation of (E)-vinyl iodide (7), using the vinylsilane 24 (0.322 g, 0.744 mmol), CH$_2$Cl$_2$ (20 mL) and N-iodosuccinimide (0.167 g, 0.744 mmol) provided the vinyl iodide 25 (0.322 g, 0.662 mmol, 89%). $^1$H NMR (250 MHz, CDCl$_3$): δ=6.92-7.12 (m, 4H), 6.19 (s, 1H), 2.36-2.64 (m, 4H), 1.37-1.53 (m, 2H), 1.03 (bs, 6H), 0.73-0.89 (m, 12H), 0.40 (q, J=7.9 Hz, 6H); HRMS (EI+): [M]$^+$ calculated for C$_{23}$H$_{39}$OSiI 486.1815. found 486.1822.

Preparation of the (E)-1-alkenylboronate (26)

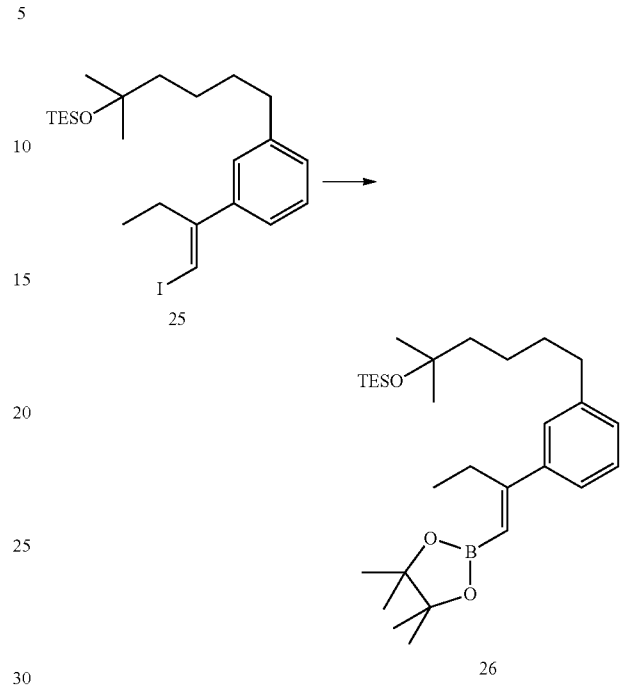

Following the process for preparation of (E)-1-alkenylboronate (8), using Pd (dppf)Cl$_2$.CH$_2$Cl$_2$ (0.0146 g, 0.018 mmol), KOAc (0.182 g, 1.85 mmol), bis(pinacolato)diborane (0.188 g, 0.74 mmol) and solution of vinyl iodide 25 (0.3 g, 0.62 mmol), in DMSO (3 mL); the 1-alkenylboronate 26 was obtained (0.216 g, 0.444 mmol, 72%). $^1$H NMR (250 MHz, CDCl$_3$): δ=6.94-7.24 (m, 4H), 5.53 (s, 1H), 2.81 (q, J=7.4 Hz, 2H), 2.52 (t, J=7.6 Hz, 2H), 1.44-1.59 (m, 2H), 1.21 (bs, 12H), 1.1 (bs, 6H), 0.94 (t, J=7.5 Hz, 3H), 0.85 (t, J=7.8 Hz, 9H), 0.46 (q, J=7.6 Hz, 6H); HRMS (EI+): [M]$^+$ calculated for C$_{29}$H$_{52}$BO$_3$Si 487.3778. found 487.3773.

Preparation of the (E)-vinylsilane (27)

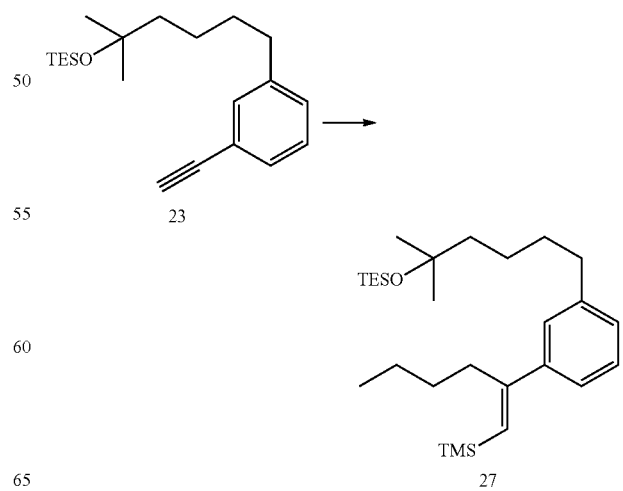

Following the process for preparation of (E)-vinylsilane (6), using LiCl (0.148 g, 3.49 mmol), CuI (0.173 g, 1.74 mmol), THF (3 mL), a solution of BuMgCl in THF (1.74 mL, 3.49 mmol, 2 M), alkyne 23 (0.24 g, 0.73 mmol), HMPA (0.61 mL), THF (5 mL), HMPA (0.3 mL) and TMSCl (0.44 mL, 3.49 mmol) provided the vinylsilane 27 (0.221 g, 0.479 mmol, 66%). $^1$H NMR (250 MHz, CDCl$_3$): δ=7.02-7.15 (m, 3H), 6.9-6.99 (m, 1H), 5.58 (s, 1H), 2.42-2.57 (m, 4H), 1.42-1.57 (m, 2H), 1.06 (bs, 6H), 0.69-0.88 (m, 12H), 0.43 (q, J=7.8, 6H), 0.06 (bs, 9H); HRMS (EI+): [M]$^+$ calculated for C$_{28}$H$_{28}$OSi$_2$ 460.3556. found 460.3552.

Preparation of the (E)-vinyl iodide (28)

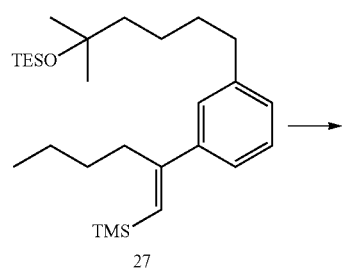

Following the process for preparation of (E)-vinyl iodide (7), using vinylsilane 27 (0.19 g, 0.412 mmol), CH$_2$Cl$_2$ (15 mL), and N-iodosuccinimide (0.093 g, 0.412 mmol); the vinyl iodide 28 was obtained (0.21 g, 0.408 mmol, >99%). $^1$H NMR (250 MHz, CDCl$_3$): δ=6.89-7.11 (m, 4H), 6.19 (s, 1H), 2.4-2.57 (m, 4H), 1.38-1.53 (m, 4H), 1.37-1.53 (m, 2H), 1.03 (bs, 6H), 0.69-0.84 (m, 12H), 0.39 (q, J=7.8 Hz, 6H); HRMS (EI+): [M]$^+$ calculated for C$_{25}$H$_{43}$OSiI 514.2128. found 514.2130.

Preparation of the (E)-1-alkenylboronate (29)

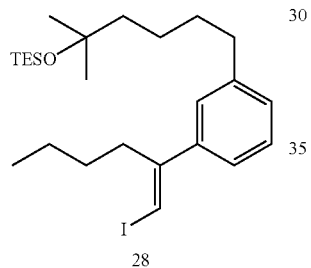

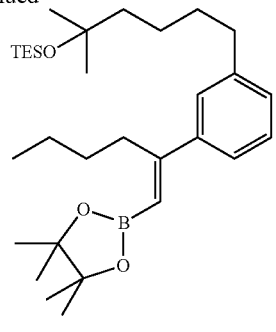

Following the process for preparation of (E)-1-alkenylboronate (8), using Pd (dppf)Cl$_2$.CH$_2$Cl$_2$ (0.0095 g, 0.0116 mmol), KOAc (0.1145 g, 1,167 mmol), bis(pinacolato)diborane (0.1185 g, 0.4668 mmol) and solution of vinyl iodide 28 (0.2 g, 0.389 mmol), in DMSO (2 mL) provided the 1-alkenylboronate 29 (0.144 g, 0.28 mmol, 72%). $^1$H NMR (250 MHz, CDCl$_3$): δ=6.82-7.35 (m, 4H), 5.53 (s, 1H), 2.80 (t, J=7.2 Hz, 2H), 2.49 (t, J=7.6 Hz, 2H), 1.21 (bs, 12H), 1.08 (bs, 6H), 0.69-0.95 (m, 12H), 0.46 (q, J=7.9 Hz, 6H); HRMS (EI+): [M]$^+$ calculated for C$_{31}$H$_{55}$BO$_3$Si 514.4013. found 514.4013.

Preparation of the Ether (30)

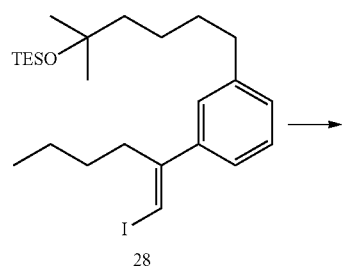

DMAP (0.088 g, 0.72 mmol) and i-Pr$_2$NEt (2.5 mL, 14.35 mmol) were successively added to a solution of 7-bromo-2-methyl-heptan-2-ol (1.5 g, 7.17 mmol) in CH$_2$Cl$_2$ (15 mL) at rt. The reaction mixture was cooled at 0° C. After stirring 15 min at 0° C., MOMCl (1.36 mL, 17.93 mmol) was added dropwise. The reaction mixture was stirred at 0° C. 1 h and then at it for 1.5 h. The reaction was quenched with an aqueous saturated solution of NH$_4$Cl and was extracted with Et$_2$O. The organic phase was dried and concentrated. The residue was purified by flash chromatography and the compound 30 (1.56 g, 6.162 mmol, 86%) was obtained. $^1$H NMR (250 MHz, CDCl$_3$): δ=4.61 (bs, 2H), 3.32 (t, J=6.8 Hz, 2H), 3.27 (bs, 3H), 1.12 (bs, 6H); HRMS (EI+): [M]$^+$ calculated for C$_{10}$H$_{21}$BrO$_2$ 251.0725. found 251.0729.

Preparation of the Grignard Reagent (31)

Anhydrous LiCl (1.67 g, 39.5 mmol) and Mg (1.2 g, 49.37 mmol) were dried in a reaction tube for 12 h at 110° C. under vacuum. THF (20 mL) was added and was stirred for 5 min at rt. The Mg was activated with a few drops of dibromoethane. A solution of compound 30 (5 g, 19.75 mmol) in THF (14 mL) was added to the mixture via cannula. The mixture was stirred vigorously for 3 h at rt. The solution of the Grignard reagent 31 was transferred, with care not to stir the excess Mg into a dry flask via cannula.

Preparation of the (E)-vinylsilane (32)

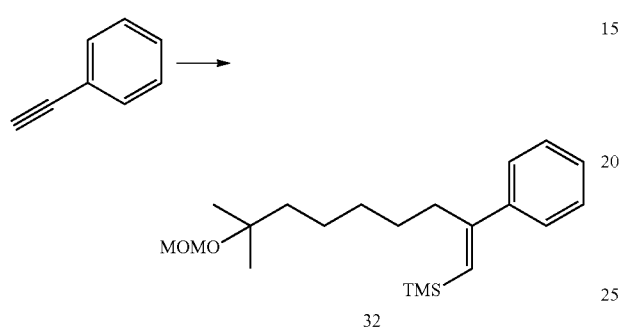

32

Following the process for preparation of (E)-vinylsilane (6), using LiCl (0.149 g, 3.50 mmol), CuI (0.349 g, 3.52 mmol), THF (3 mL), a solution of 31 in THF (14.68 mL, 8.81 mmol, 0.6M), phenylacetylene (0.15 g, 1.468 mmol), HMPA (1.2 mL), THF (5 mL), HMPA (0.6 mL) and TMSCl (0.46 mL, 3.67 mmol) provided the vinylsilane 32 (0.358 g, 1.027 mmol, 70%). $^1$H NMR (250 MHz, CDCl$_3$): δ=7.04-7.25 (m, 5H), 5.60 (s, 1H), 4.55 (s, 2H), 3.20 (s, 3H), 2.48 (t, J=7.2 Hz, 2H), 1.05 (bs, 6H), 0.07 (bs, 9H); HRMS (EI+): [M]$^+$ calculated for C$_{21}$H$_{36}$O$_2$Si 348.2485. found 348.2488.

Preparation of the (E)-vinyl iodide (33)

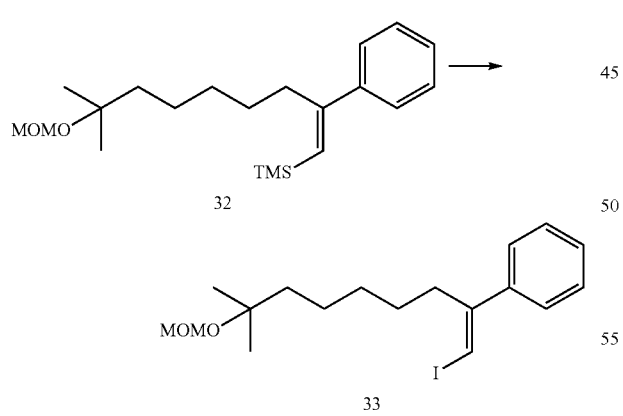

33

Following the process for preparation of (E)-vinyl iodide (7), using the vinylsilane 32 (0.35 g, 1,004 mmol), CH$_2$Cl$_2$ (15 mL) and N-iodosuccinimide (0.226 g, 1.01 mmol) provided the vinyl iodide 33 (0.343 g, 0.853 mmol, 85%). $^1$H NMR (250 MHz, CDCl$_3$): δ=7.19-7.25 (m, 5H), 6.32 (bs, 1H), 4.62 (bs, 2H), 3.28 (bs, 3H), 2.63 (t, J=7.4 Hz, 2H), 1.13 (bs, 6H); HRMS (EI+): [M]$^+$ calculated for C$_{18}$H$_{27}$O$_2$I 402.1056. found 402.1056.

Preparation of the (E)-1-alkenylboronate (34)

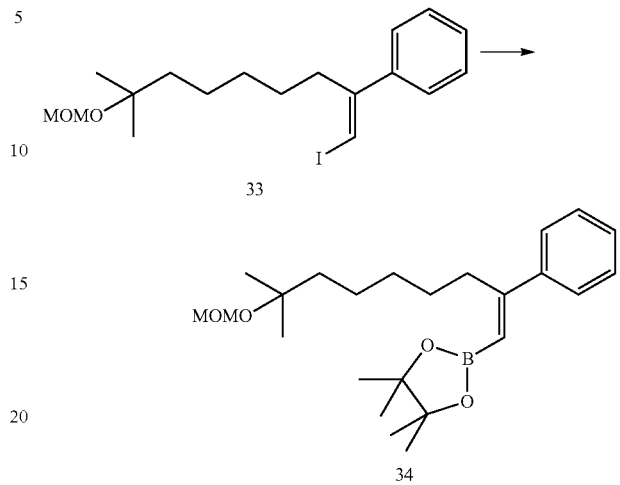

34

Following the process for preparation of (E)-1-alkenylboronate (8), using Pd (dppf)Cl$_2$.CH$_2$Cl$_2$ (0.017 g, 0.0212 mmol), KOAc (0.207 g, 2,117 mmol), bis(pinacolato)diborane (0.215 g, 0.847 mmol) and a solution of vinyl iodide 33 (0.285 g, 0.708 mmol), in DMSO (2 mL); the 1-alkenylboronate 34 was obtained (0.22 g, 0.547 mmol, 77%). $^1$H NMR (250 MHz, CDCl$_3$): δ=7.18-7.29 (m, 2H), 7.02-7.18 (m, 3H), 5.44 (bs, 1H), 4.48 (bs, 2H), 3.14 (bs, 3H), 2.71 (t, J=7.2 Hz, 2H), 1.11 (bs, 12H), 0.99 (bs, 6H); HRMS (EI+): [M]$^+$ calculated for C$_{24}$H$_{39}$BO$_4$ 402.2941. found 402.2944.

Preparation of the (E)-vinylsilane (35)

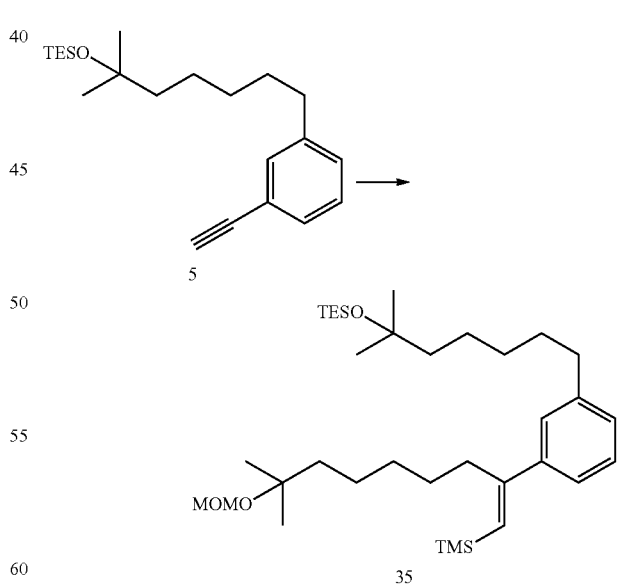

35

Following the process for preparation of (E)-vinylsilane (6), using LiCl (0.074 g, 1,741 mmol), CuI (0.1724 g, 1,741 mmol), THF (3 mL), a solution of 31 in THF (7.25 mL, 4.35 mmol, 0.6 M), the alkyne 5 (0.25 g, 0.725 mmol), HMPA (0.8 mL), THF (5 mL), HMPA (0.4 mL) and TMSCl (0.23 mL, 1.81 mmol) provided the vinylsilane 35 (0.384 g, 0.649 mmol, 89%). ¹H NMR (250 MHz, CDCl₃): δ=7.15-7.25 (m, 3H), 7.04-7.11 (m, 1H), 5.71 (bs, 1H), 4.71 (bs, 2H), 3.37 (bs, 3H), 2.61 (t, J=7.7 Hz, 4H), 1.57-1.73 (m, 2H), 1.21 (bs, 6H), 1.19 (bs, 3H), 1.18 (bs, 3H), 0.95 (t, J=7.8 Hz, 9H), 0.57 (q, J=7.6 Hz, 6H), 0.19 (bs, 9H); HRMS (EI+): [M]⁺ calculated for $C_{35}H_{66}O_3Si_2$ 590.4550. found 590.4557.

Preparation of the (E)-vinyl iodide (36)

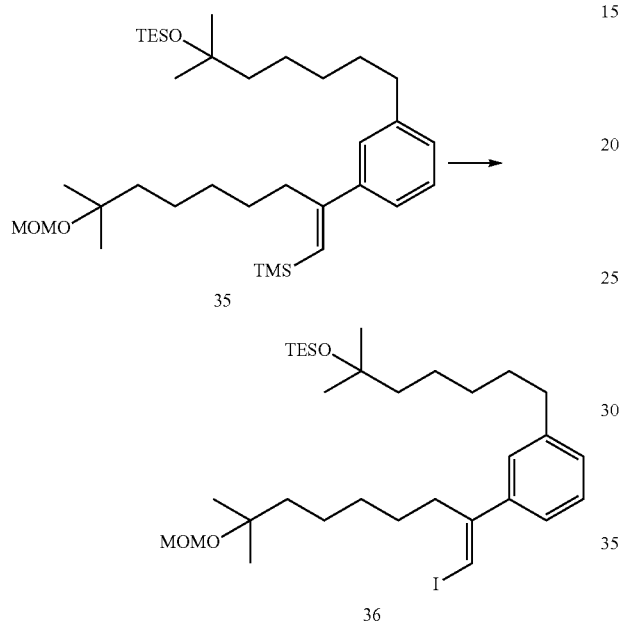

Following the process for preparation of (E)-vinyl iodide (7), using vinylsilane 35 (0.3 g, 0.5075 mmol), CH₂Cl₂ (10 mL), and N-iodosuccinimide (0.114 g, 0.5075 mmol); the vinyl iodide 36 was obtained (0.248 g, 0.385 mmol, 76%). ¹H NMR (250 MHz, CDCl₃): δ=7.07-7.25 (m, 4H), 6.38 (bs, 1H), 4.71 (bs, 2H), 3.36 (bs, 3H), 2.57-2.76 (m, 4H), 1.58-1.73 (m, 2H), 1.21 (bs, 12H), 0.97 (t, J=7.8 Hz, 9H), 0.59 (q, J=8.4 Hz, 6H); HRMS (EI+): [M]⁺ calculated for $C_{32}H_{57}IO_3Si$ 644.3122. found 644.3125.

Preparation of the (E)-1-alkenylboronate (37)

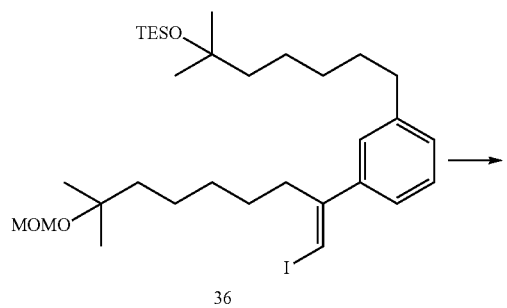

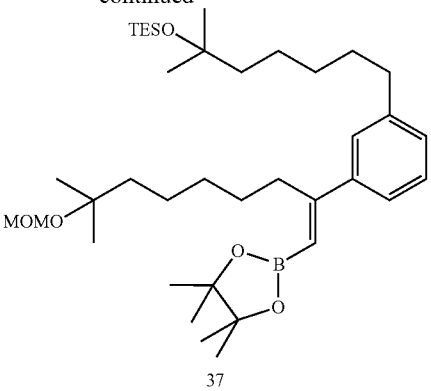

Following the process for preparation of (E)-1-alkenyl-boronate (8), using Pd (dppf)Cl₂CH₂Cl₂ (0.008 g, 0.0093 mmol), KOAc (0.0912 g, 0.93 mmol), bis(pinacolato)dibo-rane (0.0945 g, 0.372 mmol) and a solution of vinyl iodide 36 (0.2 g, 0.31 mmol), in DMSO (3 mL); the 1-alkenylbo-ronate 37 was obtained (0.127 g, 0.197 mmol, 64%). ¹H NMR (250 MHz, CDCl₃): δ=7.05-7.3 (m, 4H), 5.62 (bs, 1H), 4.67 (bs, 2H), 3.33 (bs, 3H), 2.88 (t, J=7.1 Hz, 2H), 2.58 (t, J=7.6 Hz, 2H), 1.53-1.73 (m, 2H), 1.29 (bs, 12H), 1.17 (bs, 12H), 0.94 (t, J=7.8 Hz, 9H), 0.55 (q, J=7.8 Hz, 6H); HRMS (EI+): [M]⁺ calculated for $C_{38}H_{69}BO_5Si$ 644.5007. found 644.5007.

Preparation of the Ester (38)

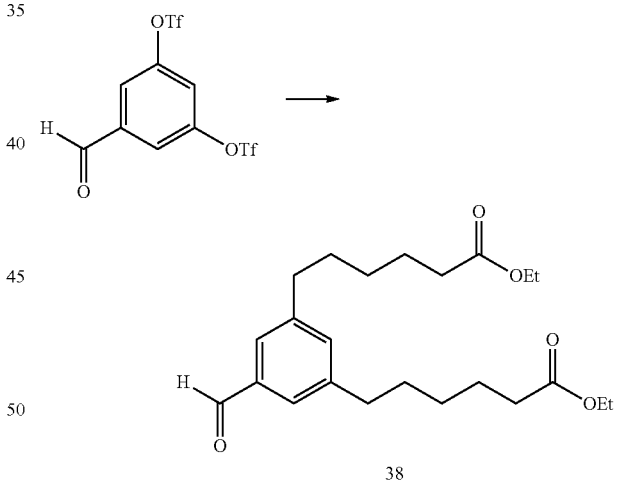

Pd(OAc)₂ (0.0145 g, 0.065 mmol) and S-Phos (0.053 g, 0.129 mmol) were stirred in dioxane (3 mL) for 15 min at rt. A solution of 5-formyl-1,3-phenylene trifluoromethane-sulfonate, (1.3 g, 3.23 mmol) in dioxane (7 mL) and a solution of the organozincate compound 31 in THF (13 mmol) were added successively The reaction mixture was stirred for 30 min at rt and then quenched with NH₄Cl (aq. sat.). The mixture was extracted with Et₂O. The organic phase was dried and concentrated. The residue was purified by flash chromatography the ester 38 (0.964 g, 2.469 mmol, 76%) was obtained. ¹H NMR (250 MHz, CDCl₃): δ=9.9 (s, 1H), 7.45 (d, J=1.5 Hz, 2H), 7.19 (bs, 1H), 4.05 (q, J=7.1 Hz, 4H), 2.6 (t, J=7.7 Hz, 4H), 2.24 (t, J=7.4 Hz, 4H), 1.53-1.68

(m, 8H), 1.24-1.39 (m, 4H), 1.18 (t, J=7.1 Hz, 6H); HRMS (EI+): [M]+ calculated for C23H34O5 390.2406. found 390.2410.

Preparation of the (E)-vinyl iodide (39)

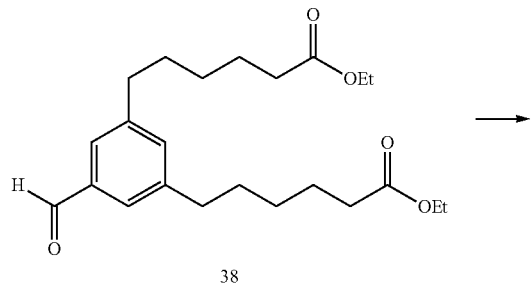

38

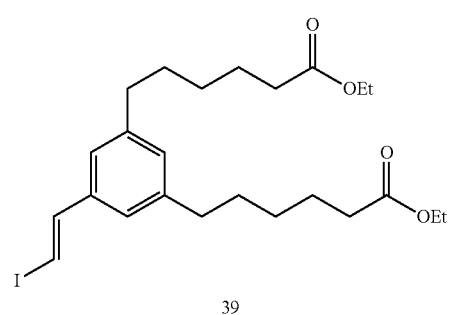

39

Anhydrous CrCl2 (0.567 g, 4.61 mmol) was suspended in THF (10 mL) under argon. A solution of the alkdehyde 38 (0.3 g, 0.768 mmol) and iodoform (0.605 g, 1.536 mmol) in THF (5 mL) was added dropwise to the suspension at 0° C. After stirring 4 h at 0° C., the reaction mixture was poured into water and extracted with Et2O. The organic phase was dried and concentrated. The residue was purified by flash chromatography and the vinyl iodine 39 (0.296 g, 0.575 mmol, 75%) (E/Z=14/1)] was obtained. 1H NMR (250 MHz, CDCl3): δ=7.37 (d, J=14.9 Hz, 1H), 6.91 (bs, 3H), 6.79 (d, J=14.9 Hz, 1H), 4.11 (q, J=7.1 Hz, 4H), 2.56 (t, J=7.7 Hz, 4H), 2.28 (t, J=7.5 Hz, 4H), 1.53-1.75 (m, 8H), 1.29-1.43 (m, 4H), 1.24 (t, J=7.1 Hz, 6H); HRMS (EI+): [M]+ calculated for O24H35O4I 514.1580. found 514.1577.

Preparation of the (E)-1-alkenylboronate (40)

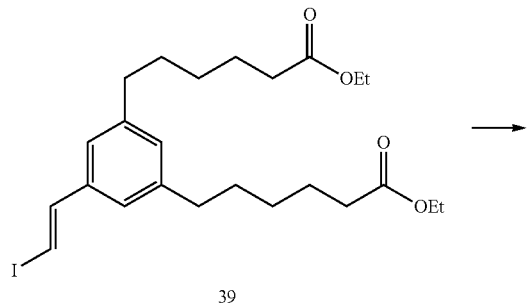

39

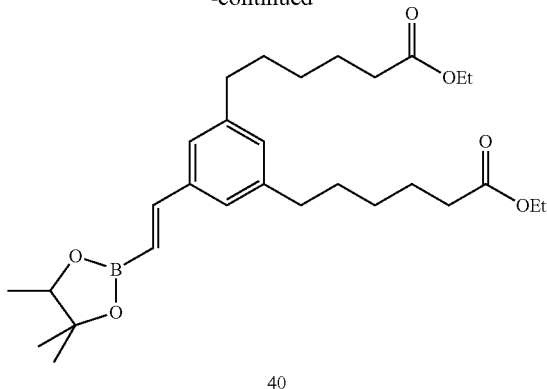

40

Following the process for preparation of (E)-1-alkenyl-boronate (8), using Pd (dppf)Cl2.CH2Cl2 (0.012 g, 0.0146 mmol), KOAc (0.143 g, 1,458 mmol), bis(pinacolato)diborane (0.185 g, 0.729 mmol) and a solution of vinyl iodide 39 (0.25 g, 0.486 mmol), in DMSO (3 mL); the vinylboronic ester 40 was obtained (0.17 g, 0.33 mmol, 68%). 1H NMR (250 MHz, CDCl3): δ=7.31 (d, J=18.4 Hz, 1H), 7.06 (d, J=1.1 Hz, 2H), 6.86 (bs, 1H), 6.08 (d, J=18.4 Hz, 1H), 4.06 (q, J=7.1 Hz, 4H), 2.52 (t, J=7.6 Hz, 4H), 2.23 (t, J=7.5 Hz, 4H), 1.48-1.68 (m, 8H), 1.25 (bs, 12H), 1.18 (t, J=7.1 Hz, 6H); HRMS (EI+): [M]+ calculated for O30H47BO6 514.3466. found 514.3470.

Example 1 Preparation of Triol (42)—Code PG-136p

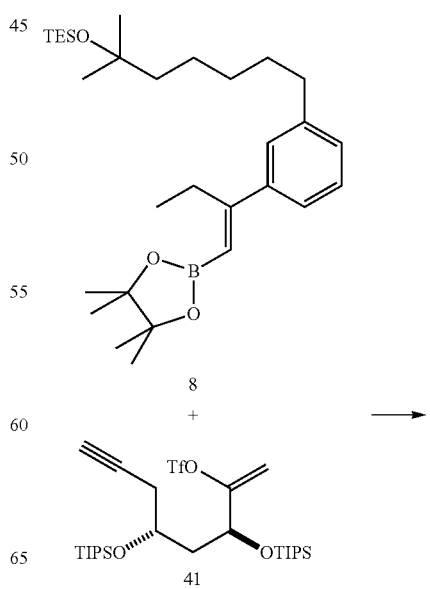

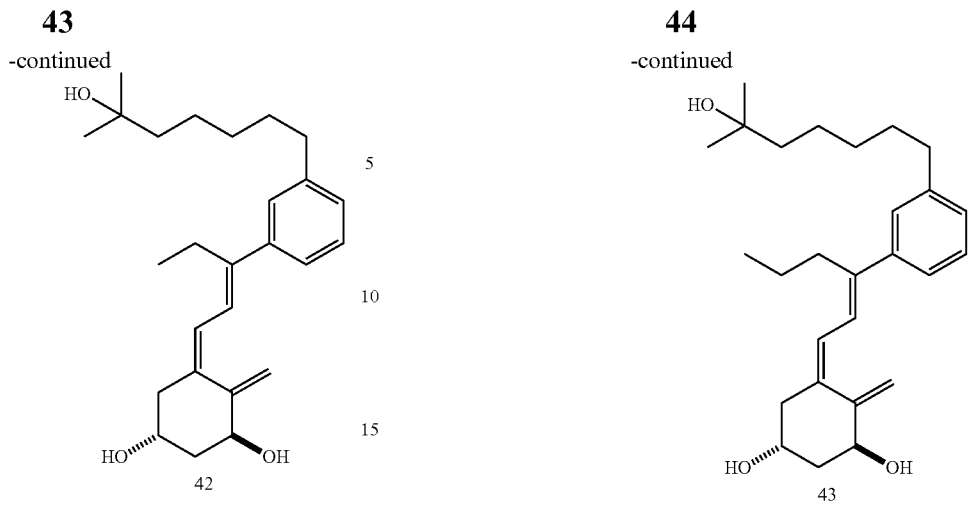

K₃PO₄ (3 mL, 2M aq.) and (Ph₃P)₂PdCl₂ (0.007 g, 0.01 mmol) were successively added to a solution of boronic ester 8 (0.1 g, 0.2 mmol) and enol triflate 41a (0.14 g, 0.233 mmol) in THF (10 mL). The mixture was stirred vigorously for 1.5 h at rt. The reaction mixture was diluted with H₂O and extracted with Et₂O. The organic phase was dried and concentrated. The residue was purified by flash chromatography to yield the protected compound, which was dissolved in THF (5 mL). A solution of TBAF in THF (1.2 mL, 1.2 mmol, 1M) was added. The reaction mixture was stirred for 24 h at rt and then diluted with NH₄Cl (aq. sat). The mixture was extracted with EtOAc. The organic phase was dried and concentrated. The residue was purified by flash chromatography to give the triol 42 (0.053 g, 0.133 mmol, 67%). ¹H NMR (250 MHz, CDCl₃): δ=6.99-7.24 (m, 4H), 6.66 (d, J=11.4 Hz, 1H), 6.43 (d, J=11.4 Hz, 1H), 5.35 (bs, 1H), 5.03 (bs, 1H), 4.45 (t, J=5.7 Hz, 1H), 4.17-4.29 (m, 1H), 2.51-2.73 (m, 5H), 2.37 (q, J₁=7.0 Hz, J₂=13.3 Hz, 1H), 1.97 (t, J=5.5 Hz, 2H), 1.55-1.73 (m, 3H), 1.19 (bs, 6H), 1.06 (t, J=7.5 Hz, 3H); HRMS (EI+): [M]⁺ calculated for C₂₆H₃₈O₃ 398.2820. found 398.2819; [α]_D²⁵=+19.1° (c=1.2 in EtOH).

Example 2 Preparation of Triol (43)—Code PG-152

Following the preparation procedure of triol (42) using K₃PO₄ (3 mL, 2M aq), (Ph₃P)₂PdCl₂ (0.0116 g, 0.0165 mmol), a solution of boronic ester 11 (0.17 g, 0.33 mmol) and of enol triflate 41 (0.252 g, 0.419 mmol) in THF (10 mL), THF (5 mL) and a solution of TBAF in THF (1.98 mL, 1.98 mmol, 1M) the triol 43 (0.095 g, 0.23 mmol, 70%) was obtained. ¹H NMR (250 MHz, CDCl₃): δ=6.98-7.24 (m, 4H), 6.68 (d, J=11.4 Hz, 1H), 6.42 (d, J=11.3 Hz, 1H), 5.34 (bs, 1H), 5.04 (bs, 1H), 4.45 (t, J=5.6 Hz, 1H), 4.16-4.29 (m, 1H), 2.50-2.72 (m, 5H), 2.37 (q, J₁=7.0 Hz, J₂=13.3 Hz, 1H), 1.97 (t, J=5.5 Hz, 2H), 1.53-1.72 (m, 3H), 1.19 (bs, 6H), 0.92 (t, J=7.3 Hz, 3H); HRMS (EI+): [M]⁺ calculated for C₂₇H₄₀O₃ 412.2977. found 412.2979; [α]_D²⁵=+18.9° (c=1.7 in EtOH).

Example 3 Preparation of Triol (44)—Code PG-128

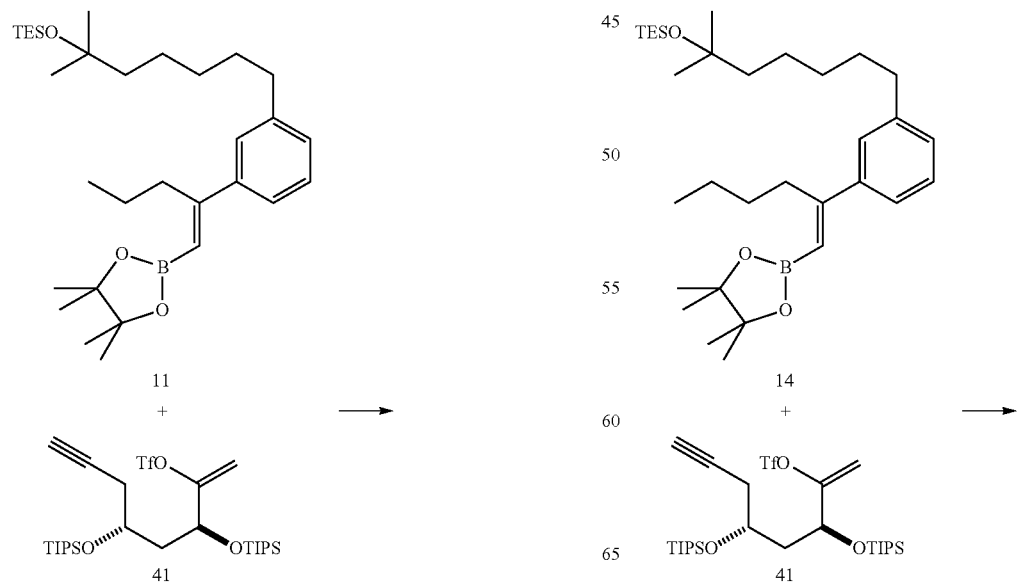

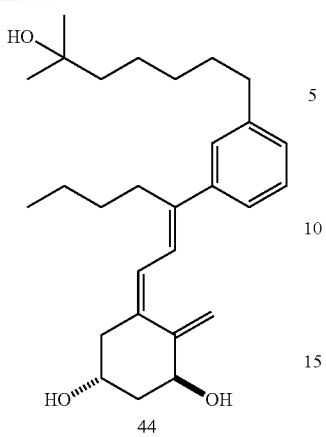

44

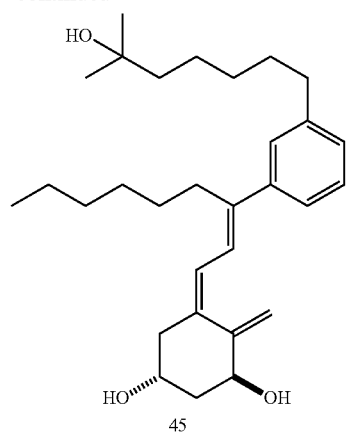

45

Following the preparation procedure of triol (42) using K$_3$PO$_4$ (3 mL, 2M aq), (Ph$_3$P)$_2$PdCl$_2$ (0.0066 g, 0.0094 mmol), a solution of boronic ester 14 (0.1 g, 0.189 mmol) and enol triflate 41 (0.167 g, 0.278 mmol) in THF (10 mL), THF (5 mL) and a solution of TBAF in THF (1,134 mL, 1,134 mmol, 1M) provided the triol 44 (0.061 g, 0.143 mmol, 76%). $^1$H NMR (400 MHz, CDCl$_3$): δ=7.00-7.24 (m, 4H), 6.66 (d, J=11.4 Hz, 1H), 6.42 (d, J=11.5 Hz, 1H), 5.35 (bs, 1H), 5.04 (bs, 1H), 4.46 (t, J=5.7 Hz, 1H), 4.2-4.3 (m, 1H), 2.53-2.73 (m, 5H), 2.38 (q, J$_1$=7.1 Hz, J$_2$=13.3 Hz, 1H), 1.98 (t, J=5.4 Hz, 2H), 1.54-1.72 (m, 3H), 1.19 (bs, 6H), 0.89 (t, J=6.8 Hz, 3H); HRMS (EI+): [M]$^+$ calculated for C$_{28}$H$_{42}$O$_3$ 426.3133. found 426.3127; [α]$_D^{25}$=+14.2° (c=1.1 in EtOH).

Following the preparation procedure of triol (42) using K$_3$PO$_4$ (3 mL, 2M aq), (Ph$_3$P)$_2$PdCl$_2$ (0.0063 g, 0.009 mmol), a solution of boronic ester 17 (0.1 g, 0.179 mmol) and enol triflate 41 (0.107 g, 0.179 mmol) in THF (10 mL), THF (5 mL) and a solution of TBAF in THF (1.07 mL, 1.07 mmol, 1 M) the triol 45 (0.055 g, 0.121 mmol, 68%) was obtained. $^1$H NMR (500 MHz, CDCl$_3$): δ=7.14-7.24 (m, 3H), 7.04 (d, J=7.3 Hz, 1H), 6.66 (d, J=11.4 Hz, 1H), 6.43 (d, J=11.3 Hz, 1H), 5.36 (bs, 1H), 5.05 (bs, 1H), 4.46 (t, J=5.7 Hz, 1H), 4.23-4.29 (m, 1H), 2.56-2.72 (m, 5H), 2.38 (q, J$_1$=7.0 Hz, J$_2$=13.3 Hz, 1H), 1.99 (t, J=5.3 Hz, 2H), 1.57-1.70 (m, 3H), 1.2 (bs, 6H), 0.86 (t, J=6.9 Hz, 3H); [M]$^+$ calculated for C$_{30}$H$_{46}$O$_3$ 454.3446. found 454.3448; [α]$_D^{25}$=+20.0° (c=1.3 in EtOH).

Example 4 Preparation of Triol (45)—Code PG-156

Example 5 Preparation of Triol (46)—Code PG-403

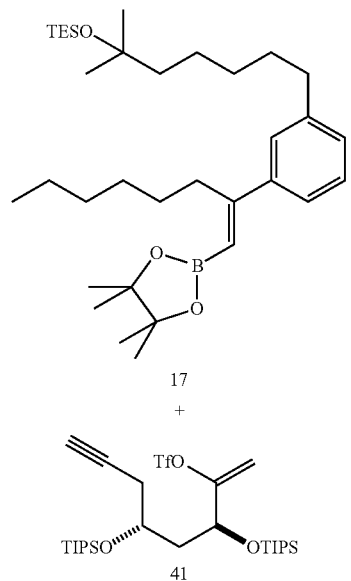

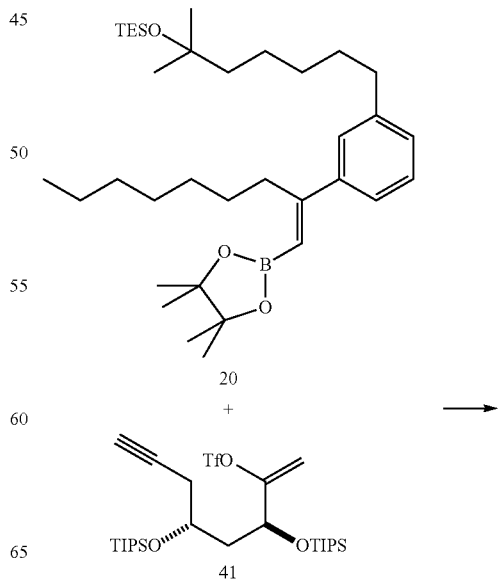

47

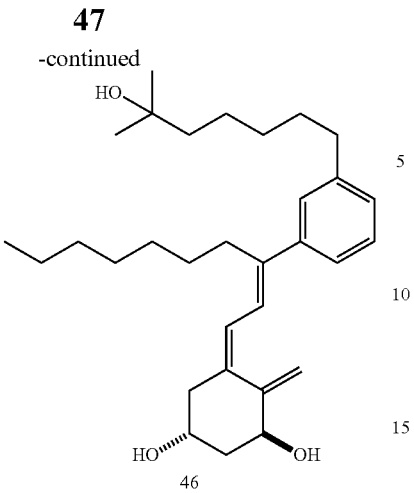

46

48

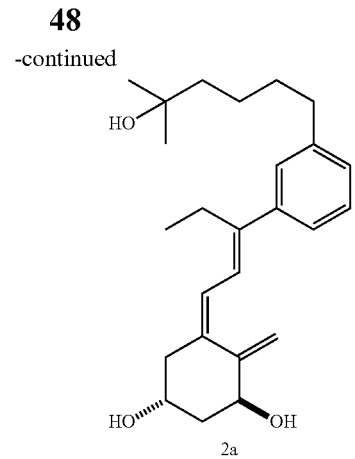

2a

Following the preparation procedure of triol (42) using K₃PO₄ (4.5 mL, 2M aq), (Ph₃P)₂PdCl₂ (0.012 g, 0.0175 mmol), a solution of boronic ester 20 (0.2 g, 0.35 mmol) and enol triflate 41 (0.252 g, 0.42 mmol) in THF (10 mL), THF (5 mL) and a solution of TBAF in THF (2.1 mL, 2.1 mmol, 1M) the triol 46 (0.129 g, 0,275 mmol, 79%) was obtained. $^1$H NMR (250 MHz, CDCl₃): δ=6.99-7.24 (m, 4H), 6.66 (d, J=11.4 Hz, 1H), 6.42 (d, J=11.4 Hz, 1H), 5.35 (bs, 1H), 5.04 (bs, 1H), 4.45 (t, J=5.5 Hz, 1H), 4.16-4.32 (m, 1H), 2.53-2.74 (m, 5H), 2.37 (q, J₁=6.9 Hz, J₂=13.3 Hz, 1H), 1.97 (t, J=5.4 Hz, 2H), 1.54-1.72 (m, 3H), 1.19 (bs, 6H), 0.87 (t, J=6.6 Hz, 3H); HRMS (EI+): [M]⁺ calculated for C₃₁H₄₈O₃ 468.3603. found 468.3606; [α]$_D^{25}$=+21.7° (c=0.3 in EtOH).

Following the preparation procedure of triol (42) using K₃PO₄ (3 mL, 2M aq), (Ph₃P)₂PdCl₂ (0.0094 g, 0.0134 mmol), a solution of boronic ester 26 (0.13 g, 0.267 mmol) and enol triflate 41 (0.204 g, 0.339 mmol) in THF (10 mL), THF (5 mL) and a solution of TBAF in THF (1.6 mL, 1.6 mmol, 1 M) the triol 47 (0.069 g, 0.179 mmol, 67%) was obtained. $^1$H NMR (250 MHz, CDCl₃): δ=7.15-7.23 (m, 3H), 6.99-7.08 (m, 1H), 6.66 (d, J=11.4 Hz, 1H), 6.41 (d, J=11.4 Hz, 1H), 5.32 (bs, 1H), 5.02 (bs, 1H), 4.43 (t, J=5.4 Hz, 1H), 4.15-4.27 (m, 1H), 2.54-2.75 (m, 6H), 2.35 (q, J₁=7.2 Hz, J₂=13.2 Hz, 1H), 1.91-2.0 (m, 2H), 1.18 (bs, 6H), 1.04 (t, J=7.5 Hz, 3H); HRMS (EI+): [M]⁺ calculated for C₂₅H₃₆O₃ 384.2664. found 384.2654; [α]$_D^{25}$=+17.1° (c=0.15 in EtOH).

Example 6 Preparation of Triol (47)—Code PG-149

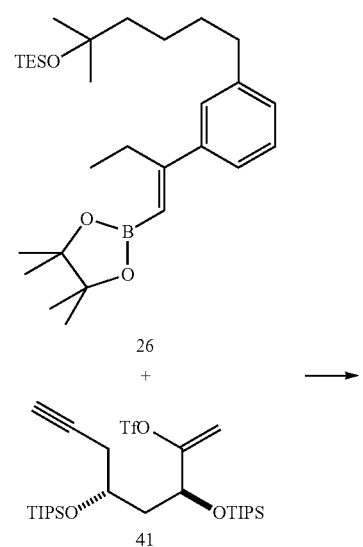

26
+
41

Example 7 Preparation of Triol (48)—Code PG-141

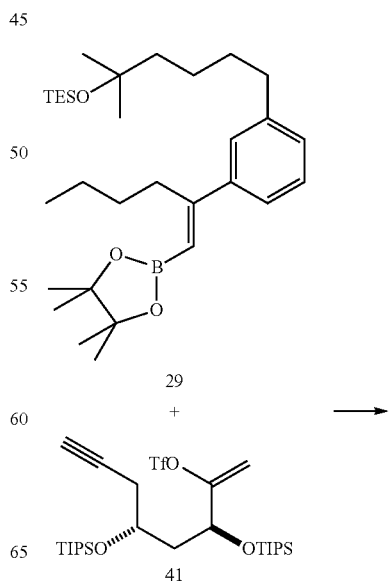

29
+
41

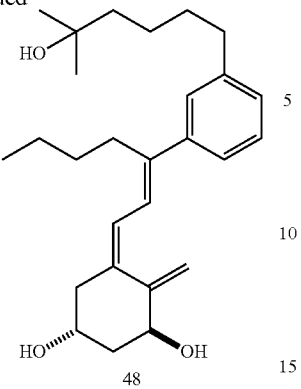

48

Following the preparation procedure of triol (42) using K$_3$PO$_4$ (3 mL, 2M aq), (Ph$_3$P)$_2$PdCl$_2$ (0.0068 g, 0.0097 mmol), a solution of boronic ester 29 (0.1 g, 0.194 mmol) and enol triflate 41 (0.171 g, 0.284 mmol) in THF (10 mL), THF (5 mL) and a solution of TBAF in THF (1.16 mL, 1.16 mmol, 1M) the triol 48 (0.053 g, 0.128 mmol, 66%) was obtained. $^1$H NMR (400 MHz, CDCl$_3$): δ=7.01-7.07 (m, 3H), 7.04 (d, J=6.8 Hz), 6.66 (d, J=11.3 Hz, 1H), 6.43 (d, J=11.3 Hz, 1H), 4.45 (t, J=4.9 Hz, 1H), 4.25 (bs, 1H), 2.58-2.71 (m, 5H), 2.51 (t, J=7.4 Hz, 1H), 2.37 (q, J$_1$=7.1 Hz, J$_2$=13.1 Hz, 1H), 1.89-2.07 (m, 3H), 1.57-1.69 (m, 3H), 1.19 (bs, 6H), 0.89 (t, J=6.7 Hz, 3H); HRMS (EI+): [M]$^+$ calculated for C$_{27}$H$_{40}$O$_3$ 412.2977. found 412.2969; [α]$_D^{25}$=+17.1° (c=1.5 in EtOH).

Example 8 Preparation of Tetraol (49)—Code PG-385

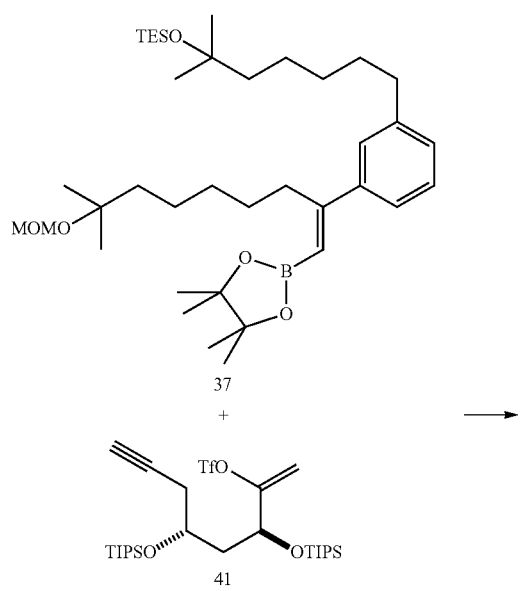

37
+
41

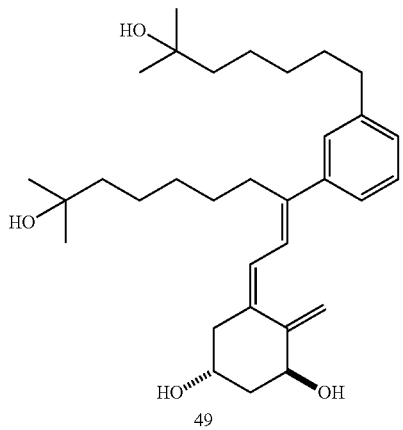

49

K$_3$PO$_4$ (2 mL, 2M aq.) and (Ph$_3$P)$_2$PdCl$_2$ (0.0054 g, 0.008 mmol) were successively added to a solution of boronic ester 37 (0.1 g, 0.155 mmol) and enol triflate 41 (0.112 g, 0.186 mmol) in THF (2 mL). The mixture was stirred vigorously for 2 h at rt. The reaction mixture was diluted with H$_2$O and extracted with Et$_2$O. The organic phase was dried and concentrated. The residue was purified by flash chromatography to yield the protected compound, which was dissolved in THF (5 mL). A solution of TBAF in THF (0.93 mL, 0.93 mmol, 1M) was added. The reaction mixture was stirred for 12 h at rt and then diluted with NH$_4$Cl (aq. sat). The mixture was extracted with EtOAc. The organic phase was dried and concentrated. The residue was purified by flash chromatography to obtain the protected compound, which was dissolved in THF (10 mL). The resin AG50W-X4 (3 g, wet weight, freshly washed with MeOH) was added and the resin mixture was stirred for 10 h at rt. The mixture was filtered and washed several times with EtOAc. The solution was evaporated in vacuo and the residue was purified by flash chromatography to provide the triol 49 (0.041 g, 0.0822 mmol, 53%). $^1$H NMR (400 MHz, CD$_3$OD): δ=7.12-7.17 (m, 3H), 6.98-7.02 (m, 1H), 6.71 (d, J=11.3 Hz, 1H), 6.40 (d, J=11.3 Hz, 1H), 5.33 (bs, 1H), 4.94 (d, J=2 Hz, 1H), 4.39 (q, J$_1$=4.5 Hz, J$_2$=6.6 Hz, 1H), 4.14 (m, 1H), 3.27-3.29 (m, 1H), 2.65 (t, J=7.4 Hz, 2H), 2.54-2.62 (m, 3H), 2.32 (q, J$_1$=7.2 Hz, J$_2$=13.2 Hz, 1H), 1.83-1.97 (m, 2H), 1.55-1.66 (m, 2H), 1.13 (bs, 6H), 1.12 (bs, 6H); HRMS (EI+): [M]$^+$ calculated for C$_{32}$H$_{50}$O$_4$ 498.3709. found 498.3691; [α]$_D^{25}$=+11.7° (c=1.15 in EtOH).

Example 9 Preparation of Triol (50)—Code PG-366

Example 10 Preparation of Tetraol (51)—Code PG-433

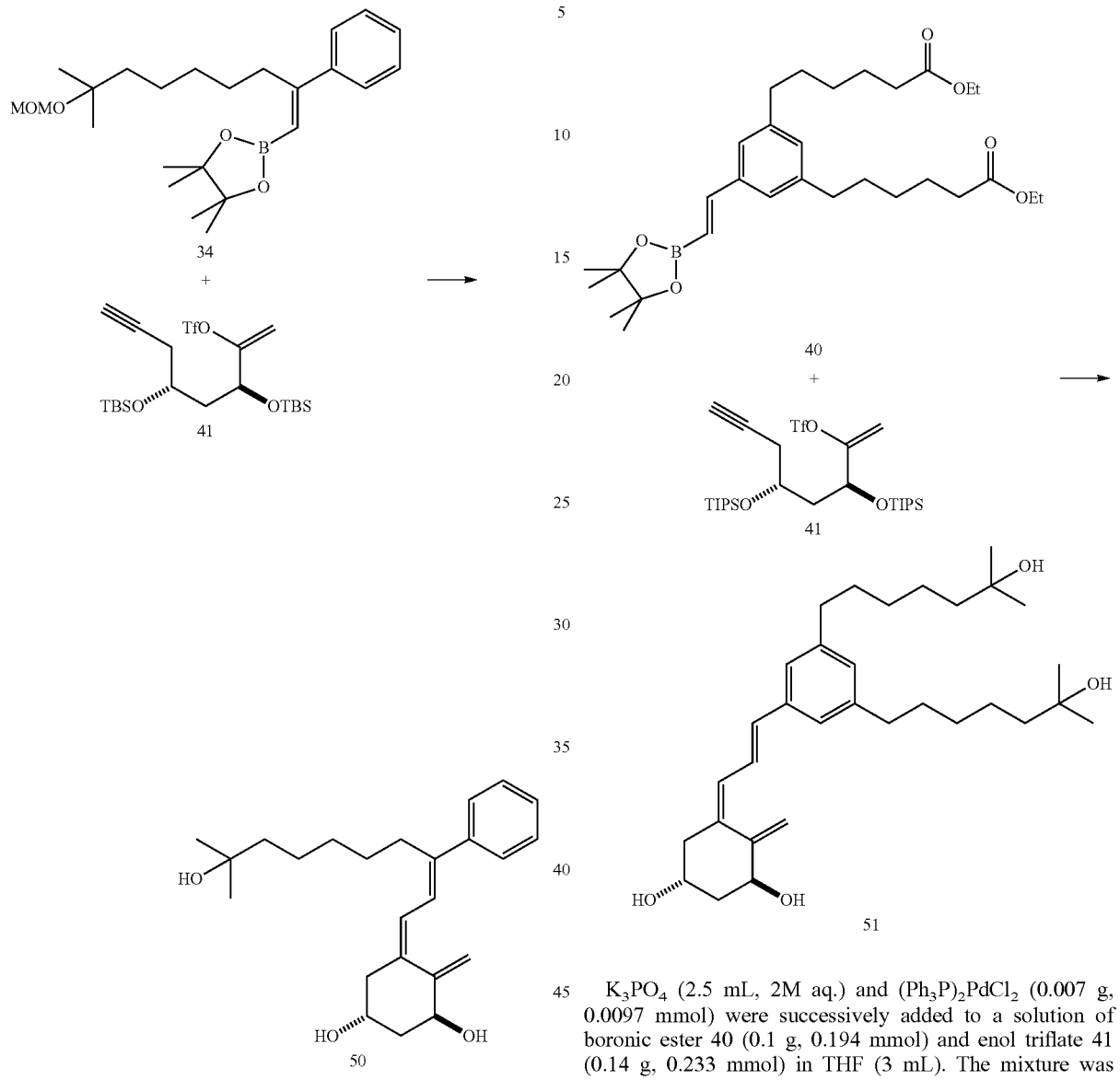

Following the preparation procedure of tetraol (50) using K$_3$PO$_4$ (6 mL, 2M aq), (Ph$_3$P)$_2$PdCl$_2$ (0.0174 g, 0.0245 mmol), a solution of boronic ester 34 (0.2 g, 0.497 mmol) and enol triflate 41 (0.308 g, 0.596 mmol) in THF (8 mL), THF (5 mL), a solution of TBAF in THF (2 mL, 2 mmol, 1M) MeOH (15 mL) and resin AG50W-X4 (3 g, wet weight, freshly washed with MeOH), the tetraol 50 (0.14 g, 0.378 mmol, 76%) was obtained. $^1$H NMR (250 MHz, CDCl$_3$): δ=7.03-7.25 (m, 5H), 6.59 (d, J=11.4 Hz, 1H), 6.29 (d, J=11.4 Hz, 1H), 5.2 (bs, 1H), 4.94 (bs, 1H), 4.25-4.36 (m, 1H), 4.01-4.16 (m, 1H), 2.38-2.95 (m, 6H), 2.24 (q, J$_1$=7.0 Hz, J$_2$=13.1 Hz, 1H), 1.76-1.89 (m, 2H), 1.04 (bs, 6H); HRMS (EI+): [M]$^+$ calculated for C$_{24}$H$_{34}$O$_3$ 370.2508. found 370.2492; [α]$_D^{25}$=+33.61° (c=2.11 in EtOH).

K$_3$PO$_4$ (2.5 mL, 2M aq.) and (Ph$_3$P)$_2$PdCl$_2$ (0.007 g, 0.0097 mmol) were successively added to a solution of boronic ester 40 (0.1 g, 0.194 mmol) and enol triflate 41 (0.14 g, 0.233 mmol) in THF (3 mL). The mixture was stirred vigorously for 1 h at rt. The reaction mixture was diluted with H$_2$O and extracted with Et$_2$O. The organic phase was dried and concentrated. The residue was purified by flash chromatography to yield the protected compound, which was dissolved in THF (5 mL) and cooled at −78° C. It was stirred for 15 min and then a solution of MeMgBr in THF (0.97 mL, 0.97 mmol, 1M) was added. The mixture was stirred 4 h at rt and diluted with NH$_4$Cl (aq. sat) and the mixture was extracted with EtOAc. The organic phase was dried and concentrated. The residue was purified by flash chromatography to yield the protected diol, which was dissolved in THF (5 mL). A solution of TBAF in THF (0.78 mL, 0.78 mmol, 1M) was added. The reaction mixture was stirred for 5 h at rt and then diluted with NH$_4$Cl (aq. sat). The mixture was extracted with EtOAc. The organic phase was dried and concentrated. The residue was purified by flash chromatography to give the tetraol 51 (0.07 g, 0.14 mmol, 72%). $^1$H NMR (250 MHz, CDCl$_3$): δ=7.09 (dd, J$_1$=10.9 Hz, J$_2$=15.6 Hz, 1H), 6.97 (bs, 2H), 6.83 (bs, 1H), 6.49 (d, J=15.6 Hz, 1H), 6.18 (d, J=10.9 Hz, 1H), 5.37 (bs, 1H), 5.05 (bs, 1H), 4.46 (t, J=5.5 Hz, 1H), 4.15-4.27 (m, 1H), 2.47-2.66 (m, 6H), 2.25-2.39 (m, 2H), 1.96 (t, J=5.3 Hz, 2H), 1.52-1.69 (m, 4H), 1.18 (bs, 12H); HRMS (EI+): [M]+ calculated for $C_{32}H_{50}O_4$ 498.3709. found 498.3691; $[\alpha]_D^{25}$=+12.3° (c=1.46 in EtOH).

Biological Activity
Methods and Results
Cell Culture

The cell lines of human breast (MCF-7), prostate (PC3), and ovarian (SKOV-3) adenocarcinoma were obtained from the European Collection of Cell Cultures. The HaCaT keratinocyte cell line was obtained from Dr. Miguel Quintanilla (Department of Cancer Biology, IIB Alberto Sols, CSIC, Madrid). The cells were cultured in 90-mm plates in essential culture medium DMEM, supplemented with 10% bovine foetal serum free of steroid hormones, 100 U/ml penicillin, 100 μg/ml streptomycin and 2 mM non-essential amino acids (L-glutamine) at 37° C. in a humid atmosphere $O_2/CO_2$ (95/5%).

Compounds

The 1,25-dihydroxyvitamin D3 (1,25D) and different analogues PG-136p; PG-152; PG-128; PG-156; PG-403; PG-385 and PG-433 were resuspended in absolute ethanol at a concentration of $10^{-3}$ M, and from this solution, the concentrations used for each experiment were obtained (from $10^{-5}$ to $10^{-11}$M).

Binding Affinity of 1,25D and its Analogues to Vitamin D Receptor (VDR)

The affinity of 1,25-dihydroxyvitamin D3 (1,25D) and its analogues to VDR was determined by competitive displacement assay (Polarscreen Vitamin D receptor competitor assay, Red, Invitrogen). Polarised fluorescence was determined in 384-well black plates for 200 ms/well using a Mithras LB 940 device (Berthold Technologies). The compounds were assessed at a range of concentrations that ranged from $10^{11}$ M-$10^{-5}$ M, calculating the $IC_{50}$ for 1,25D and for each analogue. The activity of each analogue was expressed as percentage relative to the activity of the natural hormone (1,25D), which is normalised at 100%.

The results obtained indicate that, from the compounds tested, the compound PG-136p is the one with higher affinity to VDR ($IC_{50}$: 7.11×$10^{-9}$, 24%), relative to 1,25D hormone ($IC_{50}$:1.74×$10^{-9}$ 100% binding). The other compounds have the following affinity percentage: PG-152: 10%, PG-128: 12%; PG-156: 9%, and PG-403: 7% (FIG. 1; TABLE 1).

TABLE 1

Binding of 1,25D and its analogues to vitamin D receptor (VDR)

| Compounds | Binding to VDR | |
|---|---|---|
| | $IC_{50}$ (M) | % |
| 1,25D | 1.74 × $10^{-9}$ | 100 |
| PG-136p | 7.11 × $10^{-9}$ | 24 |
| PG-152 | 1.76 × $10^{-8}$ | 10 |
| PG-128 | 1.36 × $10^{-8}$ | 12 |
| PG-156 | 1.84 × $10^{-8}$ | 9 |
| PG-403 | 2.35 × $10^{-8}$ | 7 |

Transactivation Assays

In order to assess in vivo the effect of administration of 1,25D analogues, transient transfections were performed with the promoter of a target gene of vitamin D bonded to a luciferase reporter vector (24-hydroxylase promoter, CYP24A1, pCYP24A1-Luc). MCF-7 cells were transfected with the vector pCYP24A1-Luc or its control pGL2B for 48 h, and treated further 24 h with each of the analogues and 1,25D at concentrations ranging from $10^{11}$ M to $10^{-6}$ M. After 72 h (from the start of transfection) cells were treated with luciferin (100 mg/L) and bioluminescence was visualised in an IVIS imaging system (CaliperLifeSciences, Alameda, Calif., USA). the $EC_{50}$ was determined for each analogue and for 1,25D, which served as a standard.

Figure 2:
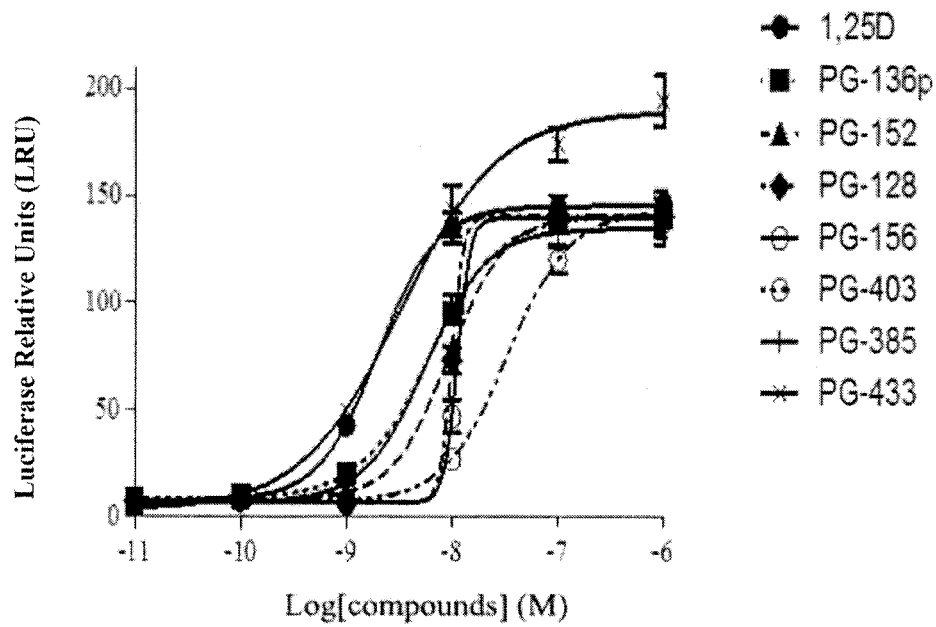
FIG. 2. Transactivation experiment (reporter assay) of 1,25D and of various analogues according to the present invention. MCF-7 cells were transfected with the reporter vector of 24-hydroxylase (pCYP24A1-Luc vector) for 24 hours. These cells were treated with 1,25D and the various analogues for 24 hours at concentration of $10^{-11}$-$10^{-8}$ [M]. Then the luciferase activity was determined and the EC$_{50}$ was calculated, which represents the analogue concentration which increases the transcipcional activity by 50% according to the dose-response curves, as indicated in the description (Table 2). The experiments were performed at least twice. The error bars represent the standard deviation (SD).

The results obtained indicate that the compounds PG-433, PG-385 and PG-136p are those with greater ability to activate target genes of 1,25D (67, 35, and 33%, respectively) relative to the natural hormone 1,25D (100% transactivation). The other compounds have the following transactivation capacity percentage (relative to 1.25D): PG-152: 21%, PG-128: 20%; PG-156: 17%; PG-403: 6% (FIG. 2; TABLE 2).

TABLE 2

Transcriptional activity of 1,25D and analogues thereof in MCF-7 cells (reporter gene: pCYP24A1-Luc).

| | Transcriptional activity | |
|---|---|---|
| Compounds | $EC_{50}$ (M) | % |
| 1,25D | 1.97 × $10^{-9}$ | 100 |
| PG-136p | 5.97 × $10^{-9}$ | 33 |
| PG-152 | 9.27 × $10^{-9}$ | 21 |
| PG-128 | 1.00 × $10^{-8}$ | 20 |
| PG-156 | 1.14 × $10^{-8}$ | 17 |
| PG-403 | 3.46 × $10^{-8}$ | 6 |
| PG-385 | 5.60 × $10^{-9}$ | 35 |
| PG-433 | 2.95 × $10^{-9}$ | 67 |

Inhibition of Cell Proliferation

Cell proliferation/toxicity in breast cancer lines was assessed by both incorporation assays of 3-(4,5-dimethyl-thiazol-2-yl)-2,5-difeniltetrazolium (MTT) bromide and cell culture in three dimensions (3D).

The first is an indirect method for determining living cells, wherein the yellow water soluble MTT is reduced in mitochondria, thus generating a purple insoluble product (formazan). The measuring of the optical density of the formazan once solubilsed allows for determining the cell cytotoxicity rate that cells undergo with different treatments (1,25D, as a control, and analogues thereof). 24 hours after seeding 30,000 cells per well in 24-well plates, the various analogues and 1,25D were administered at a concentration of $10^{-8}$ and $10^{-7}$ M and incubated for 48 hours. Once the treatment time has passed, MTT was added (500 mg/ml) and incubated for 1 hour. After this time, the culture medium was removed and 500 μl of dimethylsulfoxide (DMSO) was added to each well to solubilise the formazan incorporated by the cells. Finally the absorbance was measured in each well in an automatic plate reader at a wavelength of 590 nm.

Figure 3:
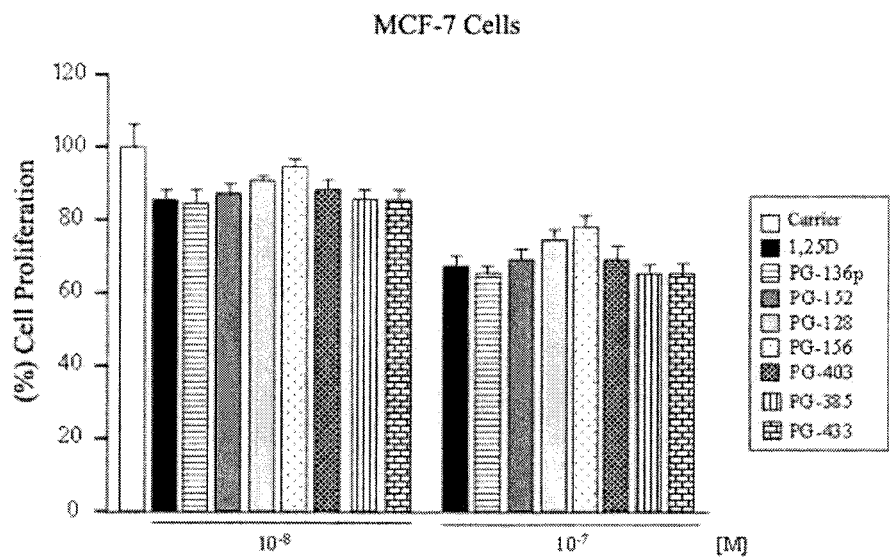
FIG. 3. Proliferation assay in the MCF-7 cell line of human breast adenocarcinoma. MCF-7 cells were seeded in 24-well plates, after 24 hours, the cells were treated with 1,25D and various analogues, according to the present invention, at $10^{-8}$ and $10^{-7}$ [M] for 48 hours and then incubated with the MTT reagent for 1 hour. Absorbance was determined at 570 nm. The values were plotted in the graphs as mean±SD. As proliferation value, 100% was considered the normal growth of MCF-7 cells treated with the carrier in the control.

The results obtained indicate that cell proliferation in MCF-7 line after treatment with $10^{-7}$ M 1,25D is 66% (100% in control cells), and with analogues: PG-136p: 65%; PG-152: 69%; PG-128: 74%; PG-156: 78%; PG-403: 69%; PG-385: 69%, and PG-433: 69% (FIG. 3; TABLE 3).

TABLE 3

Percentage of cell proliferation in different cell lines of 1,25 and analogues (100% control cells).

| Compound | MCF-7 2D (%) | MCF-7 3D (%) | PC-3 2D (%) | SKOV-3 2D (%) | HaCaT 2D (%) |
|---|---|---|---|---|---|
| 1,25D | 66 | 61 | 77 | 78 | 69 |
| PG-136p | 65 | 69 | 78 | 78 | 68 |
| PG-152 | 69 | 74 | 83 | 82 | 71 |
| PG-128 | 74 | 84 | 84 | 81 | 71 |
| PG-156 | 78 | 79 | 80 | 76 | 74 |
| PG-403 | 69 | 55 | 79 | 83 | 71 |
| PG-385 | 69 | | | | |
| PG-433 | 69 | | | | |

Figure 4:
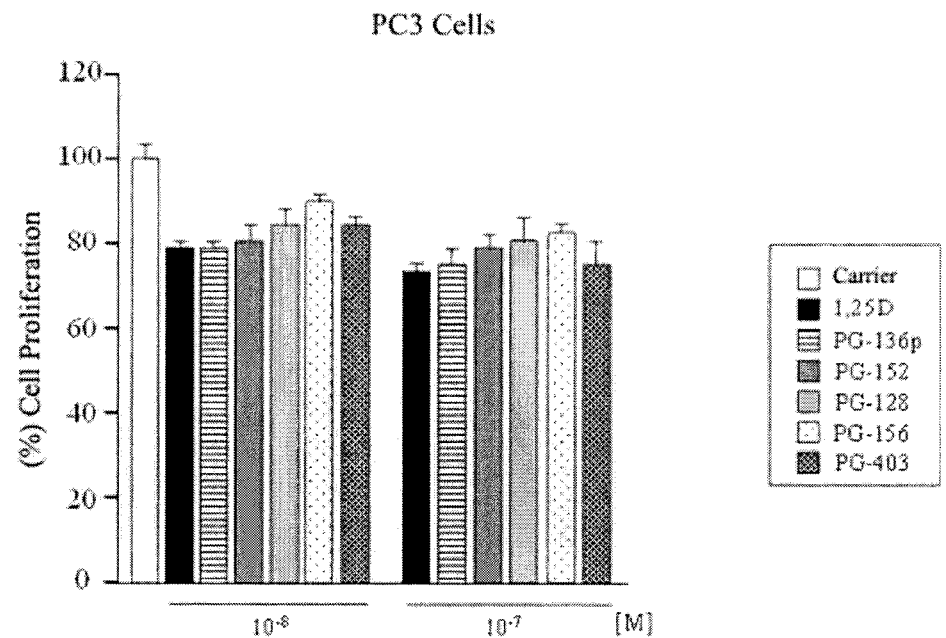
FIG. 4. Proliferation assay in the PC-3 cell line of human prostate adenocarcinoma. PC-3 cells were seeded in 24-well plates, after 24 hours, the cells were treated with 1,25D and various analogues, according to the present invention, at $10^{-8}$ and $10^{-7}$ [M] for 48 hours and then incubated with the MTT reagent for 1 hour. Absorbance was determined at 570 nm. The values were plotted in the graphs as mean±SD. As proliferation value, 100% was considered the normal growth of PC-3 cells treated with the carrier in the control.

In the PC-3 cell line of prostate cancer cell proliferation after treatment with $10^{-7}$ M 1,25D is 77% (100% in control cells), and with $10^{-7}$ M of analogues: PG-136p: 78%; PG-152: 83%; PG-128: 84%; PG-156: 80%, and PG-403: 79% (FIG. 4; TABLE 3).

Figure 5:
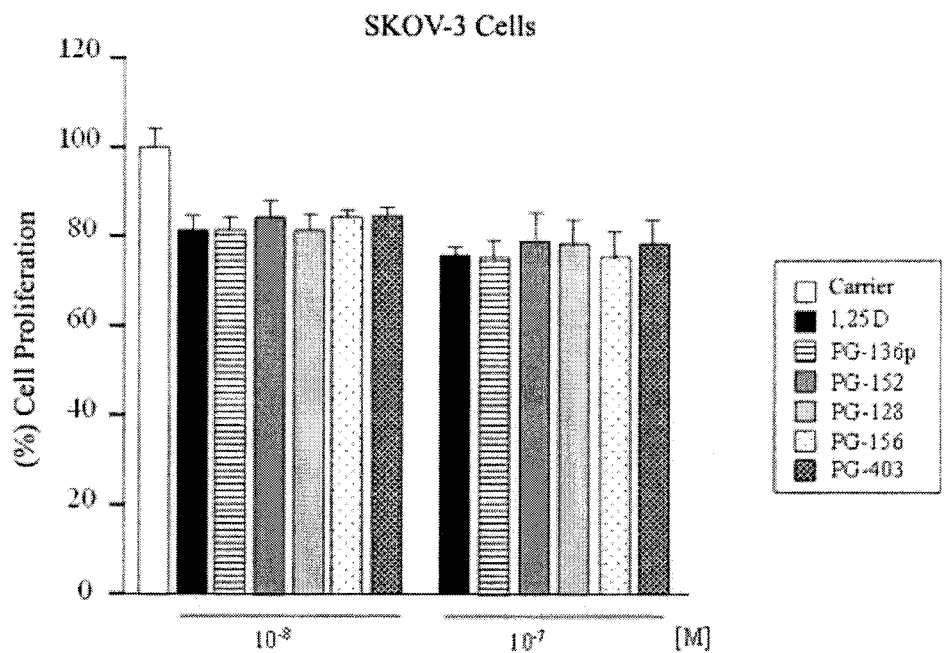
FIG. 5. Proliferation assay in the SKOV-3 cell line of human ovary adenocarcinoma. SKOV-3 cells were seeded in 24-well plates, after 24 hours, they were treated with 1,25D and various analogues, according to the present invention, at $10^{-8}$ and $10^{-7}$ [M] for 48 hours and then incubated with the MTT reagent for 1 hour. Absorbance was determined at 570 nm. The values were plotted in the graphs as mean±SD. As proliferation value, 100% was considered the normal growth of SKOV-3 cells treated with the carrier in the control.

In the SKOV-3 cell line of ovarian cancer cell proliferation after treatment with $10^{-7}$ M 1,25D is 78% (100% in control cells), and with $10^{-7}$ M of analogues: PG-136p: 78%; PG-152: 82%; PG-128: 81%; PG-156: 76%, and PG-403: 83% (FIG. 5; TABLE 3).

Figure 6:
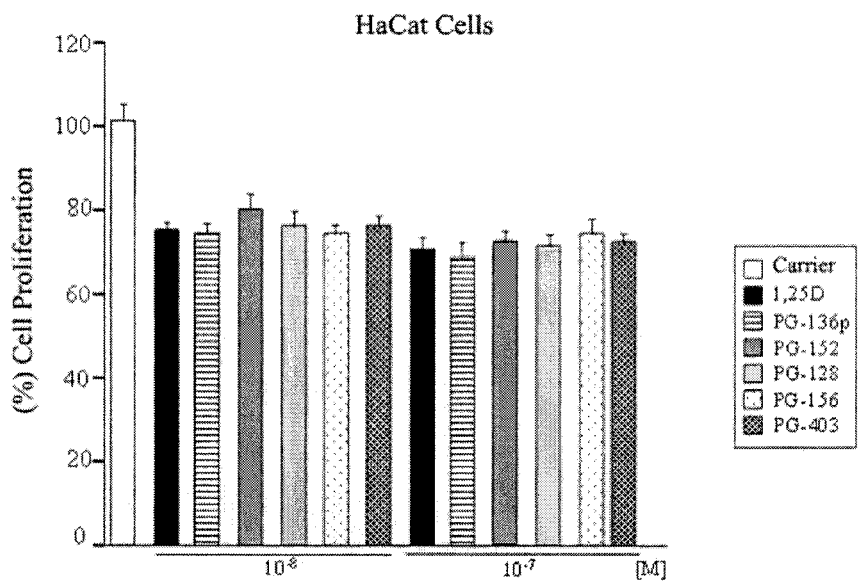
FIG. 6. Proliferation assay in the HaCaT cell line of human keratinocytes. HaCaT cells were seeded in 24-well plates, after 24 hours, they were treated with 1,25D and various analogues, according to the present invention, at $10^{-8}$ and $10^{-7}$ [M] for 48 hours and then incubated with the MTT reagent for 1 hour. Absorbance was determined at 570 nm. The values were plotted in the graphs as mean±SD. As proliferation value, 100% was considered the normal growth of HaCaT cells treated with the carrier in the control.

In the HaCaT keratinocyte cell line, the proliferation after treatment with $10^{-7}$ M 1,25D is 69% (100% in control cells), and with $10^{-7}$ M of analogues: PG-136p: 68%; PG-152: 71%; PG-128: 71%; PG-156: 74%, and PG-403: 71% (FIG. 6; TABLE 3).

For 3D cell culture, a cushion of 200 μl of Matrigel (BD Biosciences) was used in each of the wells of multi-well plates of 24 wells. They were incubated at 37° C. for 20 minutes for their solidification and subsequently the cell suspension ($5\times10^3$ cells per 100 μl volume of medium) was loaded onto the matrigel solidified and another incubation at 37° C. was performed for 30 minutes so that the cells penetrated properly on the matrigel base. 500 μl of DMEM medium were added to each well, and the cells were maintained in culture for 10 days. At the end of this time, the cells were started to be treated with each of the 5 analogues used and 1,25D. After another 10 days, photographs of the wells were taken using a microscope (Nikon Eclipse Ti-S) equipped with a camera C3 ProgRes and the diameter of the spheres was quantified manually.

Figure 7:
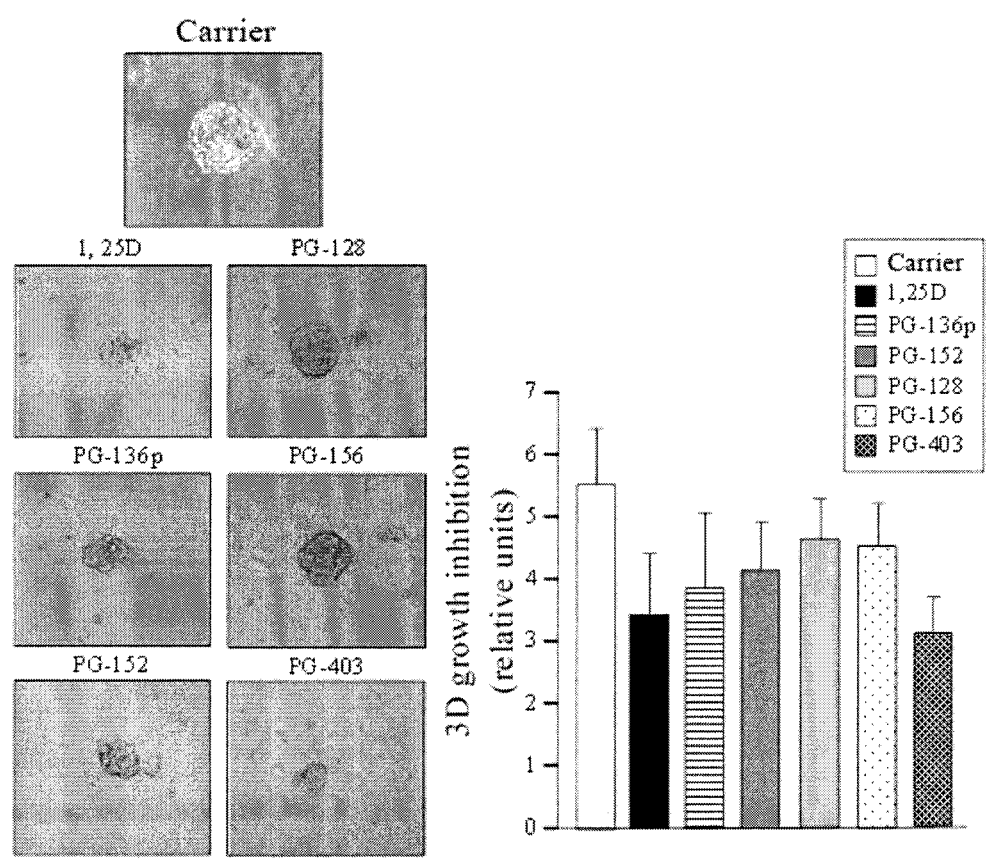
FIG. 7. MCF-7 cells were shown for 10 days on a matrigel bed until they formed a 3D cellular structure. These spheroids were treated with 1,25D and various analogues according to the present invention, at a concentration of $10^{-7}$ [M] for 7 days. After treatment, the spheroids were stained with DAPI (4',6-diamino-2-phenylindole) for 1 hour and photographed under an inverted microscope with ultraviolet light. The size of these spheroids was measured and the values were represented as mean±SD in relative units. In the figure it can be observed that analogue PG-136p and PG-403 according to the present invention, inhibit the three-dimensional growth, similarly to 1,25D. Those cells treated with the carrier were considered as the control value.

The results obtained indicate that 3D cell proliferation-growing in MCF-7 line after treatment with $10^{-7}$ M 1,25D is 61% (100% in control cells), and with $10^{-7}$ M analogues: PG-136p: 69%; PG-152: 74%; PG-128: 84%; PG-156: 79%, and PG-403: 55% (FIG. 7; TABLE 3).

Calcaemic Effects

Calcium mobilization of analogues was determined in 28 male CD-1 mice (6-8 weeks old). 6 Groups of 4 mice each were established, which mice were intraperitoneally (ip) injected with 0.3 μg/kg weight of each analogue or 1,25D dissolved in sesame oil every two days for 3 weeks. A seventh group of 4 mice treated with the carrier (sesame oil) served as controls. Calcium levels in blood were determined by QuantiChomCalciumAssay Kit (BioAssaySystems, Hayward, Calif., USA). In addition, a dose-response assay was performed to assess the effect of administration of the analogues PG-403 and PG136p and hormone (1,25D) at different doses on calcium levels. This assay was performed in male mice (5 mice per group), and the doses used were: 0.1, 0.5, 1, and 5 μg/kg weight of each analogue or 1,25D, i.p. administered every two days for 21 days. In addition, a control group (mice treated with sesame oil) was used.

Figure 8:
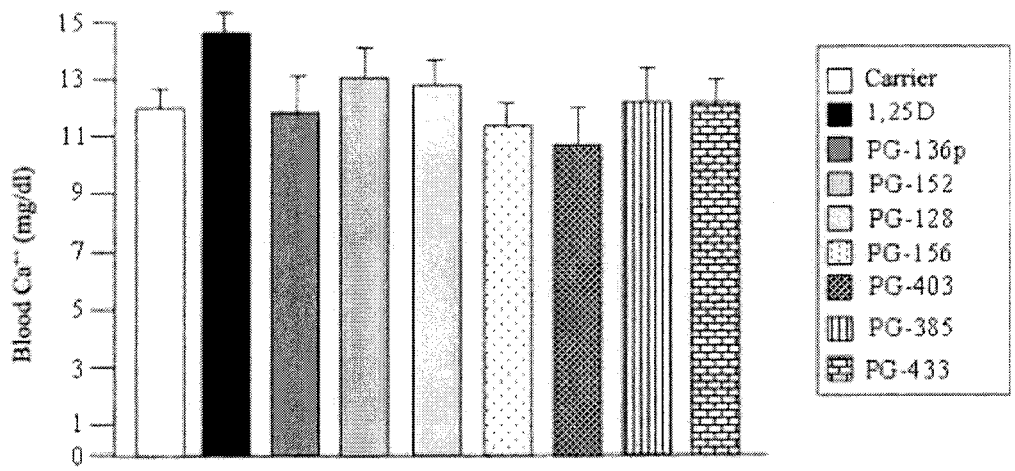
FIG. 8. Treatment with the PG-128, PG-136p, PG-152, PG-156, PG-403, PG-385 and PG-433 analogues, according to the present invention, does not produce hypercalcemia in mice (no significant differences with respect to the control). 1,25D and the various analogues were injected intraperitoneally every 2 days for 21 days at a dose of 0.3 µg/Kg. After treatment the calcium levels in the serum were evaluated and the values were represented as mean±SD in mg/dL.

The results obtained in the first test indicate that treatment with 1,25D at doses of 0.3 μg/kg weight induces a significant increase of blood calcium (14.7±0.58 mg/dl) compared to carrier treated mice (11.9±0.7 mg/dl) (FIG. 8, TABLE 4). The blood calcium levels of mice treated with analogues, expressed in percentage over the blood calcium induced following treatment with 1,25D were: PG-136p: 0%; PG-152: 41%; PG-128: 34%; PG-156: 0%; PG-403: 0%; PG-385: 9%, and PG-433: 8% (FIG. 8; TABLE 4).

TABLE 4

Calcaemic activity of 1,25D and analogues in mice injected with 0.3 mg/kg weight every two days for 21 days.

| Compounds | Calcaemic activity % |
|---|---|
| 1,25D | 100 |
| PG-136 | 0 |
| PG-152 | 41 |
| PG-128 | 34 |
| PG-156 | 0 |
| PG-403 | 0 |
| PG-385 | 9 |
| PG-433 | 8 |

Figure 9:
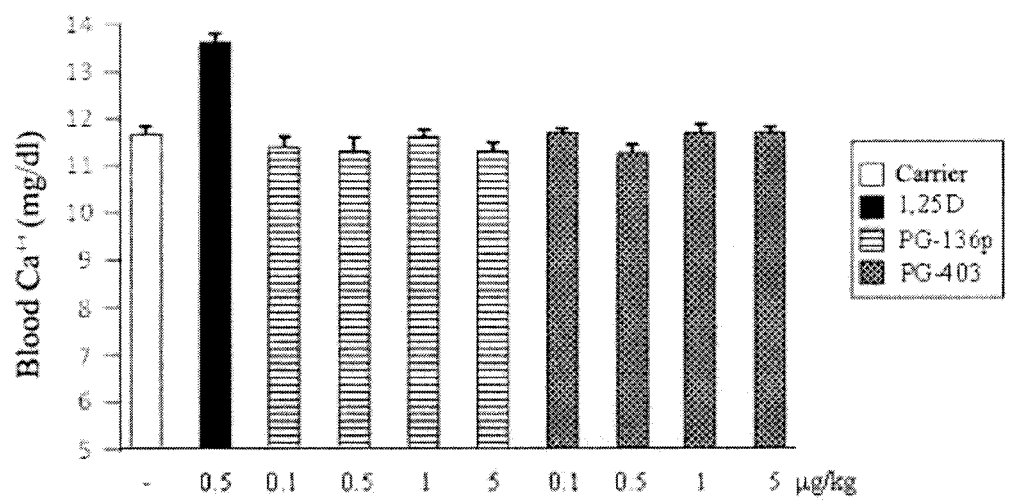
FIG. 9. Treatment with the PG-136p and PG-403 analogues, according to the present invention, at doses of 0.1, 0.5, 1 and 5 µg/kg does not produce hypercalcemia in mice. 1,25D (dose of 0.3 µg/kg) and analogues (doses of 0.1, 0.5, 1 and 5 µg/kg) were injected intraperitoneally every 2 days for 21 days. After treatment the calcium levels in the serum were evaluated and the values were represented as mean±SD in mg/dL.
Figure 10:
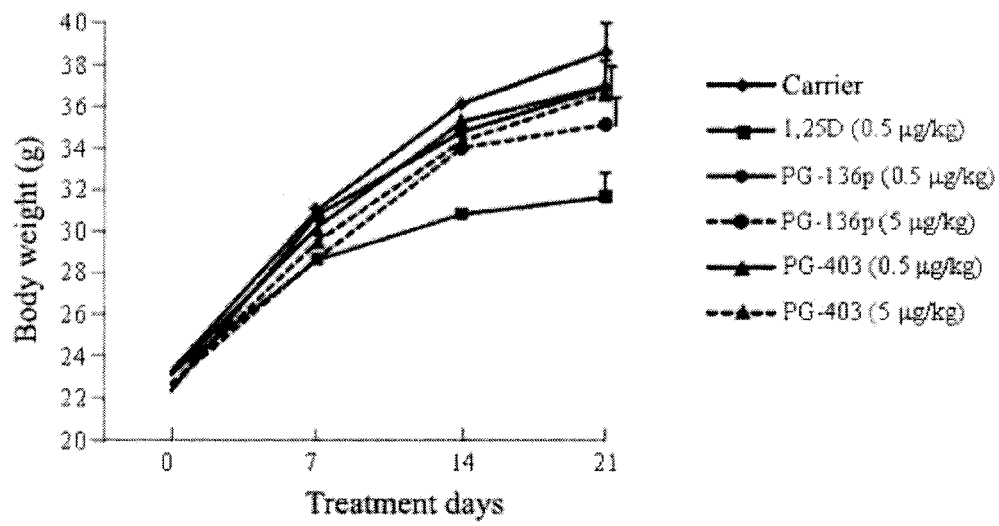
FIG. 10. Treatment with PG-136p and PG-403 analogues, according to the present invention, at doses of 0.1, 0.5, 1 and 5 µg/kg does not change the body weight of the mice with respect to the control animals (treated with carrier). 1,25D (dose of 0.3 µg/kg) and analogues (doses of 0.1, 0.5, 1 and 5 µg/kg) were injected intraperitoneally every 2 days for 21 days. Animals were weighed every two days during treatment. The values were represented as mean±SD in mg/dL.

The results obtained in the second dose-response assay (assessment of serum calcium with different concentrations of 1,25D and analogues PG136p and PG-403) indicate that 1,25D induces a significant increase in serum calcium (relative to controls) at doses of 0.5 μg/kg weight. None of the two analogues tested (PG136p and PG-403) induces increased serum calcium (compared to controls) at any dose used (0.1, 0.5, 1, and 5 μg/kg weight) (FIG. 9). In this experiment, also the weight of the animals was quantified to determine whether there was any modification throughout the treatment. While 1,25D treatment at doses of 0.5 μg/kg weight produced a significant decrease in the weight of the animals, treatment with analogues PG136p and PG-403 at the same dose or higher doses (1 and 5 μg/kg weight) did not significantly affect the body weight of mice (FIG. 10).

Western Blot

In order to assess protein expression of genes regulated by 1,25D after administration of the analogues, seeding of MCF-7 was performed in petri dishes, which were treated for 48 h at different concentrations with each analogue or with 1,25D ($10^{-7}$, $10^{-8}$, $10^{-9}$). Subsequently, a protein extraction used for electrophoresis was performed. Each sample was re-suspended in loading buffer consisting of 50 mM Tris-HCl pH 6.8, 2% SDS, 2% of βmercaptoethanol and bromophenol blue. The samples were loaded in a 12% SDS-PAGE gel and transferred to nitrocellulose membranes for 2 hours at 4° C. After blocking with PBS (to which 0.1 g casein and 0.1% Tween 20 were added for 1 hour at room temperature), the membranes were incubated overnight at 4° C. with polyclonal anti-p21, anti-p27 and anti-p53 antibodies. For compounds PG-385 and PG-433 a Western blot was performed with E-cadherin.

After several washings with PBST buffer, it was incubated with a second anti-rabbit anti-IgG antibody (1:5000) conjugated to peroxidase for 1 hour at room temperature. The membrane was re-washed 5 times with PBST buffer and finally was added the chemiluminescent reagent (Pierce, ECL Western blotting substrate) for its labelling. The immunolabeling was detected using auto-radiography plates.

Figure 11A:
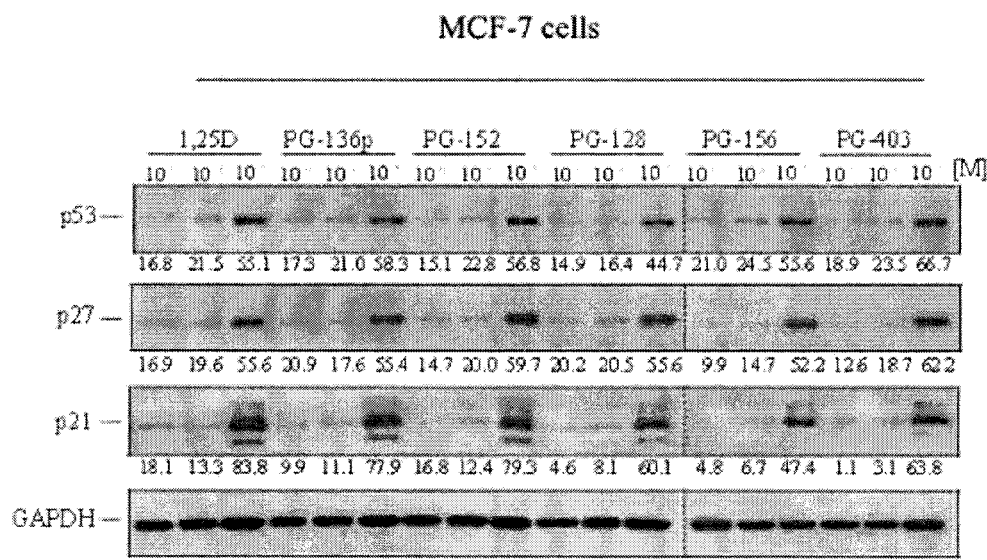
FIGS. 11 (A and B) The analogues, according to the present invention regulate target genes of vitamin D similarly to 1,25D. MCF-7 cells were treated for 24 hours with various analogues at doses of $10^{-9}$, $10^{-8}$ and $10^{-7}$ M. Protein extracts were electrophoresed, transferred to PVDF membranes and incubated with anti-p21, anti-p27, anti-p53 (A) or anti-E-cadherin (B) antibodies (anti-GAPDH was used as a load control). Western blot bands were quantified by densitometry and data are expressed as the ratio of anti-p21, anti-p27, anti-p53 and anti-GAPDH.
Figure 11B:
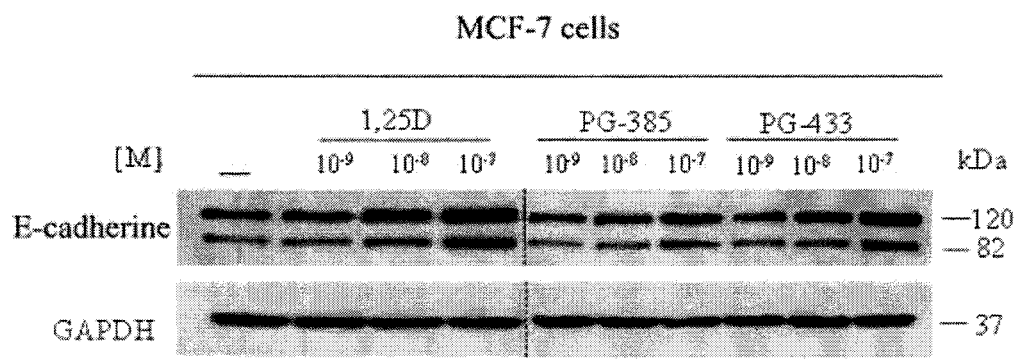

The results obtained indicate that, similarly to 1,25D, all analogues used at a dose of $10^{-7}$ M induce protein expression of p53, p27 and p21 (FIG. 11A), which, as mentioned, are target genes of 1,25D involved in controlling the cell cycle (p21 and p27) and cell death/DNA repair (p53). For compounds PG-385 and PG-433, E-cadherin was used as target gene of 1,25D (FIG. 11B).

Statistical Analysis

The resulting values for each experiment are expressed as mean±standard deviation. The results were compared using variance analysis for a single factor, also referred to as ANOVA, using a significance level of p<0.05.

In Vivo Anti-Tumour Biological Activity

In order to study the anti-tumour activity of the analogue PG136 in vivo, 32 immunosuppressed CB17-Prkdc$^{scid}$ 8 weeks old female mice were used, called SCID (PRBB, Barcelona, Spain). These mice were injected subcutaneously with 5×10$^6$ breast tumour cells MCF-7 and MDA-MB-231 stably transfected with plasmid pcDNA3-Luciferase coding for the gene of the luciferase (called MCF-7-Luc and MDA-MB-231-Luc). Two groups of 8 mice were injected with cells MCF-7-Luc and other 2 groups of 8 mice with MDA-MB-231-Luc cells. Fifteen days after injection, the mice were started to be treated intraperitoneally every 2 days for 28 days with the analogue PG136 at a dose of 5 µ/kg dissolved in sesame oil used as carrier. The control group is treated in the same way and with the same range with sesame oil. Tumour size is determined every seven days once started the treatment using an in vivo imaging system (IVIS, Caliper Life Sciences, Alameda, USA), and the tumour size is calculated using a map of intensities retrieved using the Living Image (Caliper Life Sciences) software. In the case of the 2 groups of mice injected with MDA-MB-231-Luc cells, the experiment continued until day 60 and Kaplan-Meier Survival estimates were made.

Figure 12:
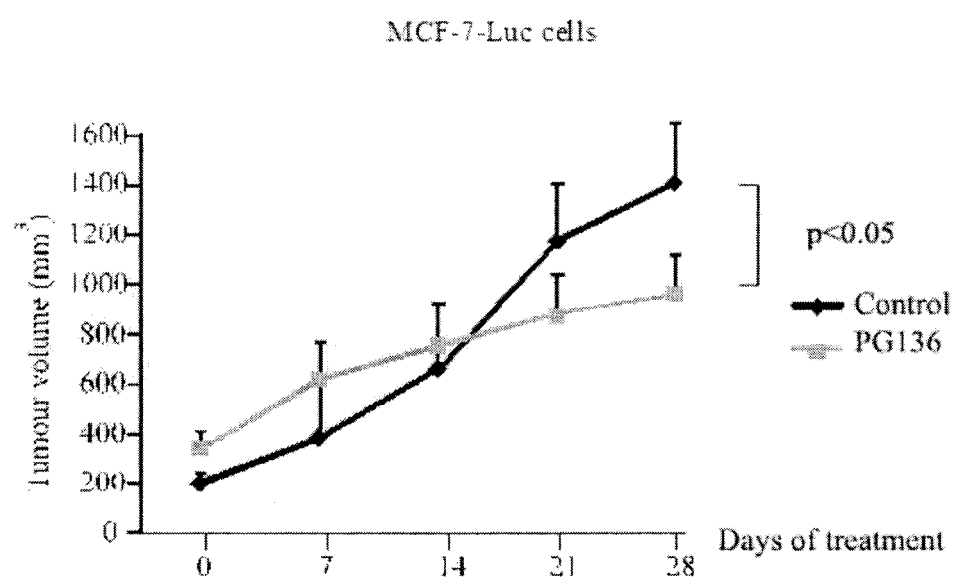
FIG. 12. In this figure the results obtained by treating a group of 32 mice with the analogue PG136 after being injected with MCF-7-Luc cells are shown.
Figure 13:
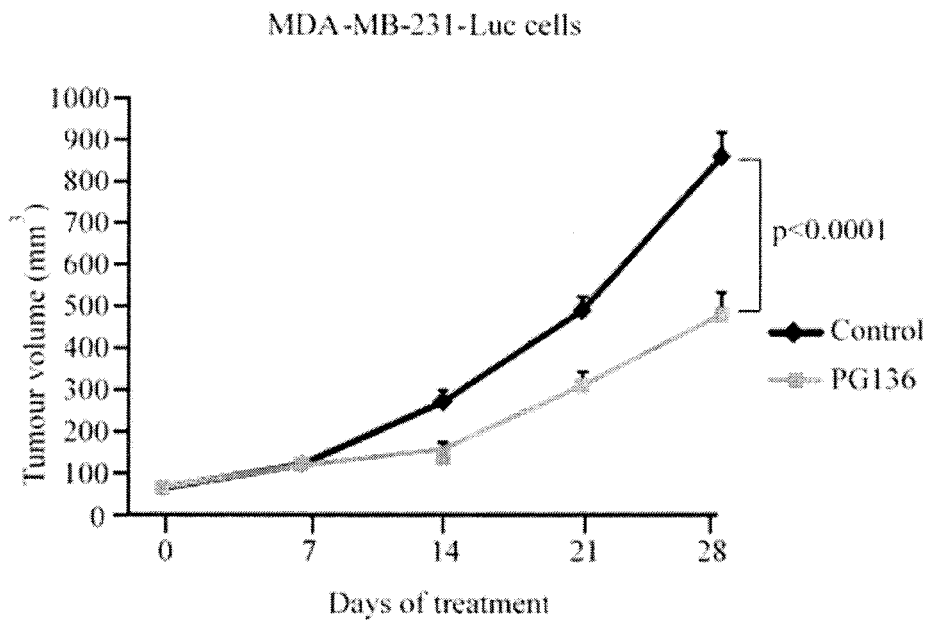
FIG. 13. In this figure the results obtained by treating a group of 32 mice with the analogue PG136 after being injected with MDA-MB-231-Luc cells are shown.
Figure 14:
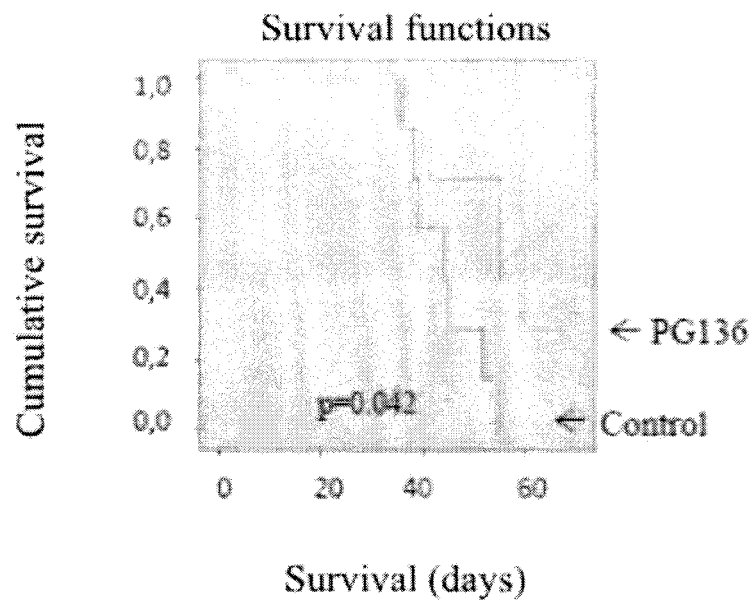
FIG. 14. The survival rate of mice treated with the analogue PG136 after being injected with MDA-MB-231-Luc cells is shown and compared with control mice.

The results obtained indicate that the tumours produced in mice injected with MCF-7-Luc and MDA-MB-231-Luc cells have smaller volume (p≤0.05 and p≤0.0001 respectively) when they are treated with the analogue PG136 (FIG. 12 and FIG. 13) compared to the control group injected with MDA-MB-231-Luc cells and treated with the carrier. In addition, mice injected with MDA-MB-231-Luc cells and treated with the analogue PG136 have a higher survival rate (p=0.042) than control mice (FIG. 14).

The invention claimed is:

1. A compound of formula (I), or stereoisomer or pharmaceutically acceptable salts thereof,

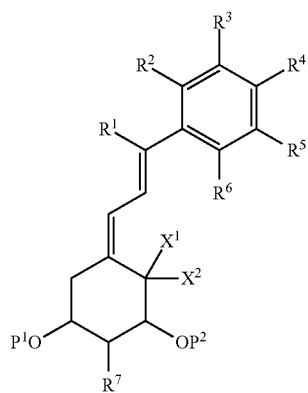
(I)

wherein each of $R^1$, $R^2$, $R^3$, $R^4$, $R^5$, $R^6$ and $R^7$, is independently selected from a group consisting of hydrogen, $(C_1$-$C_{12})$alkyl, $(C_1$-$C_{12})$hydroxyalkyl, $(C_2$-$C_{12})$alkenyl, $(C_2C_{12})$hydroxyalkenyl, $(C_2$-$C_{12})$alkynyl, $(C_2$-$C_{12})$ hydroxyalkynyl, $(C_1C_{12})$heteroalkyl, $(C_2$-$C_{12})$heteroalkenyl, $(C_1$-$C_{12})$heteroalkynyl, $(C_6C_{10})$aryl, $(C_3$-$C_{15})$heteroaryl, $(C_6$-$C_{10})$aryl$(C_1$-$C_{12})$alkyl, $(C_1$-$C_{12})$alkylacyl, $(C_6$-$C_{10})$arylacyl, $(C_1C_{12})$alkoxyl, $(C_6$-$C_0)$aryloxyl, $(C_1$-$C_{12})$alkylcarboxy, $(C_6C_{10})$ arylcarboxy, $(C_1$-$C_{12})$carbocycle and $(C_3C_{15})$heterocycle, wherein $R^1$, $R^2$, $R^3$, $R^4$, $R^5$, $R^6$ and $R^7$ are optionally substituted by hydrogen, $(C_1$-$C_{12})$alkyl or $(C_1C_{12})$hydroxyalkyl, $X^1$ and $X^2$ are hydrogen or, together with the carbon atom to which they are bonded, form a methylene (=CH$_2$) group, and each of $P^1$ and $P^2$ is independently selected from a group consisting of hydrogen, $(C_1C_{12})$alkyl, $(C_6$-$C_{10})$aryl, $(C_1C_{12})$alkoxyl, $(C_6$-$C_{10})$aryloxyl, $(C_1$-$C_{12})$alkylcarboxy, $(C_6C_{10})$arylcarboxy and —OSiR$^a$R$^b$R$^c$, wherein each of R$^a$, R$^b$ and R$^c$ are selected from $(C_1$-$C_{12})$alkyl, $(C_6$-$C_{10})$aryl, $(C_6$-$C_{10})$aryl, $(C_1$-$C_{12})$alkyl, $(C_1C_{12})$alkoxyl, $(C_6$-$C_{10})$aryloxyl and $(C_3$-$C_{15})$heterocycle, wherein between 1 to 9 hydrogen atoms in the compound of formula (I) are optionally substituted by hydrogen, deuterium ($^2$H) or tritium ($^3$H) isotopes, and/or from 1 to 9 carbon atoms in the compound of formula (I) are optionally substituted by $^{11}$C, $^{13}$C, $^{14}$C isotopes.

2. The compound of formula (I) according to claim 1, wherein each of $R^1$ and $R^5$ is independently selected from a group consisting of hydrogen, $(C_1$-$C_{12})$alkyl and $(C_1C_{12})$hydroxyalkyl and $R^3$ is selected from $(C_1$-$C_{12})$alkyl and $(C_1C_{12})$hydroxyalkyl.

3. The compound of formula (I) according to claim 2, wherein $R^1$ is $(C_1$-$C_{12})$alkyl and $R^3$ is $(C_1$-$C_{12})$hydroxyalkyl.

4. The compound of formula (I) according to claim 1, wherein $R^7$ is hydrogen, and wherein $R^2$, $R^4$ and $R^6$ are hydrogen.

5. The compound of formula (Ia) according to claim 1,

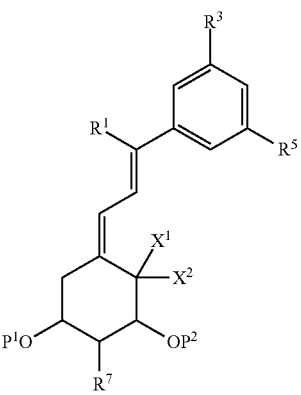
(Ia)

wherein R$^1$ is hydrogen, (C1-C12)alkyl or (C1-C12)hydroxyalkyl,
R3 is hydrogen or (C1-C12)hydroxyalkyl, R5 is hydrogen or (C1C12)hydroxyalkyl,
R7 is hydrogen, (C1-C12)alkyl or (C1-C12)hydroxyalkyl, and
X1 and X2, P1 and P$^2$ are as defined in claim 1.

6. The compound of formula (Ia), according to claim 5, wherein $R^1$ is $(C_1C_{12})$alkyl, $R^3$ is $(C_1-C_{12})$hydroxyalkyl and $R^5$ is hydrogen.

7. The compound of formula (Ia), according to claim 5, wherein $R^1$ is $(C_1C_{12})$alkyl, $R^3$ is $(C_1-C_{12})$hydroxyalkyl and $R^5$ is $(C_1-C_{12})$hydroxyalkyl.

8. The compound of formula (Ia), according to claim 5, wherein $R^1$ is hydrogen, $R^3$ is $(C_1-C_{12})$hydroxyalkyl and $R^5$ is $(C_1-C_{12})$hydroxyalkyl.

9. The compound of formula (I), according to claim 1 wherein at least one of $R^1$, $R^3$ and $R^5$ is a branched $(C_1C_{12})$hydroxyalkyl.

10. The compound of formula (I) according to claim 1, wherein $X^1$ and $X^2$ are methylene.

11. The compound of formula (I) according to claim 1, characterised in that it comprises isotopic labelling.

12. The compound of formula (I) according to claim 11, wherein the isotopic labelling is selected from $^{11}C$, $^{13}C$, $^2H$ and $^3H$.

13. The compound of formula (I) according to claim 1, selected from the group consisting of:
(1R,3S,Z)-5-((E)-3-(3-(6-hydroxy-6-methylheptyl)phenyl)pent-2-enyliden)-4-methylenecyclohexane-1,3-diol,
(1R,3S,Z)-5-((E)-3-(3-(7,7,7-trideutero-6-hydroxy-6-trideuteromethylheptyl)phenyl)pent-2-enyliden)-4-methylenecyclohexane-1,3-diol,
(1R,3S,Z)-5-((E)-3-(3-(6-hydroxy-6-methylheptyl)phenyl)hex-2-enyliden)4-methylenecyclohexane-1,3-diol,
(1R,3S,Z)-5-((E)-3-(3-(7,7,7-trideutero-6-hydroxy-6-trideuteromethylheptyl)phenyl)hex-2-enyliden)-4-methylenecyclohexane-1,3-diol,
(1R,3S,Z)-5-((E)-3-(3-(6-hydroxy-6-methylheptyl)phenyl)hept-2-enyliden)4-methylenecyclohexane-1,3-diol,
(1R,3S,Z)-5-((E)-3-(3-(7,7,7-trideutero-6-hydroxy-6-trideuteroheptyl)phenyl)hept-2-enyliden)-4-methylenecyclohexane-1,3-diol,
(1R,3S,Z)-5-((E)-3-(3-(6-hydroxy-6-methylheptyl)phenyl)non-2-enyliden)4-methylenecyclohexane-1,3-diol,
(1R,3S,Z)-5-((E)-3-(3-(7,7,7-trideutero-6-hydroxy-6-trideuteroheptyl)phenyl)non-2-enyliden)-4-methylenecyclohexane-1,3-diol,
(1R,3S,Z)-5-((E)-3-(3-(6-hydroxy-6-methylheptyl)phenyl)dec-2-enyliden)4-methylenecyclohexane-1,3-diol,
(1R,3S,Z)-5-((E)-3-(3-(7,7,7-trideutero-6-hydroxy-6-trideuteroheptyl)phenyl)dec-2-enyliden)-4-methylenecyclohexane-1,3-diol,
(1R,3S,Z)-5-((E)-9-hydroxy-3-(3-(6-hydroxy-6-methylheptyl)phenyl)-9-methyldec-2-enyliden)4-methylenecyclohexane-1,3-diol,
(1R,3S,Z)-5-((E)-9-hydroxy-3-(3-(7,7,7-trideutero-6-hydroxy-6-trideuteroheptyl) phenyl)-9-methyldec-2-enyliden)-4-methylenecyclohexane-1,3-diol,
(1R,3S,Z)-5-((E)-9-hydroxy-3-(3-(6-hydroxy-6-methylheptyl)phenyl)-9-methyldec-2-enyliden)4-methylenecyclohexane-1,3-diol,
(1R,3S,Z)-5-((E)-9-hydroxy-3-(3-(7,7,7-trideutero-6-hydroxy-6-trideuteroheptyl) phenyl)-9-methyldec-2-enyliden)-4-methylenecyclohexane-1,3-diol,
(1R,3S,Z)-5-((E)-3-(3,5-bis(6-hydroxy-6-methylheptyl) phenyl)allyliden)-4-methylenecyclohexane-1,3-diol,
(1R,3S,Z)-5-((E)-3-(3,5-bis(7,7,7-trideutero-6-hydroxy-6-trideuteroheptyl)phenyl) allyliden)-4-methylenecyclohexane-1,3-diol,
(1R,3S,Z)-5-((E)-3-(3-(5-hydroxy-5-methylhexyl)phenyl)pent-2-enyliden)-4-methylenecyclohexane-1,3-diol,
(1R,3S,Z)-5-((E)-3-(3-(6,6,6-trideutero-5-hydroxy-5-trideuterohexyl)phenyl)pent-2-enyliden)-4-methylenecyclohexane-1,3-diol,
(1R,3S,Z)-5-((E)-3-(3-(5-hydroxy-5-methylhexyl)phenyl)hept-2-enyliden)4-methylenecyclohexane-1,3-diol,
and (1R,3S,Z)-5-((E)-3-(3-(6,6,6-trideutero-5-hydroxy-5-trideuterohexyl)phenyl)hept-2-enyliden)-4-methylenecyclohexane-1,3-diol.

14. A combination of at least a compound of formula (I), as defined in claim 1, and at least an anti-neoplastic compound.

15. The combination according to claim 14, wherein the anti-neoplastic compound is selected from the group consisting of alkylating agents, anti-metabolites, anti-neoplastic antibiotics, topoisomerase inhibitors, mitotic inhibitors, hormonal agents, regulators of the immune system and targeted therapies.

16. The combination according to claim 15, wherein the alkylating agent is selected from a group consisting of nitrogen mustards, nitrosoureas, alkylsulfonates, triazines, ethylamines and drugs with platinum; the anti-metabolite is selected from a group consisting of 5-fluorouracil, 6-mercaptopurine, capecitabine, cladribine, clofarabine, cytarabine, floxiuridine, fludarabine, gemcitabine, hydroxyurea, methotrexate, pemetrexed, pentostatin and thioguanine; the anti-neoplastic antibiotic is selected from a group consisting of anthracyclines and non-anthracins; the topoisomerase inhibitor is selected from a group consisting of inhibitors of topoisomerase I and inhibitors of topoisomerase II; the mitotic inhibitor is selected from a group consisting of taxanes, epothilones, vinca alkaloids and estramustine; the hormonal agent is selected from a group consisting of anti-estrogens, aromatase inhibitors, progestins, anti-androgens, gonadotropin-releasing hormone agonists (GnRH) and analogues of the luteinizing hormone releasing hormone (LHRH); the regulator of the immune system is selected from a group consisting of monoclonal antibody therapy, non-specific immunotherapies and adjuvants, immunomodulatory drugs and anti-cancer vaccines; and targeted therapy is selected from a group consisting of imatinib, gefitinib, sunitinib, bortezomib and trastuzumab.

17. The combination according to claim 16, wherein the nitrogen mustards are selected from a group consisting of mechlorethamine, chlorambucil, cyclophosphamide, iphosphamide and melphalan; nitrosoureas are selected from a group consisting of streptozocin, carmustine and lomustine; alkylsulfonates consist of busulfan; triazines are selected from a group consisting of dacarbazine and temozolomide; ethylenimines are selected from a group consisting of thiotepa and altretamine; platinum drugs are selected from a group consisting of cisplatin, carboplatin and oxaliplatin; anthracyclines are selected from a group consisting of daunorubicin, doxorubicin, epirubicin and idarubicin; non-anthracins are selected from a group consisting of actinomycin D, bleomycin and mitomycin-C; inhibitors of topoisomerase I are selected from a group consisting of topotecan and irinotecan; inhibitors of topoisomerase II are selected from a group consisting of etoposide, teniposide and/or mitoxantrone; the taxanes are selected from a group consisting of paclitaxel and docetaxel; epothilones consist of ixabepilone; vinca alkaloids are selected from a group consisting of vinblastine, vincristine and vinorelbine; antiestrogenics are selected from a group consisting of fulvestrant, tamoxifen and toremifene; aromatase inhibitors are selected from a group consisting of anastrozole, exemestane and letrozole; progestins consist of megestrol acetate; antiandrogens are selected from a group consisting of bicalutamide, flutamide and nilutamide; analogues of the luteinizing hormone releasing hormone (LHRH) are selected from a group consisting of leuprolide and goserelin; monoclonal antibody therapy is selected from a group consisting of rituximab, and alemtuzumab; immunotherapies and non-specific adjuvants are selected from a group consisting of BCG, interleukin-2 and interferon-alpha; the immunomodulating drugs are selected from a group consisting of thalidomide and lenalidomide; and anticancer vaccines consist of sipuleucel-T.

18. A pharmaceutical composition comprising a therapeutically effective amount of a compound of formula (I), as defined in claim 1, together with one or more pharmaceutically acceptable excipients or carriers.

19. The compound formula (Ia), according to claim 5 wherein at least one of $R^1$, $R^3$ and $R^5$ is branched $(C_1-C_{12})$ hydroxyalkyl.

20. The compound formula (Ia), according to claim 5, wherein $X^1$ and $X^2$ are methylene.

* * * * *